United States Patent
Thota et al.

(10) Patent No.: US 7,358,259 B2
(45) Date of Patent: Apr. 15, 2008

(54) HCV INHIBITORS AND METHODS OF USING THEM

(75) Inventors: Sambaiah Thota, Fremont, CA (US); Ankush Argade, Foster City, CA (US); Rajinder Singh, Belmont, CA (US); Henry H. Lu, Foster City, CA (US); Peiyong Huang, San Jose, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 120 days.

(21) Appl. No.: 10/951,181

(22) Filed: Sep. 27, 2004

(65) Prior Publication Data

US 2005/0090521 A1 Apr. 28, 2005

Related U.S. Application Data

(60) Provisional application No. 60/576,536, filed on Jun. 3, 2004, provisional application No. 60/506,556, filed on Sep. 26, 2003.

(51) Int. Cl.
*A61K 31/4745* (2006.01)
*C07D 471/06* (2006.01)

(52) U.S. Cl. .................................... 514/293; 546/82

(58) Field of Classification Search ............... 546/82, 546/81; 514/293
See application file for complete search history.

(56) References Cited

U.S. PATENT DOCUMENTS

| 3,775,417 A | 11/1973 | Ruiter et al. | |
|---|---|---|---|
| 3,891,653 A | 6/1975 | Dreikorn | |
| 4,000,151 A | 12/1976 | Hester et al. | 260/308 |
| 2004/0048882 A1* | 3/2004 | Angibaud et al. | 514/266.31 |

FOREIGN PATENT DOCUMENTS

| DE | 22 06 012 | 8/1972 |
|---|---|---|
| EP | 0 120 484 | 10/1984 |
| EP | 1 162 196 | 12/2001 |
| FR | 2 149 467 | 3/1973 |
| WO | WO 95/26348 | 10/1995 |
| WO | WO 97/48704 | 12/1997 |
| WO | 2000039082 A2 | 7/2000 |
| WO | WO 02/28837 | 4/2002 |
| WO | WO 02/28837 A1 * | 4/2002 |
| WO | WO 03/007945 | 1/2003 |
| WO | WO 03/040112 | 5/2003 |
| WO | WO 03/064456 | 8/2003 |

OTHER PUBLICATIONS

CAPLUS Accession No. 1996: 464309.*
Stadlbauer, et al., "Study of the thermal behavior of azidohetarenes with differential scanning calorimetry", Journal of Biochemical and Biophysical Methods, (2002), 53 (1-3), 89-99.*
CAPLUS Accession No. 1994:533924.*
CAPLUS Accession No. 1993: 551632.*
CAPLUS Accession No. 1990:138965.*
CAPLUS Accession No. 1986:583403.*
CAPLUS Accession No. 1986:442681.*
Mukherjee et al., Syntheses and Bioevaluation of Substituted Dihydropyridines for Pregnancy-Interceptive Activity in Hamsters, J. Med. Chem., 32(10):22972300 (1989).*
Meth-Cohn et al., A Versatile New Synthesis of Quinolines and Related Fused Pyridines, Journal of the Chemical Society, Perkin Transactions 1: Organic and Bio-Organic Chemistry 9:2509-17 (1981).*
McGaw, What is Means When an Examiner Says "Election of Species Requirement," Smith & Hopen Article ID: 37 (2005), available online at: http://www.smithhopen.com/faq_display.asp?faq_id=37 .*
Yanborosova et al., Preparation and pharmacological activity of amides of 2-hydrazocinchoninic, 1,2,4-triazolo[4,3-a]-, and 1,2,3,4-tetrazolo[4,3-a]quinoline-9-carboxylic acids, Khimiko-Farmatsevticheskaya Zhurnal 30(3):52-53 (1996).*
STN results, Document No. 125:75750, Registry Nos. 136354-35-6, 178533-22-7, 178533-23-8, 178533-24-9, 178533-25-0, 178533-26-1, and 178533-27-2.*
Database Beilstein XP002313584, Database accession No. Beilstein Registry No. 13090-43-2, S-triazolo '1, 5-alauinoline & Heterocycles vol. 31, No. 2, 1990, pp. 289-304.
Tetrahedron, vol. 54, 1998, pp. 3913-3918, XP002313579, compound 7.
Journal of Organic Chemistry, vol. 44, No. 2, 1979, pp. 285-287, XP002313578, p. 286, compound 7.
Tetrahedron Letters, vol. 21, 1980, pp. 3723-3726, XP002313580, p. 3724, compound 12.
Journal of Heterocyclic Chemistry, vol. 27, No. 263, 1990, pp. 263-268, XP002313581, scheme 4, compound 10a, p264.
Journal of Organic Chemistry, vol. 20, 1955, pp. 1443-1447, XP002313582, compound IV.
Journal of Viral Hepatitis, 2003, pp. 405-412, XP002313583, p. 409, figure 4.
Porter et al.; "Tetraxolo [1,5-a] quinolines and 1,2,3-Traiazolo [1,5-a] quinazolines by the Action of Cyano-carbanions on 2-Azidoarylcarbonyl Compounds", SYNTHESIS, Jul. 1997, pp. 773-777.
Garanti et al.; "Thermochemical Behavior of o-Azidocinnamonitriles", J. Org. Chem., 1980, 45, pp. 4767-4769.
Ihsan A. Shehata; "Synthesis of Some Fused Quinoline Derivatives", Chemical Monthly, 1990, pp. 1017-1021.
Dreikorn et al.; "Retrospective Quantitative Structure-Activity Relationship (QSAR) Analysis of Tetrazolo-and Triazoloquinolines, a Series of Rice Blast Control Agents", Synthesis And Chemistry of Agrochemicals IV; American Chemical Society, 1995, pp. 354-374.
Yanborisova et al.; "Synthesis of 1,2,4-triazolo [4,3-a] quinoline-9-, 1,2,3,4-tetrazolo [4,3-a] quinoline-9-, and 1,2,4-triazino [4,3-a] quinoline-10-carboxylic acids based on 2-chloro- and 2-hydrazinocinchoninic acids", Chemical Abstracts Accession No. 116:194271; 2004.
Ramadam Mekheimer; "A Novel Thermal Decomposition of 4-Substituted 8-Methyl-tetrazolo [1,5-z] quinolines: Synthesis of 2-Aryl-7-methyl-pyrazolo [3,4-b] puinolines", J. Chem. Research, 1994, pp. 304-305.

* cited by examiner

Primary Examiner—Charanjit S. Aulakh
(74) Attorney, Agent, or Firm—McDonnell Boehnen Hulbert & Berghoff LLP

(57) ABSTRACT

The present invention comprises tetrazoloquinoline-compounds that are inhibitors of HCV. Compositions comprising the compounds in combination with a pharmaceutically acceptable carrier are also disclosed, as are methods of using the compounds and compositions to inhibit HCV infection of a cell, particular in the form of treating HCV infection in a mammal.

18 Claims, No Drawings

HCV INHIBITORS AND METHODS OF USING THEM

This application claims priority from U.S. Provisional Patent Application No. 60/506,556, filed on Sep. 26, 2003 and from U.S. Provisional Patent Application No. 60/576,536, filed on Jun. 3, 2004.

BACKGROUND OF THE INVENTION

1. Field of the Invention

The present invention is in the field of small molecule inhibitors of HCV and methods of using them to inhibit HCV.

2. Summary of the Related Art

The hepatitis C virus (HCV) is one of the most important causes of chronic liver disease in the United States. It accounts for about 15 percent of acute viral hepatitis, 60 to 70 percent of chronic hepatitis, and up to 50 percent of cirrhosis, end-stage liver disease, and liver cancer. Almost 4 million Americans, or 1.8 percent of the U.S. population, have antibody to HCV (anti-HCV), indicating ongoing or previous infection with the virus. Hepatitis C causes an estimated 8,000 to 10,000 deaths annually in the United States.

A distinct and major characteristic of hepatitis C is its tendency to cause chronic liver disease. At least 75 percent of patients with acute hepatitis C ultimately develop chronic infection, and most of these patients have accompanying chronic liver disease.

Chronic hepatitis C varies greatly in its course and outcome. At one end of the spectrum are patients who have no signs or symptoms of liver disease and completely normal levels of serum liver enzymes. Liver biopsy usually shows some degree of chronic hepatitis, but the degree of injury is usually mild, and the overall prognosis may be good. At the other end of the spectrum are patients with severe hepatitis C who have symptoms, HCV RNA in serum, and elevated serum liver enzymes, and who ultimately develop cirrhosis and end-stage liver disease. In the middle of the spectrum are many patients who have few or no symptoms, mild to moderate elevations in liver enzymes, and an uncertain prognosis. Researchers estimate that at least 20 percent of patients with chronic hepatitis C develop cirrhosis, a process that takes 10 to 20 years. After 20 to 40 years, a smaller percentage of patients with chronic disease develop liver cancer. The therapy of chronic hepatitis C has evolved steadily since alpha interferon was first approved for use in this disease more than ten years ago. At the present time, the optimal regimen appears to be a 24- or 48-week course of the combination of pegylated alpha interferon and ribavirin.

Two forms of peginterferon have been developed and studied in large clinical trials: peginterferon alfa-2a (Pegasys®: Hoffman La Roche: Nutley, N.J.) and peginterferon alfa-2b (Pegintron®: Schering-Plough Corporation, Kenilworth, N.J.). These two products are roughly equivalent in efficacy and safety, but have different dosing regimens. Peginterferon alfa-2a is given subcutaneously in a dose of 180 mcg per week. Peginterferon alfa-2b is given subcutaneously weekly in doses of 1.5 mcg per kilogram per week (thus in the range of 75 to 150 mcg per week).

Ribavirin is an oral antiviral agent that has activity against a broad range of viruses. By itself, ribavirin has little effect on HCV, but adding it to interferon increases the sustained response rate by two- to three-fold. For these reasons, combination therapy is now recommended for hepatitis C and interferon monotherapy is applied only when there are specific reasons not to use ribavirin.

Ribavirin is an oral medication, given twice a day in 200-mg capsules for a total daily dose of 800 to 1,200 mg based upon body weight and the form of peginterferon. When combined with peginterferon alfa-2b, the recommended dose of ribavirin is 800 mg per day. When combined with peginterferon alfa-2a, the dose of ribavirin is 1,000 mg for patients who weigh less than 75 kilograms (165 pounds) and 1,200 mg for those who weight more than 75 kilograms. In all situations, ribavirin is given in two divided doses daily.

At the present, peginterferon alfa-2a has not been approved for use in chronic hepatitis C in the United States and is available only in clinical trials. Thus, only peginterferon alfa-2b is available for general use.

Combination therapy leads to rapid improvements in serum ALT levels and disappearance of detectable HCV RNA in up to 70 percent of patients. However, long-term improvement in hepatitis C occurs only if HCV RNA disappears during therapy and stays undetectable once therapy is stopped. Among patients who become HCV RNA negative during treatment, a proportion relapse when therapy is stopped. The relapse rate is lower in patients treated with combination therapy compared with monotherapy. Thus, a 48-week course of combination therapy using peginterferon and ribavirin yields a sustained response rate of approximately 55 percent. A similar course of peginterferon monotherapy yields a sustained response rate of only 35 percent. A response is considered "sustained" if HCV RNA remains undetectable for six months or more after stopping therapy.

The optimal duration of treatment varies depending on whether interferon monotherapy or combination therapy is used, as well as by HCV genotype. For patients treated with peginterferon monotherapy, a 48-week course is recommended, regardless of genotype. For patients treated with combination therapy, the optimal duration of treatment depends on viral genotype. Patients with genotypes 2 and 3 have a high rate of response to combination treatment (70 to 80 percent), and a 24-week course of combination therapy yields results equivalent to those of a 48-week course. In contrast, patients with genotype 1 have a lower rate of response to combination therapy (40 to 45 percent), and a 48-week course yields a significantly better sustained response rate. Again, because of the variable responses to treatment, testing for HCV genotype is clinically useful when using combination therapy.

In view of the foregoing, there is a desire for alternative, more effective agents for treating HCV infection.

SUMMARY OF THE INVENTION

The invention provides compounds and methods for treating HCV infection. The invention provides new inhibitors of HCV.

In a first aspect, the invention provides compounds that are useful as inhibitors of HCV.

In a second aspect, the invention provides a composition comprising an inhibitor of HCV according to the invention and a pharmaceutically acceptable carrier, excipient, or diluent.

In a third aspect, the invention provides a method of inhibiting HCV in a cell, comprising contacting a cell in which inhibition of HCV is desired with an inhibitor of HCV of the invention.

DETAILED DESCRIPTION OF THE PREFERRED EMBODIMENTS

The foregoing merely summarizes certain aspects of the invention and is not intended to be limiting in nature. These aspects and other aspects and embodiments are described more fully below.

The first aspect of the invention provides for compounds represented by formula I

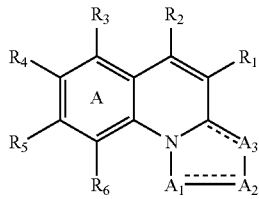

I or a pharmaceutically acceptable salt thereof wherein $R_1$ and $R_2$ are independently hydrogen, $C_1$-$C_6$-alkyl, heterocyclic, $C_1$-$C_6$-alkyl-OH, aryl, heteroaryl, halogen, cyano, —CO—H, —CO—OH, —CO—$OR_7$, —CO—$NH_2$, —CO—$NHR_7$, —CO—$NR_7R_7$, —CO—NH—OH, —CO—NH—$OR_7$, —CO—N($R_7$)$OR_7$, —CO—$R_7$, —$SO_2NH_2$, —$SO_2NHR_7$, —$SO_2NR_7R_7$, —$SO_2$-heteroaryl, —$SO_2$—aryl, —$NHR_7$, $C_1$-$C_6$-alkyl-NH($R_7$)-aryl, —NH($R_7$)-aryl, —CO-heteroaryl, —NH—CO—O—$R_7$-aryl, —NH—CO—NH—$SO_2$-aryl, —NH—CO—$OR_7$, —NH—CO—NH—($C_1$-$C_6$-alkyl) or —NH—CO—($C_1$-$C_6$alkyl), wherein each of the heteroaryl and aryl groups are optionally substituted with $C_1$-$C_6$-alkyl, nitro, hydroxy, $C_1$-$C_6$-alkoxy, —CO—O—($C_1$-$C_6$-alkyl), cyano, —O-halo($C_1$-$C_6$-alkyl), halo($C_1$-$C_6$-alkyl) or halogen; or $R_1$ or $R_2$ is a group selected from

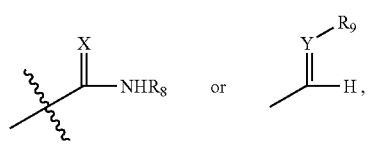

wherein $R_8$ is hydrogen or hydroxy; X is =NH or =S, Y is =N—, and $R_9$ is hydroxy, $C_1$-$C_6$-alkoxy or aryl optionally substituted with hydroxy or $C_1$-$C_6$-alkyl; or $R_1$ and $R_2$ together with the carbon atoms to which they are attached form a mono or bicyclic aryl or heteroaryl;

$R_3$, $R_4$, $R_5$ and $R_6$ are independently hydrogen, nitro, $C_1$-$C_6$-alkyl, aryl, —O-halo($C_1$-$C_6$-alkyl), halo($C_1$-$C_6$-alkyl), —O—($C_3$-$C_6$-cycloalkyl), —S—($C_1$-$C_6$-alkyl), heterocyclyl, $C_1$-$C_6$-alkoxy, —($C_1$-$C_6$-alkoxy)-aryl, azido, halogen, —$OCF_3$, —$CF_3$, —CO—H, —CO—OH, —CO—$OR_7$, —CO—$NH_2$, —CO—$NHR_7$, —CO—$NR_7R_7$, —CO—N($R_7$)$OR_7$, —CO—$R_7$, —$SO_2$—($C_1$-$C_6$-alkyl), —$SO_2NH_2$, —$SO_2NHR_7$, —$SO_2NR_7R_7$, —CO-heteroaryl, —$NH_2$, —$NHR_7$, —$NR_7R_7$, —OH, —N($R_7$)—CO—$R_7$, —$NHSO_2R_7$, —N($R_7$)—CO—$OR_7$ or —N($R_7$)—CO—$NR_7R_7$;

$R_4$ and $R_5$ together with the carbon atoms to which they are attached form a heteroaryl;

$R_7$ is a cation, $C_0$-$C_6$-alkyl, —($C_1$-$C_6$-alkyl)-OH, —($C_1$-$C_6$-alkyl)-O—($C_1$-$C_6$-alkyl), —($C_1$-$C_6$-alkyl)-CN, $C_2$-$C_6$-alkene, heterocyclyl, aryl, heteroaryl or —($C_1$-$C_6$-alkyl)-aryl, wherein each of the aryl, heterocyclyl and heteroaryl groups are optionally substituted with $C_1$-$C_6$-alkyl, nitro, hydroxy, $C_1$-$C_6$-alkoxy, —CO—O—($C_1$-$C_6$-alkyl), cyano, —O-halo($C_1$-$C_6$-alkyl), halo($C_1$-$C_6$-alkyl) or halogen;

$A_1$, $A_2$ and $A_3$ are independently carbon, oxygen, or nitrogen, wherein the carbon or nitrogen is optionally substituted with halo or $C_1$-$C_6$-alkyl; and ring A optionally contains from 1 to 2 nitrogen atoms;

provided that when $A_1$, $A_2$, and $A_3$ are N:

$R_1$ to $R_6$ are not all hydrogen;

when $R_2$ to $R_6$ are hydrogen, $R_1$ is not —$CH_3$, —CO-phenyl, —CO—H or chloro;

when $R_1$ and $R_3$ to $R_6$ are hydrogen, $R_2$ is not bromo, —$CH_2$—OH, cyano, iodo, —CO—OH, —$CH_3$, —$CH_2OCH_3$, morpholino, —$CH_2NH$—$CH_2CH_3$, vinyl, —$CH_2CH_3$, chloro, —$CH_2NH_2$ or azido;

when $R_1$ to $R_3$ and $R_5$ to $R_6$ are hydrogen, $R_4$ is not chloro, ethynyl or —$CH_3$;

when $R_1$ to $R_4$ and $R_6$ are hydrogen, $R_5$ is not —$CH_3$ or —$CH_2NH$-isopropyl;

when $R_1$ to $R_5$ are hydrogen, $R_6$ is not —$CH_2Br$, chloro, —$CH_3$, —$CH_2$—OH, —CO—H, —$NO_2$, —$NH_2$, acetamido, —$CH_2OCH_3$, —$CH_2$—CN, propyl, iodo or —$CH_2OCH_2CH_3$; and the compounds of formula I are not one of the following combinations

| $A_1$ | $A_2$ | $A_3$ | $R_1$ | $R_2$ | $R_3$ | $R_4$ | $R_5$ | $R_6$ |
|---|---|---|---|---|---|---|---|---|
| N | N | N | —CO—H | —H | —H | —H | —$CH_3$ | —H |
| N | N | N | —CO—OH | —H | —H | —$N_3$ | —$N_3$ | —H |
| N | N | N | —CO—OH | —H | —H | —$OCH_3$ | —$OCH_3$ | —H |
| N | N | N | —CO—H | —H | —H | —H | —$CH_3$ | —H |
| N | N | N | —H | —$CH_3$ | —H | —H | —$OCH_3$ | —H |
| N | N | N | —CN | piperidyl | —H | —H | —H | —H |
| N | N | N | —H | —Cl | —H | —H | —H | —$CH_3$ |
| N | N | N | —CN | —Cl | —H | —H | —H | —H |
| N | N | N | —H | —$CH_3$ | —H | —$CH_2CH_3$ | —H | —H |
| C | N | N | —H | —$CH_3$ | —H | —H | —H | —H |
| C | N | N | —H | —H | —H | —H | —H | —H |
| N | N | N | —H | —$CH_3$ | —H | —H | —H | —F |
| N | N | N | —H | —$CH_3$ | —H | —H | —H | —Br |
| N | N | N | —$CH_3$ | —Cl | —H | —H | —H | —H |
| N | N | N | —$CH_2CH_3$ | —Cl | —H | —H | —H | —H |
| N | N | N | —H | —Cl | —H | —H | —H | —$CH_2NHCH_3$ |

-continued

| $A_1$ | $A_2$ | $A_3$ | $R_1$ | $R_2$ | $R_3$ | $R_4$ | $R_5$ | $R_6$ |
|---|---|---|---|---|---|---|---|---|
| N | N | N | —H | —Cl | —H | —CH$_3$ | —H | —H |
| N | N | N | —H | —Cl | —H | —H | —H | —CH$_3$ |
| N | N | N | —H | —Cl | —H | —H | —H | —Cl |
| N | N | N | —H | —N$_3$ | —H | —CH$_3$ | —H | —H |
| N | N | N | —H | —N$_3$ | —H | —H | —H | —Cl |
| N | N | N | —H | —N$_3$ | —H | —CH$_3$ | —H | —H |
| N | N | N | —CH$_3$ | —Cl | —H | —H | —H | —CH$_3$ |
| N | N | N | —H | —CH$_2$Cl | —H | —H | —H | —CH$_2$Cl |
| N | N | N | —CH$_3$ | —Cl | —H | —H | —H | —Cl |
| N | N | N | —H | —CH$_3$ | —H | —H | —H | —CH$_3$ |
| N | N | N | —H | —CH$_3$ | —H | —CH$_3$ | —H | —H |
| N | N | N | —CH$_3$ | —Cl | —H | —H | —H | —F |
| N | N | N | —H | —Cl | —H | —H | —H | —F |
| N | N | N | —H | —Cl | —Cl | —H | —H | —Cl |
| N | N | N | —H | —Cl | —H | —H | —H | —CH$_3$ |
| N | N | N | —H | —CH$_3$ | —H | —H | —H | —CH$_2$CH$_3$ |
| N | N | N | —H | —CH$_3$ | —H | —CH$_2$CH$_3$ | —H | —H |
| N | N | N | —H | morpholino | —H | —Cl | —H | —Cl |
| N | N | N | —H | —CH$_3$ | —H | —Cl | —H | —H |
| N | N | N | —Cl | —CH$_3$ | —H | —H | —H | —H |
| N | N | N | —H | —CH$_3$ | —H | —H | —H | —Cl |

In one embodiment of the invention, the compounds of formula I are compounds wherein $A_1$, $A_2$ and $A_3$ are independently carbon or nitrogen each optionally substituted with halo or $C_1$-$C_6$-alkyl. In a preferred embodiment one of $A_1$, $A_2$ and $A_3$ is carbon optionally substituted with halo or $C_1$-$C_6$-alkyl. Preferably, halo is chloro, fluoro or bromo and $C_1$-$C_6$-alkyl is methyl, ethyl, or propyl. More preferably, halo is chloro and $C_1$-$C_6$-alkyl is methyl.

The invention also provides for compounds represented by formula II

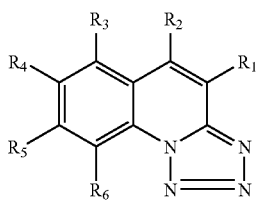

II or a pharmaceutically acceptable salt thereof wherein $R_1$ and $R_2$ are independently hydrogen, $C_1$-$C_6$-alkyl, heterocyclic, $C_1$-$C_6$-alkyl-OH, aryl, heteroaryl, halogen, cyano, —CO—H, —CO—OH, —CO—OR$_7$, —CO—NH$_2$, —CO—NHR$_7$, —CO—NR$_7$R$_7$, —CO—NH—OH, —CO—NH—OR$_7$, —CO—N(R$_7$)—OR$_7$, —CO—R$_7$, —SO$_2$NH$_2$, —SO$_2$NHR$_7$, —SO$_2$NR$_7$R$_7$, —SO$_2$-heteroaryl, —SO$_2$-aryl, —NHR$_7$, $C_1$-$C_6$-alkyl-NH(R$_7$)-aryl, —NH(R$_7$)-aryl, —CO-heteroaryl, —NH—CO—O—R$_7$-aryl, —NH—CO—NH—SO$_2$-aryl, —NH—CO—OR$_7$, —NH—CO—NH—(C$_1$-C$_6$-alkyl) or —NH—CO—(C$_1$-C$_6$alkyl), wherein each of the heteroaryl and aryl groups are optionally substituted with $C_1$-$C_6$-alkyl, nitro, hydroxy, $C_1$-$C_6$-alkoxy, —CO—O—(C$_1$-$C_6$-alkyl), cyano, —O-halo($C_1$-$C_6$-alkyl), halo($C_1$-$C_6$-alkyl) or halogen; or $R_1$ or $R_2$ is a group selected from

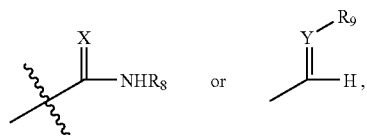

wherein $R_8$ is hydrogen or hydroxy; X is =NH or =S, Y is =N—, and $R_9$ is hydroxy, $C_1$-$C_6$-alkoxy or aryl optionally substituted with hydroxy or $C_1$-$C_6$-alkyl; or $R_1$ and $R_2$ together with the carbon atoms to which they are attached form a mono or bicyclic aryl or heteroaryl;

$R_3$, $R_4$, $R_5$ and $R_6$ are independently hydrogen, nitro, $C_1$-$C_6$-alkyl, aryl, —O-halo($C_1$-$C_6$-alkyl), halo($C_1$-$C_6$-alkyl), —O—($C_3$-$C_6$-cycloalkyl), —S—($C_1$-$C_6$-alkyl), heterocyclyl, $C_1$-$C_6$-alkoxy, —($C_1$-$C_6$-alkoxy)-aryl, azido, halogen, —OCF$_3$, —CF$_3$, —CO—H, —CO—OH, —COOR$_7$, —CO—NH$_2$, —CO—NHR$_7$, —CO—NR$_7$R$_7$, —CO—N(R$_7$)OR$_7$, —CO—R$_7$, —SO$_2$—($C_1$-$C_6$-alkyl), —SO$_2$NH$_2$, —SO$_2$NHR$_7$, —SO$_2$NR$_7$R$_7$, —CO-heteroaryl, —NH$_2$, —NHR$_7$, —NR$_7$R$_7$, —OH, —N(R$_7$)—CO—R$_7$, —NHSO$_2$R$_7$, —N(R$_7$)—CO—OR$_7$ or —N(R$_7$)—CO—NR$_7$R$_7$;

$R_4$ and $R_5$ together with the carbon atoms to which they are attached form a heteroaryl;

$R_7$ is a cation, $C_0$-$C_6$-alkyl, —($C_1$-$C_6$-alkyl)-OH, —($C_1$-$C_6$-alkyl)-O—($C_1$-$C_6$-alkyl), —($C_1$-$C_6$-alkyl)-CN, $C_2$-$C_6$-alkene, heterocyclyl, aryl, heteroaryl or —($C_1$-$C_6$-alkyl)-aryl, wherein each of the aryl, heterocyclyl and heteroaryl groups are optionally substituted with $C_1$-$C_6$-alkyl, nitro, hydroxy, $C_1$-$C_6$-alkoxy, —CO—O—($C_1$-$C_6$-alkyl), cyano, —O-halo($C_1$-$C_6$-alkyl), halo($C_1$-$C_6$-alkyl) or halogen; and provided that:

$R_1$ to $R_6$ are not all hydrogen;

when $R_2$ to $R_6$ are hydrogen, $R_1$ is not —CO-phenyl, —CO—H or chloro;

when $R_1$ and $R_3$ to $R_6$ are hydrogen, $R_2$ is not bromo, —CH$_2$—OH, cyano, iodo, —CO—OH, —CH$_3$, —CH$_2$OCH$_3$, morpholino, —CH$_2$NH—CH$_2$CH$_3$, vinyl, —CH$_2$CH$_3$, chloro, —CH$_2$NH$_2$ or azido;

when $R_1$ to $R_3$ and $R_5$ to $R_6$ are hydrogen, $R_4$ is not chloro, ethynyl or —CH$_3$;

when $R_1$ to $R_4$ and $R_6$ are hydrogen, $R_5$ is not —CH$_3$ or —CH$_2$NH-isopropyl;

when $R_1$ to $R_5$ are hydrogen, $R_6$ is not —CH$_2$Br, chloro, —CH$_3$, —CH$_2$—OH, —CO—H, —NO$_2$, —NH$_2$, acetamido, —CH$_2$OCH$_3$, —CH$_2$—CN, propyl, iodo or —CH$_2$OCH$_2$CH$_3$; and the compounds of formula II are not one of the following combinations

| R$_1$ | R$_2$ | R$_3$ | R$_4$ | R$_5$ | R$_6$ |
|---|---|---|---|---|---|
| —CO—H | —H | —H | —H | —CH$_3$ | —H |
| —CO—OH | —H | —H | —N$_3$ | —N$_3$ | —H |
| —CO—OH | —H | —H | —OCH$_3$ | —OCH$_3$ | —H |
| —CO—H | —H | —H | —H | —CH$_3$ | —H |
| —H | —CH$_3$ | —H | —H | —OCH$_3$ | —H |
| —CN | piperidyl | —H | —H | —H | —H |
| —H | —Cl | —H | —H | —H | —CH$_3$ |
| —CN | —Cl | —H | —H | —H | —H |
| —H | —CH$_3$ | —H | —CH$_2$CH$_3$ | —H | —H |
| —H | —CH$_3$ | —H | —H | —H | —F |
| —H | —CH$_3$ | —H | —H | —H | —Br |
| —CH$_3$ | —Cl | —H | —H | —H | —H |
| —CH$_2$CH$_3$ | —Cl | —H | —H | —H | —H |
| —H | —Cl | —H | —H | —H | —CH$_2$NHCH$_3$ |
| —H | —Cl | —H | —CH$_3$ | —H | —H |
| —H | —Cl | —H | —H | —H | —CH$_3$ |
| —H | —Cl | —H | —H | —H | —Cl |
| —H | —N$_3$ | —H | —CH$_3$ | —H | —H |
| —H | —N$_3$ | —H | —H | —H | —Cl |
| —H | —N$_3$ | —H | —CH$_3$ | —H | —H |
| —CH$_3$ | —Cl | —H | —H | —H | —CH$_3$ |
| —H | —CH$_2$Cl | —H | —H | —H | —CH$_2$Cl |
| —CH$_3$ | —Cl | —H | —H | —H | —Cl |
| —H | —CH$_3$ | —H | —H | —H | —CH$_3$ |
| —H | —CH$_3$ | —H | —CH$_3$ | —H | —H |
| —CH$_3$ | —Cl | —H | —H | —H | —F |
| —H | —Cl | —H | —H | —H | —F |
| —H | —Cl | —Cl | —H | —H | —Cl |
| —H | —Cl | —H | —H | —H | —CH$_3$ |
| —H | —CH$_3$ | —H | —H | —H | —CH$_2$CH$_3$ |
| —H | —CH$_3$ | —H | —CH$_2$CH$_3$ | —H | —H |
| —H | morpholino | —H | —Cl | —H | —Cl |
| —H | —CH$_3$ | —H | —Cl | —H | —H |
| —Cl | —CH$_3$ | —H | —H | —H | —H |
| —H | —CH$_3$ | —H | —H | —H | —Cl |

In one embodiment of the invention, the compounds of formula II are compounds wherein R$_1$ is —CO—NH—OR$_7$, R$_5$ is halogen, R$_2$ to R$_4$ and R$_6$ are hydrogen. More preferably, R$_7$ is hydrogen and R$_5$ is chloro.

In another embodiment, the compounds of formula II are compounds wherein R$_1$ is aryl optionally substituted with one or more halo(C$_1$-C$_6$-alkyl), cyano, —O-halo(C$_1$-C$_6$-alkyl), or halogen, R$_5$ is halogen, R$_2$ to R$_4$ and R$_6$ are hydrogen. More preferably, the compounds are compounds wherein R$_1$ is phenyl optionally substituted with one or more —CF$_3$ or F and R$_5$ is chloro.

In yet another embodiment, the compounds of formula II are compounds wherein R$_1$ is —CO—NH—OR$_7$, R$_6$ is halogen and R$_2$ to R$_5$ are hydrogen. Preferred compounds of this embodiment are compound wherein R$_7$ is isobutyl, propyl, isopropyl or ethyl and R$_6$ is chloro.

In one other embodiment, the compounds of formula II are compounds wherein R$_1$ is —NH—CO—OR$_7$, R$_5$ is halogen, R$_2$ to R$_4$ and R$_6$ are hydrogen, preferably R$_7$ is tertbutyl and R$_5$ is chloro.

In another embodiment according to formula II, the compounds are compounds wherein R$_1$ is —CO—OR$_7$, R$_6$ is halo(C$_1$-C$_6$-alkyl) and R$_2$ to R$_5$ are hydrogen, preferably the compound are compounds wherein R$_7$ is hydrogen and R$_6$ is —CF$_3$.

In still another embodiment, the compounds according to formula II are compounds wherein R$_1$ is —NH—CO—NH—SO$_2$aryl, —NH—CO—NH—(C$_1$-C$_6$-alkyl), C$_1$-C$_6$-alkyl-OH, —CO—H, —CO—NH$_2$, —CO—NH—R$_7$, —CO—NH—OR$_7$, —SO$_2$-aryl, —SO$_2$-heteroaryl, heteroaryl, —CO—OR$_7$ or a group represented by

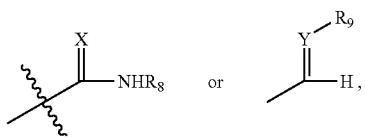

wherein R$_8$ is hydrogen or hydroxy, X is =N or =S, Y is =N—, and R$_9$ is hydroxy or C$_1$-C$_6$-alkoxy; R$_4$ and R$_5$ are independently selected from hydrogen, —S—(C$_1$-C$_6$-alkyl), C$_1$-C$_6$-alkyl, —O—(C$_3$-C$_6$-cycloalkyl), C$_1$-C$_6$-alkoxy, halogen, —SO$_2$—(C$_1$-C$_6$-alkyl), heterocyclyl, —O-halo(C$_1$-C$_6$-alkyl), halo(C$_1$-C$_6$-alkyl), —NH$_2$ or together with the carbon atom to which they are attached form a heteroaryl group; R$_2$, R$_3$ and R$_6$ are hydrogen; and wherein the each of the aryl, heteroaryl and heterocyclyl groups are optionally substituted with —CO—O—(C$_1$-C$_6$-alkyl), C$_1$-C$_6$-alkyl, nitro, hydroxy, C$_1$-C$_6$-alkoxy, cyano, —O-halo(C$_1$-C$_6$-alkyl), halo(C$_1$-C$_6$-alkyl) or halogen.

In another embodiment, the compounds of according to formula II are compounds wherein R$_1$ and R$_2$ are independently —NH(R$_7$)-aryl, —CO—OH, —CO—OR$_7$, C$_1$-C$_6$-alkyl, aryl or together with the carbon atoms to which they are attached form a bicyclic heteroaryl; R$_3$ to R$_6$ are hydrogen; and wherein each of the aryl and heteroaryl groups are optionally substituted with —CO—O—(C$_1$-C$_6$-alkyl), C$_1$-C$_6$-alkyl, nitro, hydroxy, C$_1$-C$_6$-alkoxy, cyano, —O-halo (C$_1$-C$_6$-alkyl), halo(C$_1$-C$_6$-alkyl) or halogen.

In another embodiment, the compounds of formula II are compounds wherein R$_1$ is —CO—OH, —CO—OR$_7$, or —CO—NH—OR$_7$; R$_6$ is C$_1$-C$_6$-alkyl, halogen, or —O—(C$_1$-C$_6$-alkyl); and R$_2$ to R$_5$ are hydrogen.

In still another embodiment, the compounds according to formula II are compounds wherein R$_1$ is —CO—OR$_7$; R$_3$ is azido or C$_1$-C$_6$-alkyl; and R$_2$, R$_4$ to R$_6$ are hydrogen.

In a second aspect, the invention comprises a composition comprising a compounds of any one of paragraphs [0017]-[0028] and a pharmaceutically acceptable carrier, excipient, or diluent.

In a third aspect, the invention provides a method of inhibiting HCV in a cell, comprising contacting a cell in which inhibition of HCV is desired with an inhibitor of HCV according to any one of paragraphs [0017]-[0028] or a composition according to paragraph [0029]. Because compounds of the invention inhibit HCV, they are also useful research tools for in vitro study HCV infections in cells and cellular systems.

In a preferred embodiment of the third aspect, the invention comprises a method of treating an HCV infection in a mammal, preferably a human, comprising administering to the mammal a therapeutically effective amount of a composition according to paragraph [0029].

Definitions

Unless expressly stated to the contrary, the following definitions apply uniformly throughout. For simplicity, the substituents have been defined primarily as univalent chemical moieties (e.g., alkyl, aryl, etc.). Nevertheless, such terms are also used to convey corresponding multivalent moieties under the appropriate structural circumstances. All atoms are understood to have their normal number of valences for bond formation (i.e., 4 for carbon, 3 for N, 2 for O, and 2, 4, or 6 for S, depending on the oxidation state of the S). Also, where a chemical structure exists in multiple tautomeric forms, all are envisioned as part of the invention.

The term hydrocarbyl refers to a saturated, mono- or poly-unsaturated straight, branched or cyclic hydrocarbon and specifically includes methyl, ethyl, propyl, isopropyl, butyl, isobutyl, t-butyl, pentyl, cyclopentyl, isopentyl, neopentyl, hexyl, isohexyl, cyclohexyl, 3-methylpentyl, 2,2-dimethylbutyl, 2,3-dimethylbutyl, acetylenyl, propynyl, cyclopropyl, and —C≡C—CH$_2$(alkyl) (including —C≡C—CH$_2$(CH$_3$). A hydrocarbyl moiety may be defined to include a "C$_0$-C$_n$-hydrocarbyl," "C$_0$-C$_n$-alkyl," or the like, in which n is an integer, as in "aryl-C$_0$-C$_3$-alkyl." In these instances a "C$_0$" moiety represents a direct bond. So, for example, "aryl-C$_0$-C$_3$-alkyl" encompasses both aryl-C$_1$-C$_6$-alkyl moieties as well as aryl moieties (C$_0$-alkyl).

An "aryl" group is a C$_6$-C$_{14}$ aromatic moiety comprising one to three aromatic rings, which is optionally substituted. Preferably, the aryl group is a C$_6$-C$_{10}$ aryl group. Preferred aryl groups include, without limitation, phenyl, naphthyl, anthracenyl, and fluorenyl. An "aralkyl" or "arylalkyl" group comprises an aryl group covalently linked to an alkyl group, either of which may independently be optionally substituted or unsubstituted. Preferably, the aralkyl group is (C$_6$-C$_{10}$)aryl-(C$_1$-C$_6$)alkyl, including, without limitation, benzyl, phenethyl, and naphthylmethyl.

The term heteroatom means O, S, or N.

A "heterocyclyl" group is a mono-, bi-, or tricyclic structure having from 3 to 14 atoms, wherein one or more annular atoms are selected from the group consisting of N, O, and S. The heterocyclic group is optionally substituted on carbon at one or more positions. The heterocyclic group is also independently optionally substituted on nitrogen with alkyl, aryl, aralkyl, alkylcarbonyl, alkylsulfonyl, arylcarbonyl, arylsulfonyl, alkoxycarbonyl, aralkoxycarbonyl, or on sulfur with oxo or lower alkyl. Preferred heterocyclic groups include, without limitation, epoxy, aziridinyl, tetrahydrofuranyl, pyrrolidinyl, piperidinyl, piperazinyl, thiazolidinyl, oxazolidinyl, oxazolidinonyl, and morpholino. In certain preferred embodiments, the heterocyclic group is fused to an aryl, heteroaryl, or cycloalkyl group. Examples of such fused heterocycles include, without limitation, tetrahydroquinoline and dihydrobenzofuran. Specifically excluded from the scope of this term are compounds having adjacent annular O and/or S atoms.

In certain preferred embodiments, the heterocyclic group is a heteroaryl group. As used herein, the term "heteroaryl" refers to groups having 5 to 14 ring atoms, preferably 5, 6, 9, or 10 ring atoms; having 6, 10, or 14 π electrons shared in a cyclic array; and having, in addition to carbon atoms, from zero to three heteroatoms per ring selected from the group consisting of N, O, and S, provided there is at least one heteroatom. A "heteroaralkyl" or "heteroarylalkyl" group comprises a heteroaryl group covalently linked to an alkyl group, either of which is independently optionally substituted or unsubstituted. Preferred heteroalkyl groups comprise a C$_1$-C$_6$ alkyl group and a heteroaryl group having 5, 6, 9, or 10 ring atoms. Specifically excluded from the scope of this term are compounds having adjacent annular O and/or S atoms.

For simplicity, reference to a "C$_n$-C$_m$" heterocyclyl or "C$_n$-C$_m$" heteroaryl means a heterocyclyl or heteroaryl having from "n" to "m" annular atoms, where "n" and "m" are integers. Thus, for example, a C$_5$-C$_6$-heterocyclyl is a 5- or 6-membered ring having at least one heteroatom, and includes pyrrolidinyl (C$_5$) and piperidinyl (C$_6$); C$_6$-hetoaryl includes, for example, pyridyl and pyrimidyl.

Preferred heterocyclyls and heteroaryls include, but are not limited to, acridinyl, azocinyl, benzimidazolyl, benzofuranyl, benzothiofuranyl, benzothienyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thienyl, triazinyl, 1,2,3-triazolyl, 1,2,4-triazolyl, 1,2,5-triazolyl, 1,3,4-triazolyl, and xanthenyl.

Open valences on the radical moieties described herein can occur on any one (or more for divalent radicals) of the atoms within the moiety. For example, the C$_3$ alkyl moiety includes both propyl and isopropyl. As another example, a divalent C$_4$ alkylene moiety includes both tetramethylene (—CH$_2$(CH$_2$)$_2$CH$_2$—) and ethylethylene (—CH(CH$_2$CH$_3$)CH$_2$—).

A moiety that is substituted is one in which one or more hydrogens have been independently replaced with another chemical substituent. As a non-limiting example, substituted phenyls include 2-flurophenyl, 3,4-dichlorophenyl, 3-chloro-4-fluoro-phenyl, 2-fluor-3-propylphenyl. As another non-limiting example, substituted n-octyls include 2,4 dimethyl-5-ethyl-octyl and 3-cyclopentyl-octyl. As another example, an oxo-substituted moiety is one in which both hydrogens of a methylene (—$CH_2$—) are replaced with an oxygen to form a carbonyl (—CO—).

Substituents can be protected or unprotected as necessary, as known to those skilled in the art or as taught, for example, in Greene, et al., "Protective Groups in Organic Synthesis," John Wiley and Sons, Third Edition, 1999.

As used herein, the term pharmaceutically acceptable salt(s) refers to salts that retain the desired biological activity of the above-identified compounds and exhibit minimal or no undesired toxicological effects. Examples of such salts include, but are not limited to acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid. In another preferred embodiment, the invention comprises the compounds can also be administered as pharmaceutically acceptable quaternary salts known by those skilled in the art, which specifically include the quaternary ammonium salt of the formula —NR+Z-, wherein R is hydrogen, alkyl, or benzyl, and Z is a counter-ion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate). For the purposes of the specification and claims, the term salt is intended to encompass complexes as well.

As employed herein, when a moiety (e.g., cycloalkyl, hydrocarbyl, aryl, heteroaryl, heterocyclic, urea, etc.) is described as "optionally substituted" it is meant that the group optionally has from one to four, preferably from one to three, more preferably one or two, non-hydrogen substituents. Suitable substituents include, without limitation, halo, hydroxy, oxo (e.g., an annular —CH— substituted with oxo is —C(O)—) nitro, halohydrocarbyl, hydrocarbyl, aryl, aralkyl, alkoxy, aryloxy, amino, acylamino, alkylcarbamoyl, arylcarbamoyl, aminoalkyl, acyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups. Preferred substituents, which are themselves not further substituted (unless expressly stated otherwise) are:

(a) halo, cyano, oxo, carboxy, formyl, nitro, amino, amidino, guanidino, (b) $C_1$-$C_5$ alkyl or alkenyl or arylalkyl imino, carbamoyl, azido, carboxamido, mercapto, hydroxy, hydroxyalkyl, alkylaryl, arylalkyl, $C_1$-$C_8$ alkyl, $C_1$-$C_8$ alkenyl, $C_1$-$C_8$ alkoxy, $C_1$-$C_8$ alkoxycarbonyl, aryloxycarbonyl, $C_2$-$C_8$ acyl, $C_2$-$C_8$ acylamino, $C_1$-$C_8$ alkylthio, arylalkylthio, arylthio, $C_1$-$C_8$ alkylsulfinyl, arylalkylsulfinyl, arylsulfinyl, $C_1$-$C_8$ alkylsulfonyl, arylalkylsulfonyl, arylsulfonyl, $C_0$-$C_6$ N-alkyl carbamoyl, $C_2$-$C_{15}$ N,N-dialkylcarbamoyl, $C_3$-$C_7$ cycloalkyl, aroyl, aryloxy, arylalkyl ether, aryl, aryl fused to a cycloalkyl or heterocycle or another aryl ring, $C_3$-$C_7$ heterocycle, $C_5$-$C_{15}$ heteroaryl, or any of these rings fused or spiro-fused to a cycloalkyl, heterocyclyl, or aryl, wherein each of the foregoing is further optionally substituted with one more moieties listed in (a), above; and (c) —$(CH_2)_s$—$NR^{30}R^{31}$, wherein s is from 0 (in which case the nitrogen is directly bonded to the moiety that is substituted) to 6, and $R^{30}$ and $R^{31}$ are each independently hydrogen, cyano, oxo, carboxamido, amidino, $C_1$-$C_8$ hydroxyalkyl, $C_1$-$C_3$ alkylaryl, aryl-$C_1$-$C_3$ alkyl, $C_1$-$C_8$ alkyl, $C_1$-$C_8$ alkenyl, $C_1$-$C_8$ alkoxy, $C_1$-$C_8$ alkoxycarbonyl, aryloxycarbonyl, aryl-$C_1$-$C_3$ alkoxycarbonyl, $C_2$-$C_8$ acyl, $C_1$-$C_8$ alkylsulfonyl, arylalkylsulfonyl, arylsulfonyl, aroyl, aryl, cycloalkyl, heterocyclyl, or heteroaryl, wherein each of the foregoing is further optionally substituted with one more moieties listed in (a), above; or $R^{30}$ and $R^{31}$ taken together with the N to which they are attached form a heterocyclyl or heteroaryl, each of which is optionally substituted with from 1 to 3 substituents from (a), above.

The term "halogen" or "halo" as employed herein refers to chlorine, bromine, fluorine, or iodine. As herein employed, the term "acyl" refers to an alkylcarbonyl or arylcarbonyl substituent. The term "acylamino" refers to an amide group attached at the nitrogen atom (i.e., R—CO—NH—). The term "carbamoyl" refers to an amide group attached at the carbonyl carbon atom (i.e., $NH_2$—CO—). The nitrogen atom of an acylamino or carbamoyl substituent is additionally substituted. The term "sulfonamido" refers to a sulfonamide substituent attached by either the sulfur or the nitrogen atom. The term "amino" is meant to include $NH_2$, alkylamino, arylamino, and cyclic amino groups. The term "ureido" as employed herein refers to a substituted or unsubstituted urea moiety.

The term "radical" as used herein means a chemical moiety comprising one or more unpaired electrons.

A moiety that is substituted is one in which one or more hydrogens have been independently replaced with another chemical substituent. As a non-limiting example, substituted phenyls include 2-flurophenyl, 3,4-dichlorophenyl, 3-chloro-4-fluoro-phenyl, 2-fluoro-3-propylphenyl. As another non-limiting example, substituted n-octyls include 2,4 dimethyl-5-ethyl-octyl and 3-cyclopentyl-octyl. Included within this definition are methylenes (—$CH_2$—) substituted with oxygen to form carbonyl (—CO—).

An "unsubstituted" moiety as defined above (e.g., unsubstituted cycloalkyl, unsubstituted heteroaryl, etc.) means that moiety as defined above that does not have any of the optional substituents for which the definition of the moiety (above) otherwise provides. Thus, for example, while an "aryl" includes phenyl and phenyl substituted with a halo, "unsubstituted aryl" does not include phenyl substituted with a halo.

Preferred embodiments of a particular genus of compounds of the invention include combinations of preferred embodiments.

As used herein, the term pharmaceutically acceptable salt(s) refers to salts that retain the desired biological activity of the above-identified compounds and exhibit minimal or no undesired toxicological effects. Examples of such salts include, but are not limited to acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid. The compounds can also be administered as pharmaceutically acceptable quaternary salts known by those skilled in the art, which specifically include the quaternary ammonium salt of the formula —NR+Z-, wherein R is hydrogen, alkyl, or benzyl, and Z is a counter-ion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

The active compound is included in the pharmaceutically acceptable carrier or diluent in an amount sufficient to deliver to a patient a therapeutically effective amount without causing serious toxic effects in the patient treated. The term "therapeutically effective amount" is meant to denote a dosage sufficient to inhibit proliferation of the virus in the patient. A preferred dose of the active compound for all of the above-mentioned conditions is in the range from about 0.01 to 300 mg/kg, preferably 0.1 to 100 mg/kg per day, more generally 0.5 to about 25 mg per kilogram body weight of the recipient per day. A typical topical dosage will range from 0.01-3% wt/wt in a suitable carrier. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

The compound is conveniently administered in any suitable unit dosage form, including but not limited to one containing 1 to 3000 mg, preferably 5 to 500 mg of active ingredient per unit dosage form. An oral dosage of 1-500, preferably 10-250, more preferably 25-250 mg is usually suitable.

The active ingredient should be administered to achieve peak plasma concentrations of the active compound of about 0.001-30 μM, preferably about 0.01-10 μM. This may be achieved, for example, by the intravenous injection of a solution or formulation of the active ingredient, optionally in saline, or an aqueous medium or administered as a bolus of the active ingredient.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterores; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials that modify the physical form of the dosage unit, for example, coatings of sugar, shellac, or enteric agents. See generally "Remington's Pharmaceutical Sciences," Mack Publishing Co., Easton, Pa.

The active compound or pharmaceutically acceptable salt thereof can be administered as a component of an elixir, suspension, syrup, wafer, chewing gum or the like. Syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as antibiotics, antifungals, other anti-inflammatories, or antiviral compounds.

Solutions or suspensions used for parenteral, intradermal, subcutaneous, or topical application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylacetic acid. Methods for preparation of such formulations will be apparent to those skilled in the art. The materials can also be obtained commercially from Alza Corporation (CA) and Gilford Pharmaceuticals (Baltimore, Md.). Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidylcholine, arachadoyl phosphatidylcholine, and cholesterol) in an inorganic solvent that is then evaporated, leaving behind a thin film of dried lipid on the surface of the container. Aqueous solutions of the active compound or its monophosphate, diphosphate, and/or triphosphate derivatives are then introduced into the container. The container is then swirled by hand to free lipid material from the sides of the container and to disperse lipid aggregates, thereby forming the liposomal suspension.

Synthesis

The compounds of the invention can be synthesized according to the schemes presented below using methods well known to those skilled in the art. For example, methods that can be used to make the compounds of the invention are described in Shehata et al., Monatshefte fur Chemie 121: pp 1017-1021 and Meth-Cohn et al., J. C. S. Perkin I: pp 2509-2517, both of which are incorporated by reference in their entirety. One skilled in the art will recognize that the substituents of the starting compound 1 can be varied using well known synthetic procedures. For example, various types of substitution reactions can take place on the phenyl group of compound 1 to give the alkoxy, alkyl, haloalkyl, or sulfonylalkyl product. Similarly, various types of substitution reactions or condensation reactions on any of the species in Scheme 1 will result in the various compounds described in this invention. For example, compound 5 can be reacted with any suitable amine instead of $H_2N$—OTHP.

Scheme I

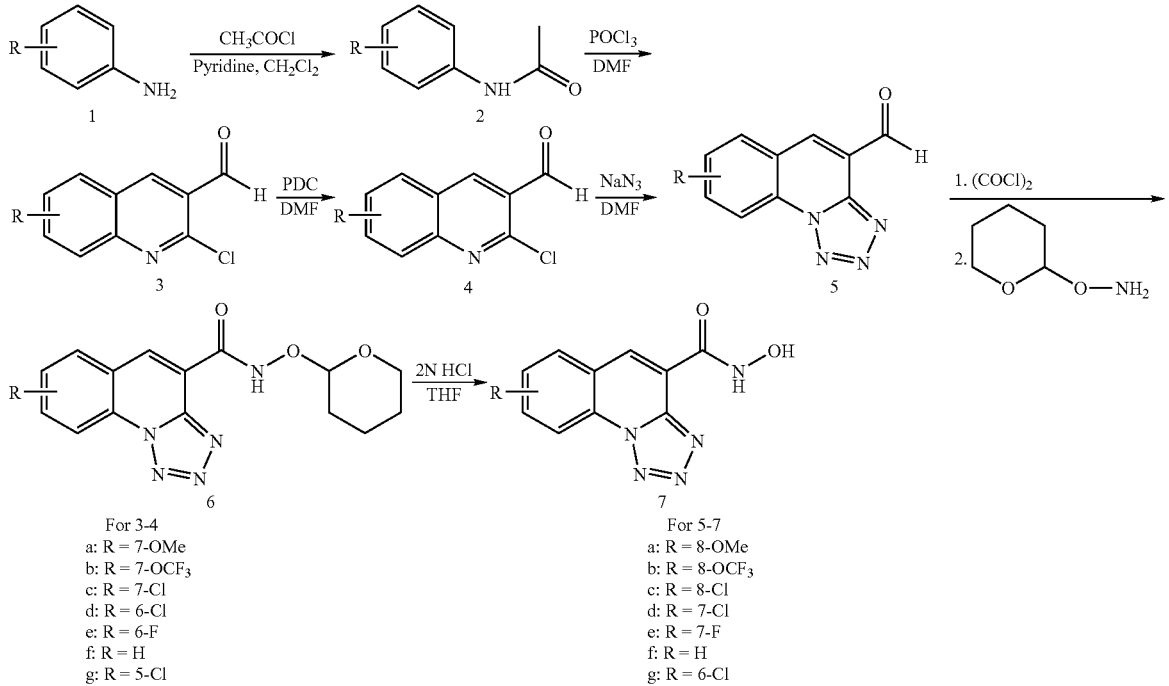

For 3-4
a: R = 7-OMe
b: R = 7-OCF$_3$
c: R = 7-Cl
d: R = 6-Cl
e: R = 6-F
f: R = H
g: R = 5-Cl

For 5-7
a: R = 8-OMe
b: R = 8-OCF$_3$
c: R = 8-Cl
d: R = 7-Cl
e: R = 7-F
f: R = H
g: R = 6-Cl

Representative procedure for the preparation of 2,7-dichloroquinoline-3-carboxaldehyde (3c): To a dry reaction flask equipped with a reflux condenser, a magnetic stirring bar and a rubber septum with a N$_2$ inlet was placed 3-chloroacetanilide (2, 8.45 g, 50 mmol) and POCl$_3$ (34 mL, 365 mmol). The reaction mixture was cooled to 0° C. and to it was added DMF (10.5 mL, 135 mmol) over a period of 20 minutes. It was stirred at that temperature for 1 h and then at 65-75° C. for 24 h. The resulting slurry was cooled to room temperature, poured over a crushed-ice (1 Kg), digested for 1 h, the resulting solid was filtered, washed well with water and dried to give 5.26 g (47%) of the desired 2,7-dichloroquinoline-3-carboxaldehyde (3c). $^1$H NMR (CDCl$_3$, 300 MHz): δ 10.54 (s, 1H), 8.74 (s, 1H), 8.07 (d, 1H, J=2.1 Hz), 7.93 (d, 1H, J=9.0 Hz), 7.61 (dd, 1H, J=2.4 and 8.7 Hz); LCMS (m/z): 226 (M$^+$).

Representative procedure for the preparation of 2,7-dichloroquinoline-3-carboxylic acid (4c): A dry reaction flask equipped with a magnetic stirring bar and a rubber septum was charged with 2,7-dichloroquinoline-3-carboxaldehyde (3c, 1.1 g, 5 mmol), PDC (3.76 g, 10 mmol) and dry DMF (5 mL) and stirred at room temperature for 24 h. The reaction mixture was diluted with water (500 mL), filtered, the filtrate was saturated with NaCl and the resulting aqueous solution was extracted with EtOAc (3×200 mL). The EtOAc extract was dried over anhydrous Na$_2$SO$_4$ and solvent was removed to give 1.02 g (85%) of the desired 2,7-dichloroquinoline-3-carboxylic acid (4c). TLC Rf: 0.12 (20% MeOH/EtOAc); $^1$H NMR (acetone d$_6$, 300 MHz): 8.96 (s, 1H); 8.22 (d, 1H, J=9.0 Hz), 8.04 (d, 1H, J=1.8 Hz), 7.97 (bs, 1H), 7.74 (dd, 1H, J=1.8 and 8.7 Hz); LCMS (m/z): 241 (MH$^+$).

Representative procedure for the preparation of 8-chlorotetrazolo[1,5-a]quinoline-4-carboxylic acid (5c): To a dry reaction vial with a screw cap was placed 2,7-dichloroquinoline-3-carboxylic acid (0.241 g, 1 mmol), sodium azide (0.078 g, 1.2 mmol) and dry DMF (3 mL) and shaken at 65-75° C. for a period of 24 h. The reaction mixture was diluted with water (100 mL), saturated with NaCl, the resulting solid was filtered and dried to give 0.100 g (41%) of the carboxytetrazole 5c. TLC Rf: 0.06 (20% MeOH/EtOAc); $^1$H NMR (DMSO d$_6$+CDCl$_3$, 300 MHz): δ 8.71 (bs, 1H), 8.60 (s, 1H), 8.30 (d, 1H, J=7.8 Hz), 7.79 (d, 1H, J=7.5 Hz); LCMS (m/z): 249 (MH$^+$).

Representative procedure for the preparation of 8-chloro-N-(tetrahydro-2H-pyran-2-yloxy)tetrazolo[1,5-a]quinoline-4-carboxamide (6c): To a suspension of carboxytetrazole (5c, 0.05 g, 0.2 mmol) in CH$_2$Cl$_2$ (5 mL) at 0° C. under N$_2$ was added DMF (4-drops) followed by (COCl)$_2$ (1M CH$_2$Cl$_2$, 0.15 mL, 0.3 mmol) and the reaction was stirred for 1 h. The reaction solvent was removed and the resulting residue of acid chloride was dried under high vacuum. The acid chloride was then suspended in CH$_2$Cl$_2$ (5 mL), cooled to 0° C., to it was added pyridine (0.033 mL, 0.4 mmol) followed by H$_2$N—OTHP (0.035 g, 0.3 mmol) and stirred at room temperature for 24 h. The CH$_2$Cl$_2$ solution was washed with water, dried and solvent was evaporated. The resulting residue was filtered through a pad of silica gel to obtain the requisite oxamic acid ester 6c. $^1$H NMR (CDCl$_3$, 300 MHz): δ 11.58 (s, 1H), 8.92 (s, 1H), 8.74 (d, 1H, J=1.8 Hz), 8.10 (d, 1H, J=8.1 Hz), 7.77 (dd, 1H, J=1.8 Hz and 8.7 Hz), 5.26 (m, 1H), 4.15 (m, 1H), 3.76 (m, 1H), 2.10-1.50 (m, 6H); LCMS (m/z): 347 (MH$^+$).

Representative procedure for the preparation of 8-chloro-N-hydroxytetrazolo[1,5-a]quinoline-4-carboxamide (7c): To a solution of THP oxamate 6c (0.035 g, 0.1 mmol) in THF (1 mL) was added 2N HCl (1 mL) and stirred at room temperature for 6 h. The reaction solvent was removed under a reduced pressure and the resulting aqueous solution was diluted with water. The precipitated solid was filtered, washed with water and dried to give the desired oxamic acid 7c. $^1$H NMR (CDCl$_3$, 300 MHz): δ 8.80 (s, 1H), 8.64 (bd, 1H), 8.06 (d, 1H, J=8.1 Hz), 7.70 (dd, 1H, J=2.4 and 8.7 Hz), LCMS (m/z): 264 (MH$^+$).

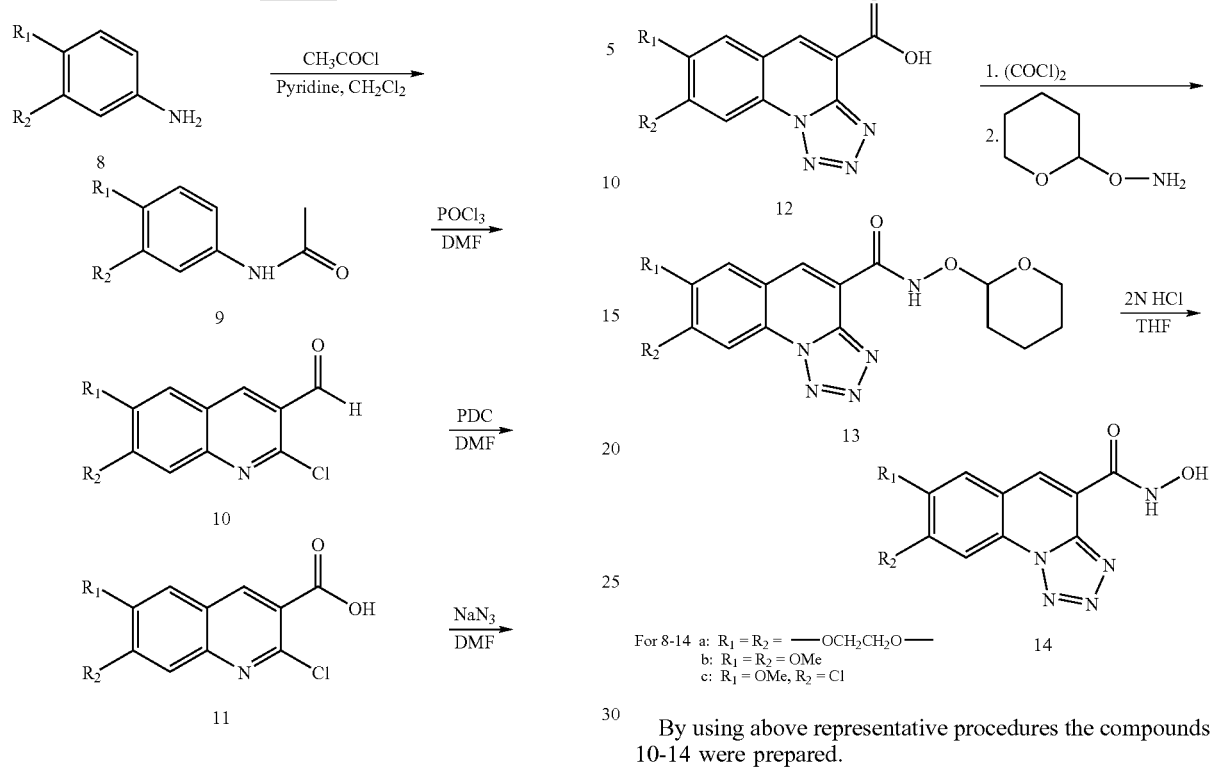
By using above representative procedures the compounds 10-14 were prepared.
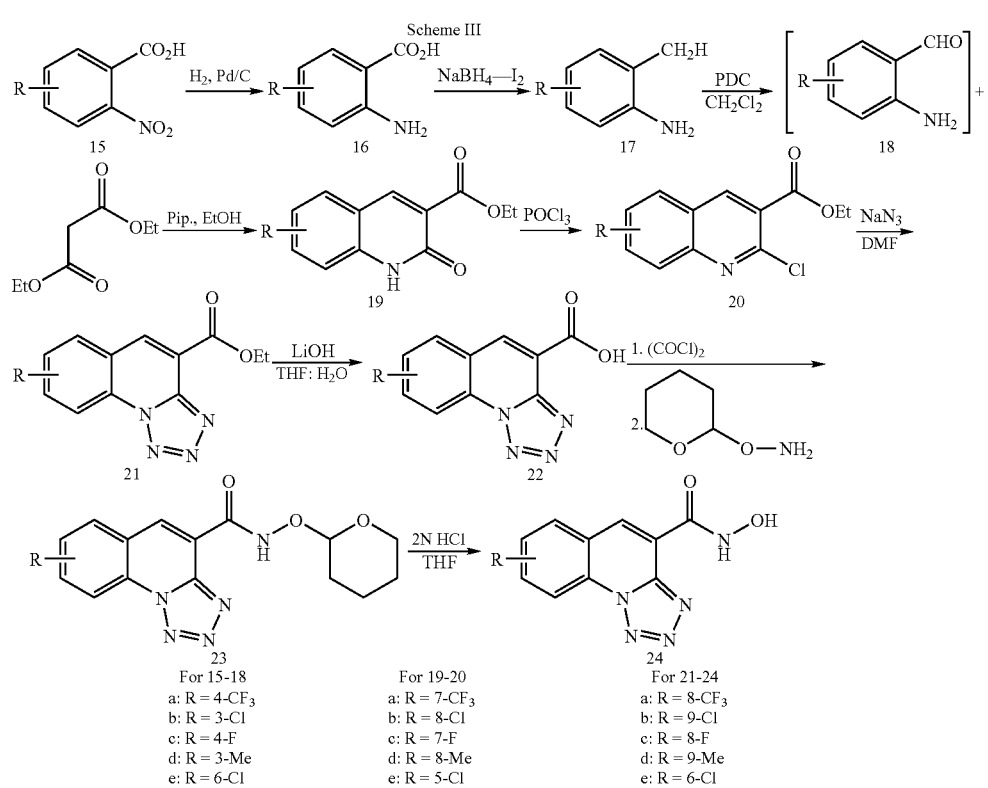

Representative procedure for the preparation of 2-amino-4-(trifluoromethyl)benzylalcohol (17a): To a suspension of anthranilic acid 16a (2.04 g, 10 mmol), NaBH$_4$ (0.912 g, 24 mmol) in THF (10 mL) under N$_2$ at 0° C. was added I$_2$ (2.54 g, 10 mmol) solution in THF (10 mL) over a period of 10-15 minutes. The resulting reaction mixture was stirred at room temperature for 30 minutes and then at reflux for 24 h. The reaction mixture was cooled to room temperature and MeOH was added very slowly to the mixture till the clear solution was formed. The solvent was removed and the residue was stirred with 20% KOH (20 mL) at room temperature for 4 h, extracted with CH$_2$Cl$_2$ (3×100 mL), dried (Na$_2$SO$_4$) and solvent was removed to obtain 1.91 g (100%) of the requisite alcohol 17a. $^1$H NMR (CDCl$_3$, 300 MHz): δ 7.15 (d, 1H, J=7.5 Hz), 6.94 (d 1H, J=7.5 Hz), 6.91 (s, 1H), 4.71 (s, 2H).

Representative procedure for the preparation of 2-amino-4-(trifluoromethyl)benzaldehyde (18a): A dry reaction flask equipped with a stirring bar and a rubber septum was charged with 2-amino-4-(trifluoromethyl)benzylalcohol (17a, 1.91 g, 10 mmol), PDC (4.51 g, 12 mmol) and CH$_2$Cl$_2$ (20 mL). The resulting mixture was stirred at room temperature for 4 h, diluted with CH$_2$Cl$_2$ (100 mL), filtered through a small pad of celite. The combined filtrate was concentrated and dried to provide 1.54 g (81%) of the desired amino aldehyde 18a. $^1$H NMR (CDCl$_3$, 300 MHz): δ 9.94 (s, 1H), 7.61 (d, 1H, J=7.5 Hz), 6.95 (d, 1H, J=8.4 Hz), 6.91 (s, 1H).

Representative procedure for the preparation of ethyl 7-(trifluoromethyl)-2-quinolone-3-carboxylate (19a): A dry reaction flask was charged with aldehyde 18a (1.54 g, 8.14 mmol), diethyl malonate (12.73 mL, 81.4 mmol), piperidine (3.22 mL, 32.59 mmol) and EtOH (25 mL). The resulting mixture was refluxed for 24 h, concentrated, diluted with n-hexanes (100 mL) and the product was allowed to precipitate. The desired product was filtered, washed with additional amount of n-hexanes and dried to give 0.738 g (32%) of the 2-quinolone 19a. $^1$H NMR (CDCl$_3$, 300 MHz): δ 8.58 (s, 1H), 7.81 (d, 1H, J=8.7 Hz), 7.67 (s, 1H), 7.49 (d, 1H, J=8.1 Hz), 4.47 (q, 2H, J=7.2 Hz), 1.47 (t, 3H, J=7.5 Hz).

Representative procedure for the preparation of ethyl 2-chloro-7-(trifluoromethyl)quinoline-3-carboxylate (20a): To a dry reaction flask was placed quinolone 19a (1 g, 3.5 mmol), POCl$_3$ (7 mL) and heated at 80-90° C. for 24 h. The reaction mixture cooling to room temperature was poured over crushed ice, digested for 1 h, saturated with NaCl and 0.948 g (89%) of the desired product was isolated by filtration and flash chromatography (silica gel, 10% EtOAc/Hex). $^1$H NMR (CDCl$_3$, 300 MHz): δ 8.70 (s, 1H), 8.37 (s, 1H), 8.04 (d, 1H, J=8.7 Hz), 7.80 (dd, 1H, J=1.5 and 8.7 Hz), 4.50 (q, 2H, J=7.2 Hz), 1.47 (t, 3H, J=6.9 Hz), LCMS (m/z): 304 (MH$^+$).

Representative procedure for the preparation of ethyl 8-(trifluoromethyl)tetrazolo[1,5-a]quinoline-4-carboxylate (21a): A dry reaction flask was charged with ethyl 2-chloro-7-(trifluoromethyl)quinoline-3-carboxylate (20a, 0.065 g, 0.21 mmol), NaN$_3$ (0.017 g, 0.26 mmol) and DMF (1.5 mL), and heated at 65-75° C. for 8 h. The resulting mixture was poured over water (100 mL), saturated with NaCl, the solid obtained was filtered, washed with water and dried to give 0.038 g (58%) the desired compound (21a). $^1$H NMR (CDCl$_3$, 300 MHz): δ 9.04 (s, 1H), 8.79 (s, 1H), 8.27 (d, 1H, J=8.1 Hz), 8.02 (bd, 1H, J=8.4 Hz), 4.63 (q, 2H, J=7.2 Hz), 1.54 (t, 3H, J=7.2 Hz); LCMS (m/z): 311 (MH$^+$).

Representative procedure for the preparation of 8-(trifluoromethyl)tetrazolo[1,5-a]quinoline-4-carboxylic acid (22a): A suspension of 21a (0.03 g, 0.1 mmol) and LiOH.H$_2$O (0.021 g, 0.5 mmol) in THF: H$_2$O (1:1, 2 mL) was stirred at room temperature for 3 h, concentrated, diluted with water and filtered. The filtrate upon acidification (cold 2N HCl) gave the solid, which was filtered and dried to afford 0.02 g (71%) of the desired product 22a. $^1$H NMR (CD$_3$OD+CDCl$_3$, 300 MHz): δ 8.99 (s, 1H), 8.81 (s, 1H), 8.25 (d, 1H, J=9.0 Hz), 7.98 (bd, 1H, J=6.9 Hz); LCMS (m/z): 282 (MH$^+$).

Compounds 23-24 were prepared by using above representative procedures of compounds 6 and 7.

By using above representative procedures the compounds 26-33 were prepared.

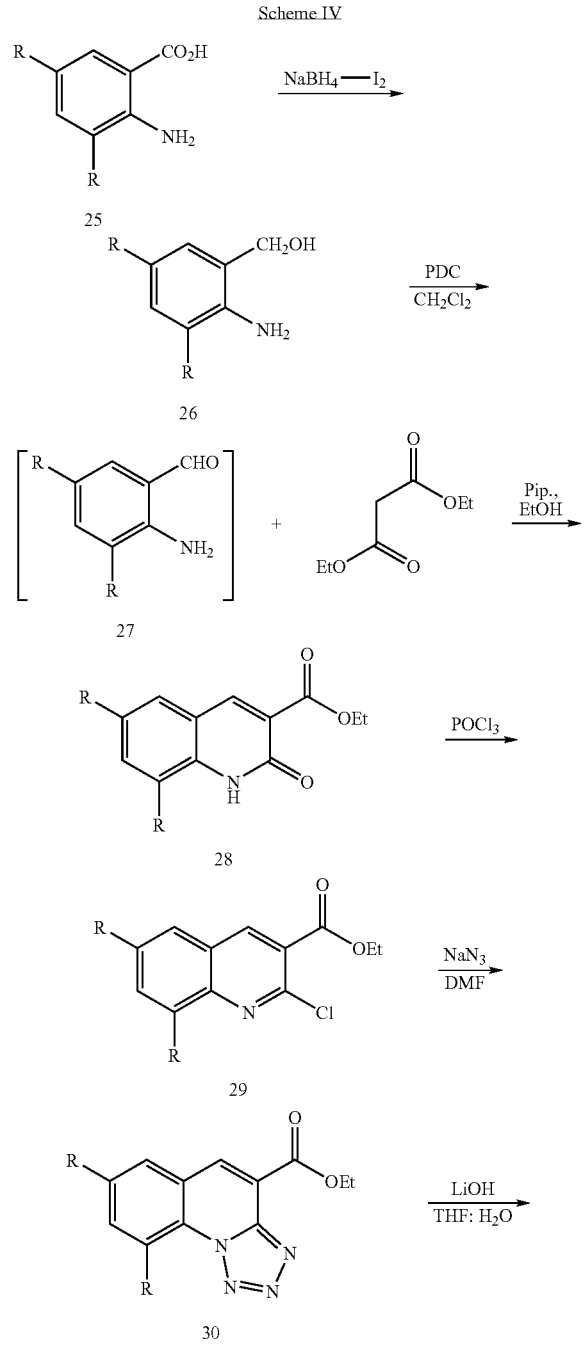

Scheme IV

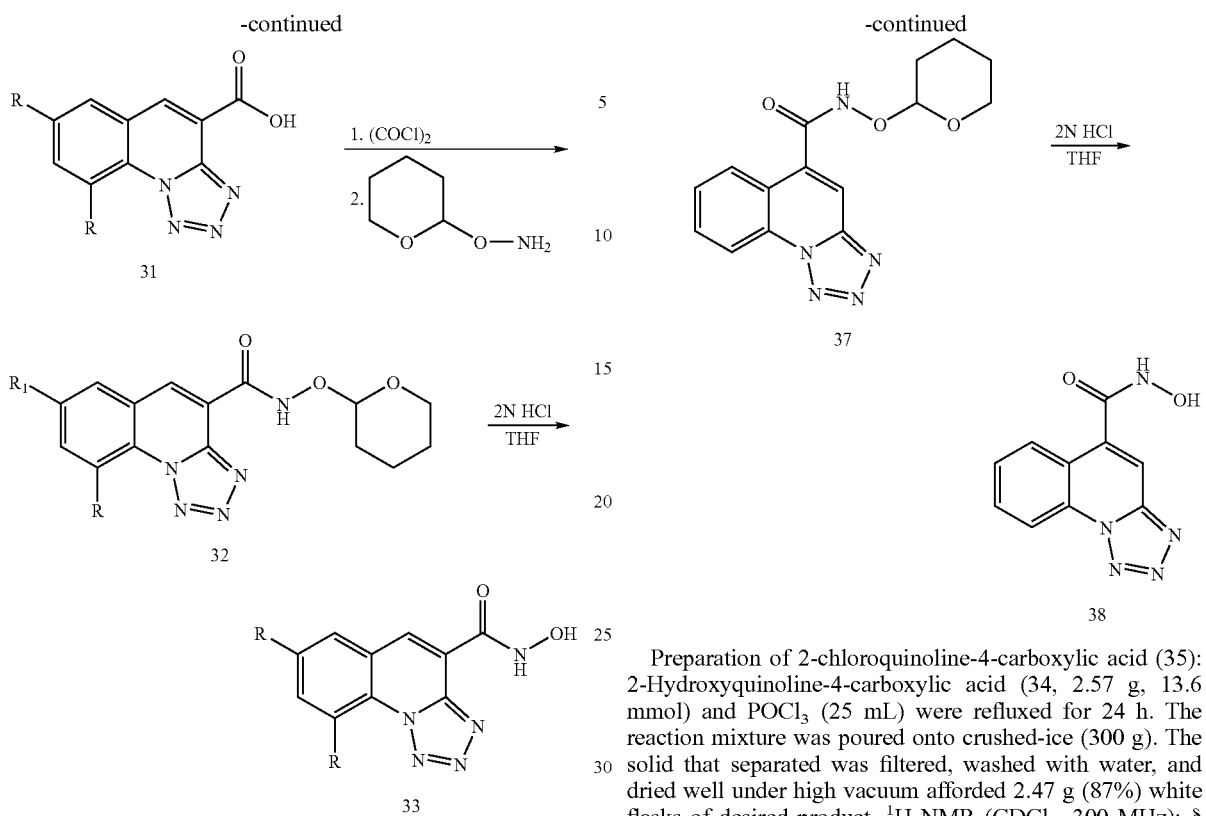
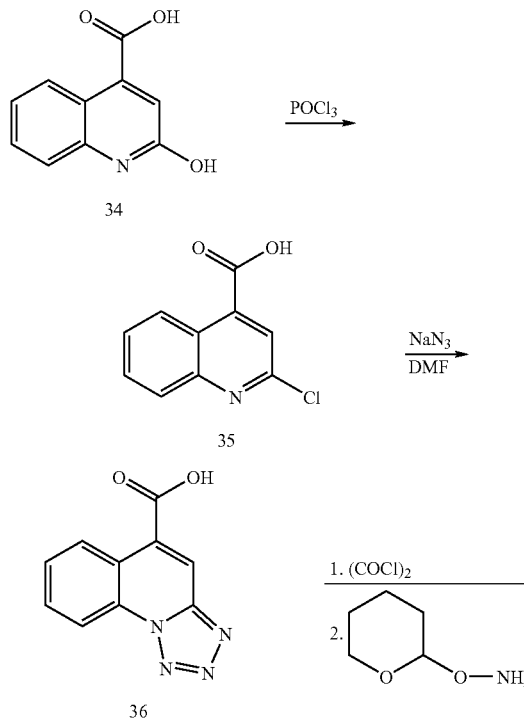

Preparation of 2-chloroquinoline-4-carboxylic acid (35): 2-Hydroxyquinoline-4-carboxylic acid (34, 2.57 g, 13.6 mmol) and $POCl_3$ (25 mL) were refluxed for 24 h. The reaction mixture was poured onto crushed-ice (300 g). The solid that separated was filtered, washed with water, and dried well under high vacuum afforded 2.47 g (87%) white flasks of desired product. $^1$H NMR (CDCl$_3$, 300 MHz): δ 8.67 (d, 1H, J=8.4 Hz), 7.91 (d, 1H, J=8.1 Hz), 7.83 (s, 1H), 7.76 (t, 1H, J=7.2 Hz), 7.54 (t, 1H, J=7.2 Hz); LCMS (m/z): 208 (MH$^+$).

Compounds 36-38 were prepared by using above representative procedures of compounds 5-7.

Preparation of 8-chloro-N-methyl-N-(tetrahydro-2H-pyran-2-yloxy)tetrazolo[1,5-a]quinoline-4-carboxamide (46): Compound 6c (65 mg, 0.19 mmol) was dissolved in dry DMF (1.0 mL), Cs$_2$CO$_3$ (121 mg, 0.37 mmol) was added, stirred at room temperature for 15 minutes and then dimethylsulfate (21 µl) was added. The reaction mixture was stirred at room temperature for 24 h, poured into water, left aside for 1 h, the solid that separated was filtered, dried to provide 32 mg (47%) of desired product as colorless liquid. $^1$H NMR (CDCl$_3$, 300 MHz): δ 8.66 (s, 1H), 8.25 (s, 1H), 7.93 (d, 1H, J=8.4 Hz), 7.67 (dd, 1H, J=2.1 and 8.5 Hz), 5.36 (t, 1H, J=3.6 Hz), 4.26 (s, 3H), 3.97 (m, 1H), 3.70 (m, 1H), 1.90 (m, 3H), 1.66 (m, 3H); LCMS (m/z): 278 (M-84).

Compound 47 was prepared by using above representative procedure of compound 7.

Scheme VII

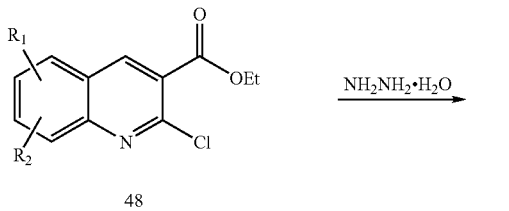

48

For 48-49 a: R$_1$ = 6-Cl, R$_2$ = 8-Cl
b: R$_1$ = 7-F, R$_2$ = H
c: R$_1$ = 6-Cl, R$_2$ = H

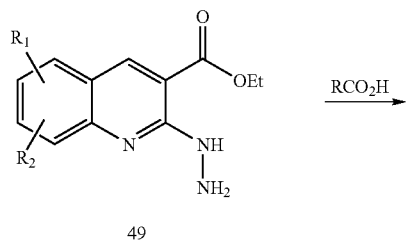

49

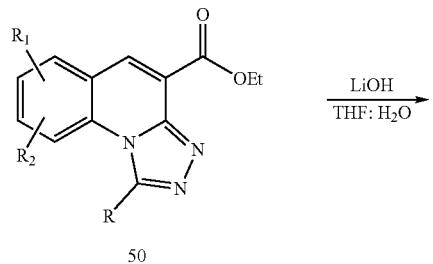

50

For 50-51 a: R$_1$ = 7-Cl, R$_2$ = 9-Cl, R = H
b: R$_1$ = 8-F, R$_2$ = H, R = H
c: R$_1$ = 7-Cl, R$_2$ = H, R = H
d: R$_1$ = 7-Cl, R$_2$ = H, R = CH$_3$

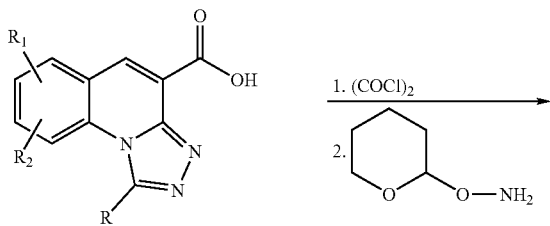

51

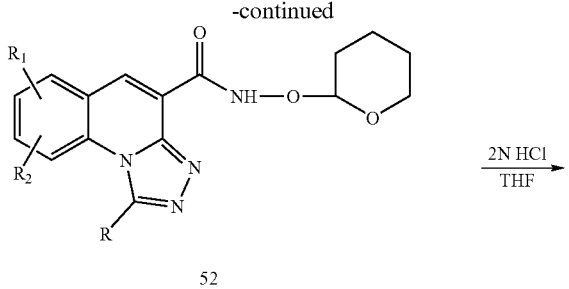

52

For 52-53 a: R$_1$ = 7-Cl, R$_2$ = 9-Cl, R = H
b: R$_1$ = 8-F, R$_2$ = H, R = Cl
c: R$_1$ = 7-Cl, R$_2$ = H, R = H
d: R$_1$ = 7-Cl, R$_2$ = H, R = CH$_3$

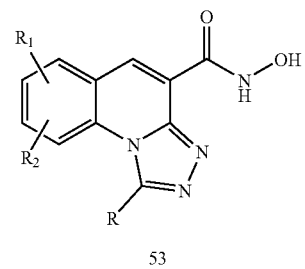

53

Representative procedure for the preparation of ethyl 6,8-dichloro-2-hydrazinoquinoline-4-carboxylate (49a): To a warm (40° C.) solution of compound 48a (0.6848 g, 2.26 mmol) in ethanol (100 mL) was added hydrazine hydrate (0.11 mL, 2.26 mmol) and heated at 40° C. for over-night. Again hydrazine hydrate (0.11 mL, 2.26 mmol) was added and stirred at that temperature for 24 h. The reaction mixture was concentrated, absorbed on a minimum amount of silica gel and chromatographed (silical gel, flash, n-hexanes 10% to 20% to 50% EtOAc) to afford 0.5765 g (85%) of desired product as colorless solid. $^1$H NMR (CDCl$_3$, 300 MHz): δ 8.89 (s, 1H), 8.51 (s, 1H), 7.70 (s, 1H), 7.55 (s, 1H), 4.40 (q, 2H, J=7.2 Hz), 4.35 (br s, 2H), 1.43 (t, 3H, J=7.2 Hz); LCMS (m/z): 300 (MH$^+$).

Representative procedure for the preparation of ethyl 7,9-dichloro-s-triazolo[4,3-a]quinoline-4-carboxylate (50a): Compound 49a (0.288 g, 0.96 mmol) and formic acid (5 mL) were refluxed for 24 h. The reaction mixture was diluted with water (50 mL), neutralized with solid sodium bicarbonate. The solid was filtered, washed with water and dried well to afford 0.2783 g (93%) of desired product as colorless solid. $^1$H NMR (CDCl$_3$, 300 MHz): δ 10.29 (s, 1H), 8.22 (s, 1H), 7.85 (m, 2H), 4.57 (q, 2H, J=6.9 Hz), 1.50 (t, 3H, J=7.2 Hz); LCMS (m/z): 309 (MH$^+$).

Compounds 51-53 were prepared by using above representative procedures of compounds 22a and 6-7.

Abbreviations and acronyms used in the examples include: POCl$_3$, phosphorus oxychloride; PDC, pyridium dichromate; CH$_2$Cl$_2$, dichloromethane; DMF, N,N-dimethylformamide; I$_2$, iodine; EtOAc, ethyl acetate; EtOH, ethyl alcohol; h, hour; LiOH.H$_2$O, lithium hydroxide monohydrate; HPLC, high performance liquid chromatography; LCMS, liquid chromatography mass spectrum (using HPLC); ether, diethyl ether; MeOH, methanol; Na$_2$SO$_4$, sodium sulfate; Cs$_2$CO$_3$, cesium carbonate; NaN$_3$, sodium azide; KOH, potassium hydroxide; NaOH, sodium hydroxide; NaBH$_4$, sodium borohydride; NMR, nuclear magnetic resonance spectroscopy; (COCl)$_2$, oxalyl chloride; hex, hexanes; NaCl, sodium chloride; THF, tetrahydrofuran; TLC, thin layer chromatography Biological Assay The following assay examples illustrate the HCV inhibitory properties of the compounds of the invention.

ASSAY EXAMPLE 1

HCV Replicon Assay

Actively dividing 5-2Luc replicon cells were seeded at the density of 5000-7500 cells/well in the volume of 90 μl/well into 96 well plate(s). The cells were then incubated at 37° C. and 5% $CO_2$ for 24 hours. The 5-2 cells are replicon cells licensed from Ralf Bartenschlager (Germany) and have a self-replicating RNA molecule in the Huh7 cell; the RNA contains HCV non-structural proteins that make the self-replication possible.

Various concentrations of compounds (in the volume of 10 μl) were added into each well 24 hours after seeding the cells. The cells were incubated for another 24 hours before luciferase assay.

After incubating the 5-2 Luc replicon cells with the compounds for 24 hours, media were aspirated from each well and Bright-Glo (Pharmacia) luciferase assay reagents were added to each well according to the manufacturer's manual. Briefly, the Bright-Glo reagent was diluted with equal volume of PBS and an aliquote (100 μl) was added to each well. After incubating the plate at room temperature for 5 minutes, luciferase counts were taken using a luminometer.

ASSAY EXAMPLE 2

Luciferase Counter Assay

Actively dividing CMV-Luc cells (Luc cells in which DNA construct (CMV promoter followed by Luciferase gene) is permanently integrated into the chromosome of Huh7 cells) were seeded at the density of 5000-7500 cells/well in the volume of 90 μl/well into 96 well plate(s). The cells were then incubated at 37° C. and 5% $CO_2$ for 24 hours.

Various concentrations of compounds (in the volume of 10 μl) were added into each well 24 hours after seeding the cells. The cells were incubated with the compounds for another 24 hours before luciferase assay.

After incubating the CMV-Luc cells with the compounds for 24 hours, media were aspirated from each well and Bright-Glo (Pharmacia) luciferase assay reagents were added to each well according to the manufacturer's manual. Luciferase counts were taken using a luminometer.

The activity of a number of compounds according to the invention measured by the luciferase assay is displayed in Table 1.

ASSAY EXAMPLE 3

Immunoblotting Assay

Actively dividing 9-13 replicon cells (Huh7 cells comprising an HCV replicon) were seeded at the density of $1\times10^5$ cells/well in the volume of 2 ml/well into 6 well plate(s). The cells were then incubated at 37° C. and 5% $CO_2$ for 24 hours.

Various concentrations of compounds (in the volume of 10 μl) were added into each well 24 hours after seeding the cells. The cells were incubated with the compounds for another 48 hours.

Protein samples were prepared from the cultured cells and resolved on a SDS-PAGE gel.

After electrophoresis, the protein samples on the SDS-PAGE gel were transferred to a nitrocellulose membrane.

The membrane was blocked with 5% non-fat milk in PBS for 1 hr at room temperature.

Primary antibody incubation was performed for 1 hour at room temperature before the membrane was washed for 3 times with PBST (PBS plus 0.1% Tween 20), 15 minutes each.

Horse Radish Perpxidase conjugated secondary antibody incubation was performed for 1 hour at room temperature before the membrane was washed for 3 times with PBST (PBS plus 0.1% Tween 20), 15 minutes each.

The membrane was then soaked in substrate solution (Pierce) and exposed to a film.

ASSAY EXAMPLE 4

TaqMan RT-PCR Assay

Actively dividing 9-13 replicon cells were seeded at the density of $3\times10^4$ cells/well in the volume of 1 ml/well into 24 well plate(s). The cells were then incubated at 37° C. and 5% $CO_2$ for 24 hours.

Various concentrations of compounds (in the volume of 10 μl) were added into each well 24 hours after seeding the cells. The cells were incubated with the compounds for another 24 hours.

After incubating the 9-13 replicon cells with the compounds for 24 hours, media were aspirated off and RNA samples were prepared from each well.

TaqMan® (Roche Molecular Systems) one step RT-PCR was performed using the RNA samples according to the manufacturer's manual. Briefly, properly diluted RNA sample, upstream primer, downstream primer, FAM-labeled probe oligo were mixed and water was added to make up the volume to 25 μl. Equal volume of 2× TaqMan Master Mix were added and the reaction was performed in an ABI Prism 7700 Sequence Detector (Applied Biosystems).

The compounds in Table 1 to 3 immediately below were prepared essentially using the methods described herein and illustrated in the schemes. All of the compounds in this application were named using Chemdraw Ultra version 6.0.2, which is available through Cambridgesoft.co, 100 Cambridge Park Drive, Cambridge, Mass. 02140, Namepro version 5.09, which is available from ACD labs, 90 Adelaide Street West, Toronto, Ontario, M5H, 3V9, Canada, or were derived therefrom.

The compounds of Table 1 below exhibited greater than 20% inhibitory activity.

TABLE 1

| Structure | Name |
|---|---|
| 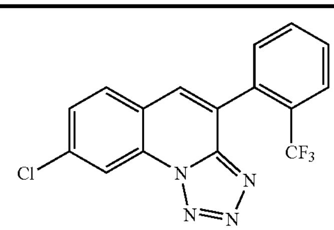 | 8-chloro-4-[2-(trifluoromethyl)phenyl]tetrazolo[1,5-a]quinoline |

TABLE 1-continued

| Structure | Name |
|---|---|
| 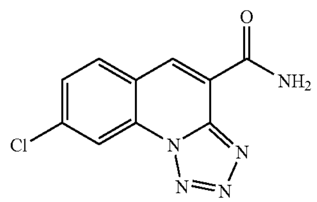 | 8-chlorotetrazolo[1,5-a]quinoline-4-carboxamide |
| 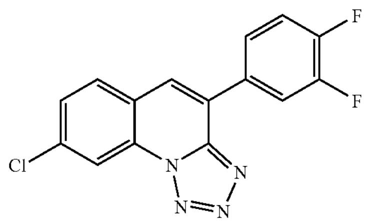 | 8-chloro-4-(3,4-difluorophenyl)tetrazolo[1,5-a]quinoline |
| 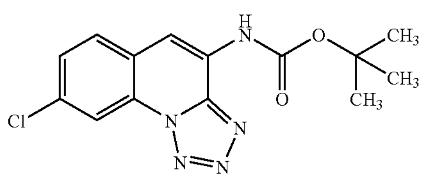 | tert-butyl(8-chlorotetrazolo[1,5-a]quinolin-4-yl)carbamate |
| 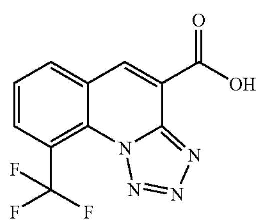 | 9-(trifluroomethyl)tetrazo[1,5-a]quinoline-4-carboxylic acid |
| | 9-chloro-N-iso-butoxytetrazolo[1,5-a]quinoline-4-carboxamide |
| 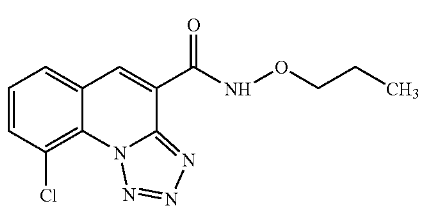 | 9-chloro-N-propoxytetrazolo[1,5-a]quinoline-4-carboxamide |
| | 9-chloro-N-iso-propoxytetrazolo[1,5-a]quinoline-4-carboxamide |

TABLE 1-continued

| Structure | Name |
|---|---|
| 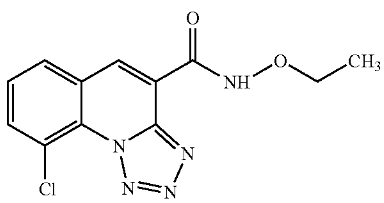 | 9-chloro-N-ethoxytetrazolo[1,5-a]quinoline-4-carboxamide |
| 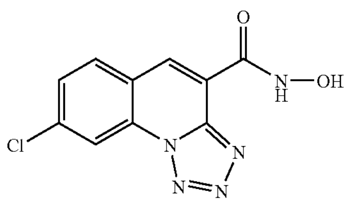 | 8-chloro-N-hydroxytetrazolo[1,5-a]quinoline-4-carboxamide |

The compounds of Table 2 exhibited 5% to 20% inhibitory activity.

TABLE 2

| Structure | Name |
|---|---|
| 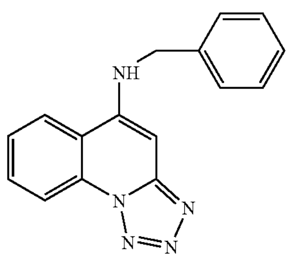 | N-benzyltetrazolo[1,5-a]quinolin-5-amine |
| 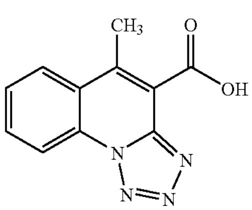 | 5-methyltetrazolo[1,5-a]quinoline-4-carboxylic acid |
| 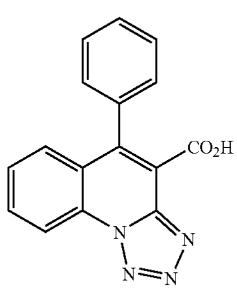 | 5-phenyltetrazolo[1,5-a]quinoline-4-carboxylic acid |

TABLE 2-continued

| Structure | Name |
|---|---|
| | 8-chloro-4-(pyridin-2-yl-sulfonyl)tetrazolo[1,5-a]quinoline |
| | 2-(8-chlorotetrazolo[1,5-a]quinolin-4-yl)benzonitrile |
| | 8-(cyclopentyloxy)tetrazolo[1,5-a]quinoline-4-carbaldehyde |
| | 8-chloro-7-methoxytetrazolo[1,5-a]quinoline-4-carbaldehyde |
| | 8-chloro-7-methoxytetrazolo[1,5-a]quinoline-4-carboxylic acid |
| | tetrazolo[1,5-a]quinoline-4-carboxamide |
| | N-hydroxytetrazolo[1,5-a]quinoline-4-carboximidamide |
| | tetrazolo[1,5-a]quinoline-4-carboximidamide |

TABLE 2-continued

| Structure | Name |
|---|---|
| 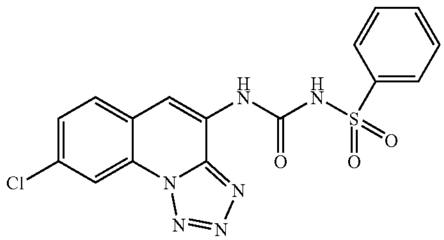 | N-{[(8-chlorotetrazolo[1,5-a]quinolin-4-yl)amino]carbonyl}benzenesulfonamide |
| 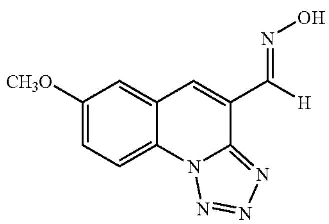 | 7-methoxytetrazolo[1,5-a]quinoline-4-carbaldehyde oxime |
| 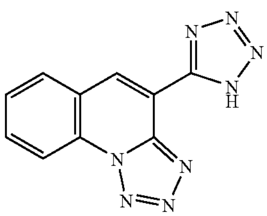 | 4-(1H-tetrazol-5-yl)tetrazolo[1,5-a]quinoline |
| 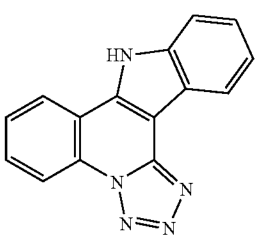 | 9H-indolo[3,2-c]tetrazolo[1,5-a]quinoline |
| 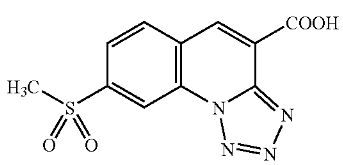 | 8-(methylsulfonyl)tetrazolo[1,5-a]quinoline-4-carboxylic acid |
| 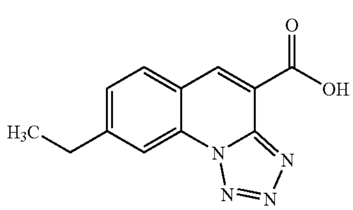 | 8-ethyltetrazolo[1,5-a]quinoline-4-carboxylic acid |
| 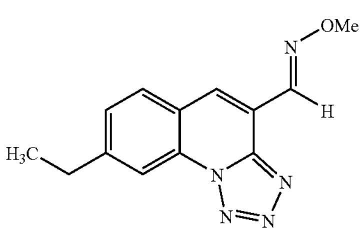 | 8-ethyltetrazolo[1,5-a]quinoline-4-carbaldehyde O-methyloxime |

TABLE 2-continued

| Structure | Name |
|---|---|
| 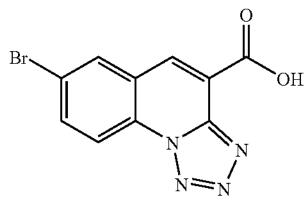 | 7-bromotetrazolo[1,5-a]quinoline-4-carboxylic acid |
| 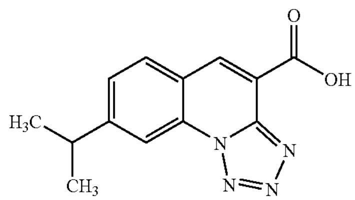 | 8-isopropyltetrazolo[1,5-a]quinoline-4-carboxylic acid |
| 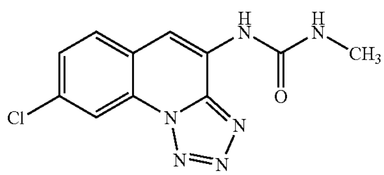 | N-(8-chlorotetrazolo[1,5-a]quinolin-4-yl)-N'-methylurea |
| 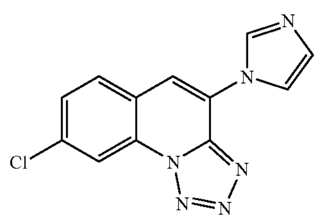 | 8-chloro-4-(1H-imidazol-1-yl)tetrazolo[1,5-a]quinoline |
| 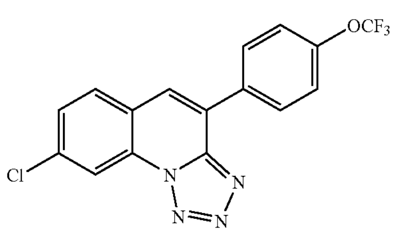 | 8-chloro-4-[4-(trifluoromethoxy)phenyl]tetrazolo[1,5-a]quinoline |
| 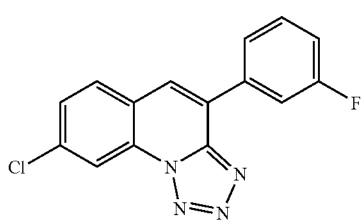 | 8-chloro-4-(3-fluorophenyl)tetrazolo[1,5-a]quinoline |
| 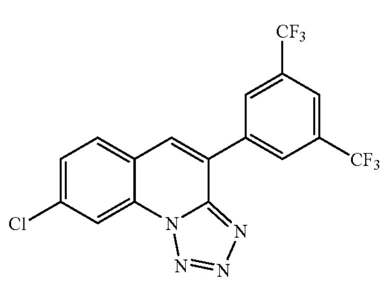 | 4-[3,5-bis(trifluoromethyl)phenyl]-8-chlorotetrazolo[1,5-a]quinoline |

TABLE 2-continued

| Structure | Name |
|---|---|
| 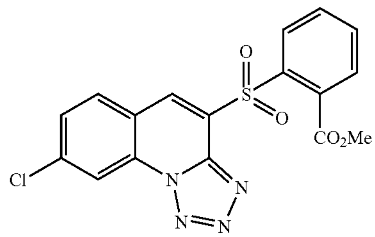 | methyl 2-[(8-chlorotetrazolo[1,5-a]quinolin-4-yl)sulfonyl]benzoate |
| 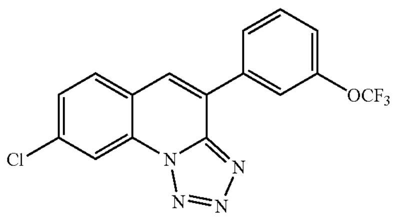 | 8-chloro-4-[3-(trifluoromethoxy)phenyl]tetrazolo[1,5-a]quinoline |
| 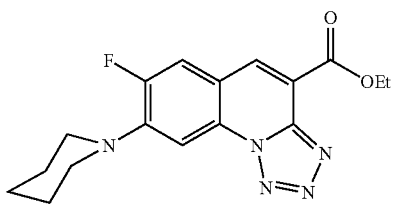 | ethyl 7-fluoro-8-piperidin-1-yltetrazolo[1,5-a]quinoline-4-carboxylate |
| 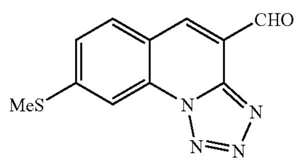 | 8-(methylthio)tetrazolo[1,5-a]quinoline-4-carbaldehyde |
| 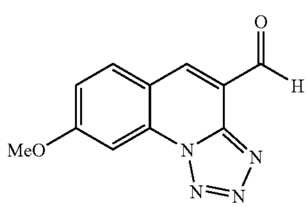 | 8-methoxytetrazolo[1,5-a]quinoline-4-carbaldehyde |
| 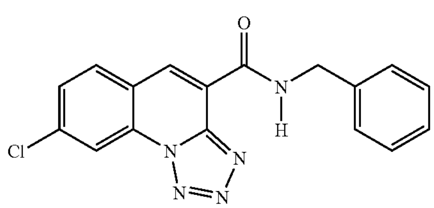 | N-benzyl-8-chlorotetrazolo[1,5-a]quinoline-4-carboxamide |
| 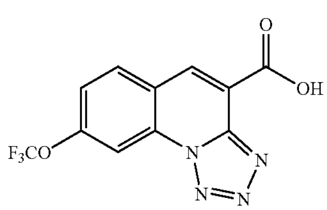 | 8-(trifluoromethoxy)tetrazolo[1,5-a]quinoline-4-carboxylic acid |

TABLE 2-continued

| Structure | Name |
|---|---|
| 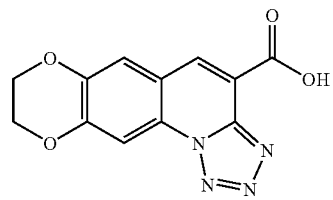 | 8,9-dihydro[1,4]dioxino[2,3-g]tetrazolo[1,5-a]quinoline-4-carboxylic acid |
| 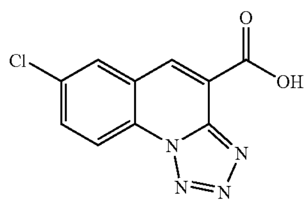 | 7-chlorotetrazolo[1,5-a]quinoline-4-carboxylic acid |
| 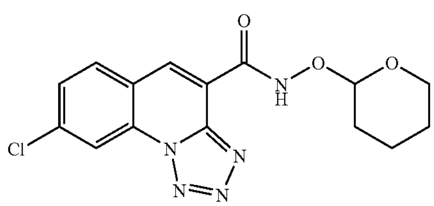 | 8-chloro-N-(tetrahydro-2H-pyran-2-yloxy)tetrazolo[1,5-a]quinoline-4-carboxamide<br>M − H$^+$ = 346 |
| 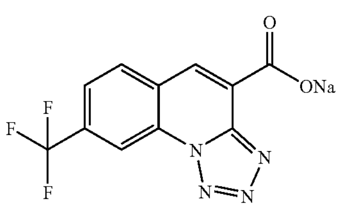 | sodium 8-(trifluoromethyl)tetrazolo[1,5-a]quinoline-4-carboxylate |
| 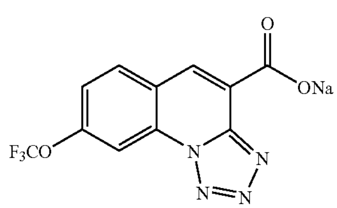 | sodium 8-(trifluoromethoxy)tetrazolo[1,5-a]quinoline-4-carboxylate |
| 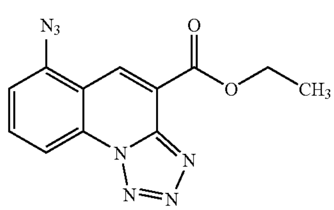 | ethyl 6-azidotetrazolo[1,5-a]quinoline-4-carboxylate |
| 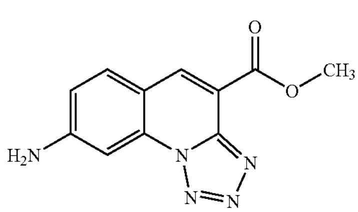 | methyl 8-aminotetrazolo[1,5-a]quinoline-4-carboxylate |

TABLE 2-continued

| Structure | Name |
|---|---|
| 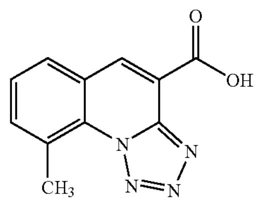 | 9-methyltetrazolo[1,5-a]quinoline-4-carboxylic acid |
| 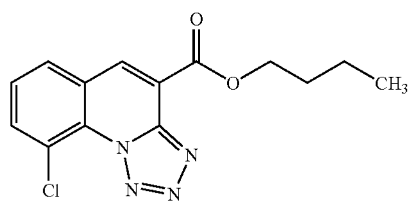 | butyl 9-chlorotetrazolo[1,5-a]quinoline-4-carboxylate |
| 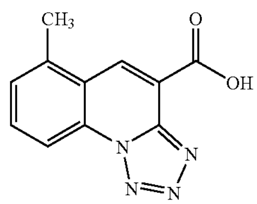 | 6-methyltetrazolo[1,5-a]quinoline-4-carboxylic acid |
| 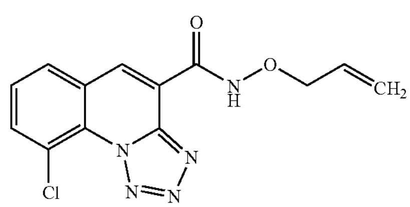 | N-(allyloxy)-9-chlorotetrazolo[1,5-a]quinoline-4-carboxamide |
| 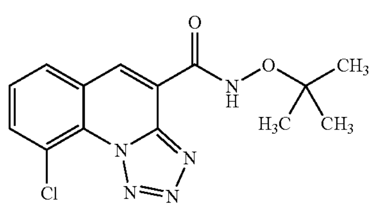 | N-(tert-butoxy)-9-chlorotetrazolo[1,5-a]quinoline-4-carboxamide |
| 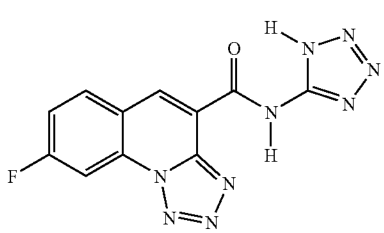 | 8-fluoro-N-1H-tetrazol-5-yltetrazolo[1,5-a]quinoline-4-carboxamide |
| 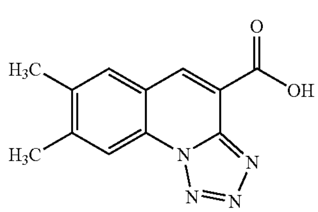 | 7,8-dimethyltetrazolo[1,5-a]quinoline-4-carboxylic acid |

TABLE 2-continued

| Structure | Name |
|---|---|
| 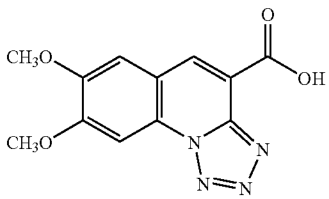 | 7,8-dimethoxytetrazolo[1,5-a]quinoline-4-carboxylic acid |
| 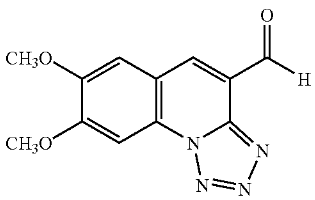 | 7,8-dimethoxytetrazolo[1,5-a]quinoline-4-carbaldehyde |
| 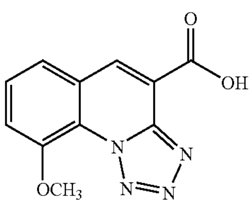 | 9-methoxytetrazolo[1,5-a]quinoline-4-carboxylic acid |
| 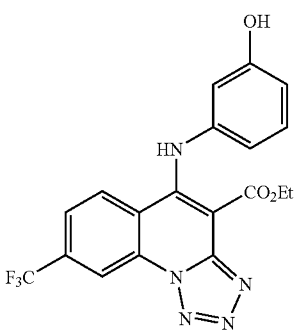 | ethyl 5-[(3-hydroxyphenyl)amino]-8-(trifluoromethyl)tetrazolo[1,5-a]quinoline-4-carboxylate |

Compounds exhibiting less than 5% inhibitory activity are listed in Table 3 below.

TABLE 3

| Structure | Name |
|---|---|
| 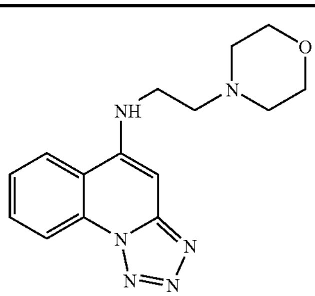 | N-(2-morpholin-4-yl-ethyl)tetrazolo[1,5-a]quinolin-5-amine |

TABLE 3-continued

| | |
|---|---|
| | 4-(phenylsulfonyl)tetrazolo[1,5-a]quinoline |
| | 4-pyridin-2-yltetrazolo[1,5-a]quinoline |
| | 4-pyridin-3-yltetrazolo[1,5-a]quinoline |
| | tetrazolo[1,5-a]quinoline-5-carboxylic acid |
| | 4-phenyltetrazolo[1,5-a]quinoline |
| | 8-chloro-4-pyridin-4-yl-tetrazolo[1,5-a]quinoline |
| | 8-chloro-4-[3-(trifluoromethyl)phenyl]tetrazolo[1,5-a]quinoline |

TABLE 3-continued

| Structure | Name |
|---|---|
| 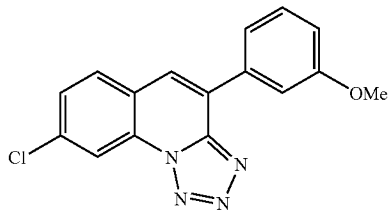 | 8-chloro-4-(3-methoxyphenyl)tetrazolo[1,5-a]quinoline |
| 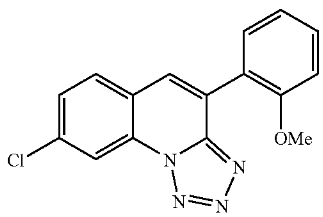 | 8-chloro-4-(2-methoxyphenyl)tetrazolo[1,5-a]quinoline |
| 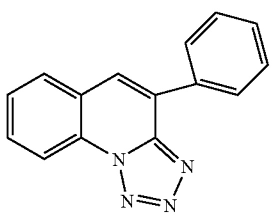 | 4-phenyltetrazolo[1,5-a]quinoline |
| 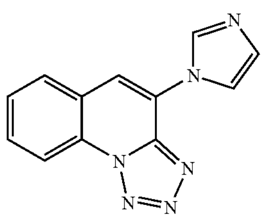 | 4-(1H-imidazol-1-yl)tetrazolo[1,5-a]quinoline |
| 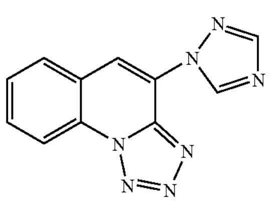 | 4-(1H-1,2,4-triazol-1-yl)tetrazolo[1,5-a]quinoline |
| 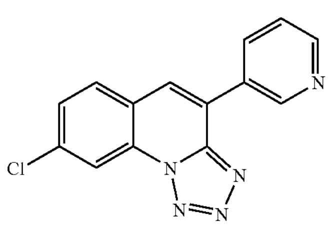 | 8-chloro-4-pyridin-3-yl-tetrazolo[1,5-a]quinoline |
| 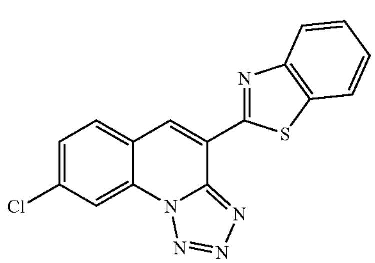 | 4-(1,3-benzothiazol-2-yl)-8-chloro-tetrazolo[1,5-a]quinoline |

TABLE 3-continued

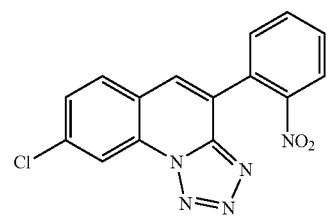
8-chloro-4-(2-nitrophenyl)tetrazolo[1,5-a]quinoline

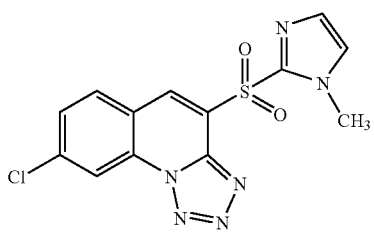
8-chloro-4-[(1-methyl-1H-imidazol-2-yl)sulfonyl]tetrazolo[1,5-a]quinoline

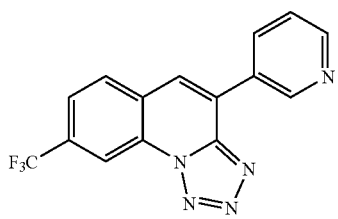
4-pyridin-3-yl-8-(trifluoromethyl)tetrazolo[1,5-a]quinoline

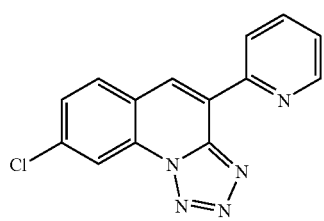
8-chloro-4-pyridin-2-yl-tetrazolo[1,5-a]quinoline

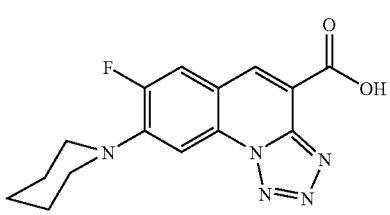
7-fluoro-8-piperidin-1-yl-tetrazolo[1,5-a]quinoline-4-carboxylic acid

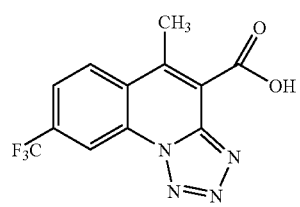
5-methyl-8-(trifluoromethyl)tetrazolo[1,5-a]quinoline-4-carboxylic acid

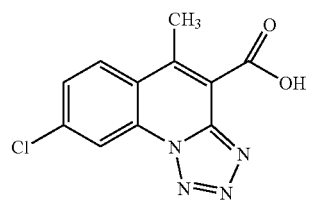
8-chloro-5-methyltetrazolo[1,5-a]quinoline-4-carboxylic acid

TABLE 3-continued

| Structure | Name |
|---|---|
| (structure) | N-methyltetrazolo[1,5-a]quinolin-5-amine |
| (structure) | tetrazolo[1,5-a]quinoline-4-carbothioamide |
| (structure) | 8-methyltetrazolo[1,5-a]quinoline-4-carboxylic acid |
| (structure) | 8-isopropoxytetrazolo[1,5-a]quinoline-4-carboxylic acid |
| (structure) | 8-methoxy-6-(trifluoromethyl)tetrazolo[1,5-a]quinoline-4-carboxylic acid |
| (structure) | 6-methoxy-8-(trifluoromethyl)tetrazolo[1,5-a]quinoline-4-carboxylic acid |
| (structure) | benzyl(8-chlorotetrazolo[1,5-a]quinolin-4-yl)carbamate |

TABLE 3-continued

| | |
|---|---|
| 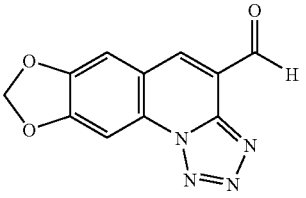 | [1,3]dioxolo[4,5-g]tetrazolo[1,5-a]quinoline-4-carbaldehyde |
| 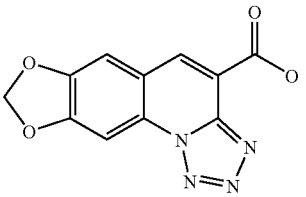 | [1,3]dioxolo[4,5-g]tetrazolo[1,5-a]quinoline-4-carboxylic acid |
| 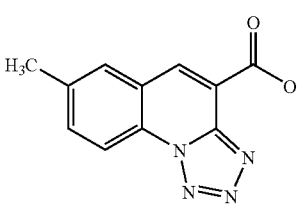 | 7-methyltetrazolo[1,5-a]quinoline-4-carboxylic acid |
| 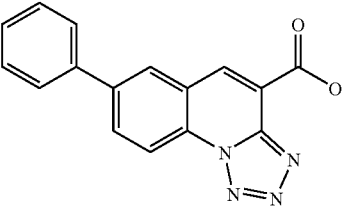 | 7-phenyltetrazolo[1,5-a]quinoline-4-carbaldehyde |
| 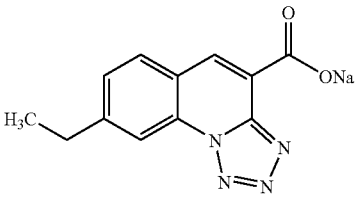 | sodium 8-ethyltetrazolo[1,5-a]quinoline-4-carboxylate |
| 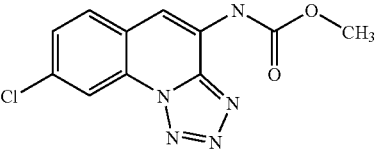 | methyl(8-chlorotetrazolo[1,5-a]quinolin-4-yl)carbamate |
| 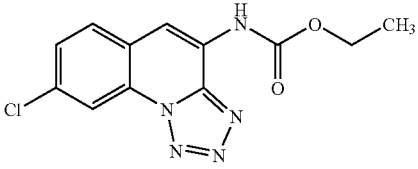 | ethyl(8-chlorotetrazolo[1,5-a]quinolin-4-yl)carbamate |
| 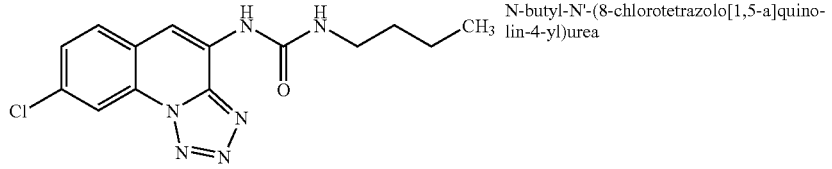 | N-butyl-N'-(8-chlorotetrazolo[1,5-a]quinolin-4-yl)urea |

TABLE 3-continued

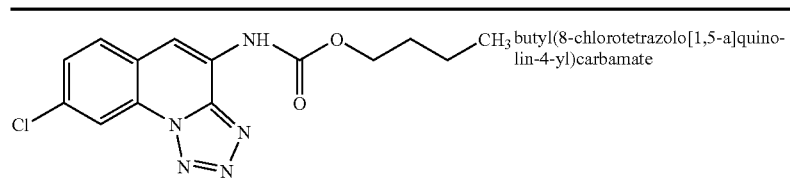 butyl(8-chlorotetrazolo[1,5-a]quinolin-4-yl)carbamate

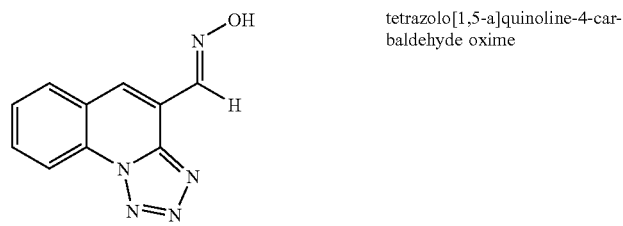 tetrazolo[1,5-a]quinoline-4-carbaldehyde oxime

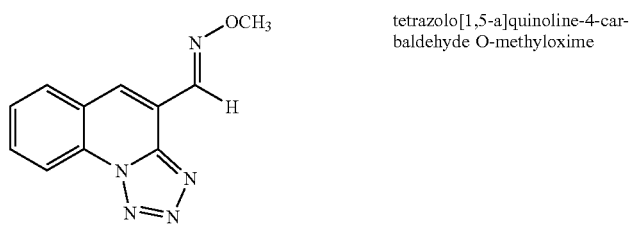 tetrazolo[1,5-a]quinoline-4-carbaldehyde O-methyloxime

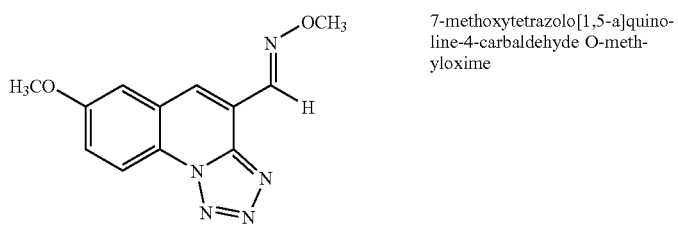 7-methoxytetrazolo[1,5-a]quinoline-4-carbaldehyde O-methyloxime

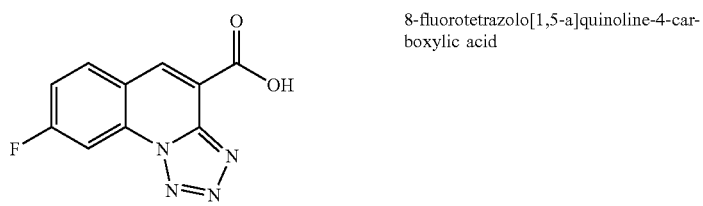 8-fluorotetrazolo[1,5-a]quinoline-4-carboxylic acid

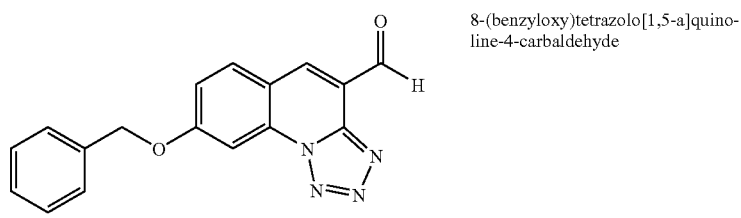 8-(benzyloxy)tetrazolo[1,5-a]quinoline-4-carbaldehyde

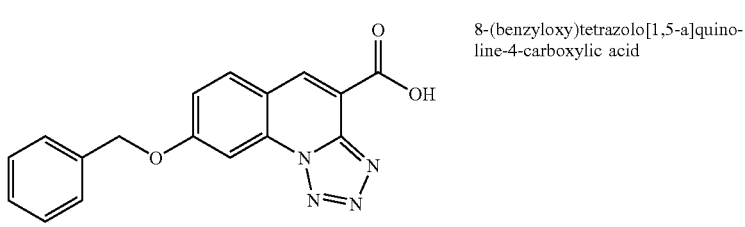 8-(benzyloxy)tetrazolo[1,5-a]quinoline-4-carboxylic acid

TABLE 3-continued

| Structure | Name |
|---|---|
| 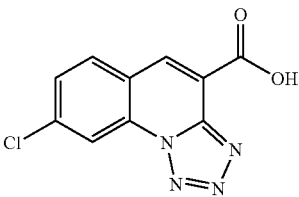 | 8-chlorotetrazolo[1,5-a]quinoline-4-carboxylic acid |
| 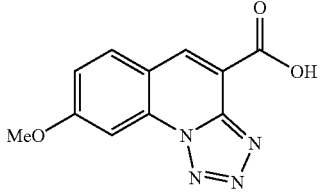 | 8-methoxytetrazolo[1,5-a]quinoline-4-carboxylic acid |
| 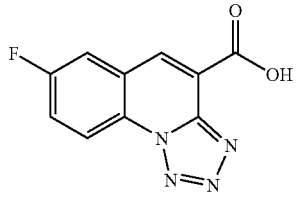 | 7-fluorotetrazolo[1,5-a]quinoline-4-carboxylic acid |
| 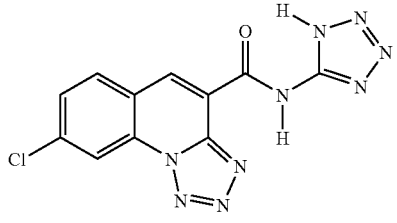 | 8-chloro-N-1H-tetrazol-5-yl-tetrazolo[1,5-a]quinoline-4-carboxamide |
| 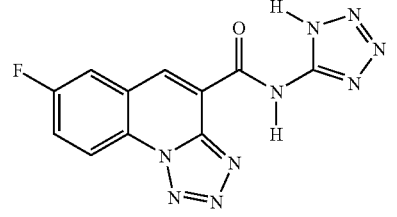 | 7-fluoro-N-1H-tetrazol-5-yl-tetrazolo[1,5-a]quinoline-4-carboxamide |
| 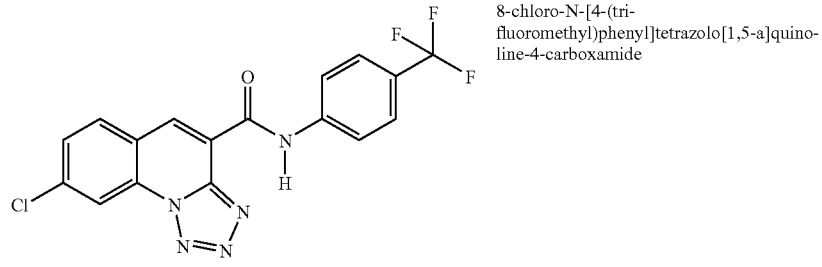 | 8-chloro-N-[4-(trifluoromethyl)phenyl]tetrazolo[1,5-a]quinoline-4-carboxamide |
| 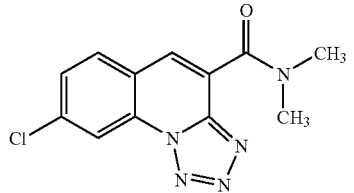 | 8-chloro-N,N-dimethyltetrazolo[1,5-a]quinoline-4-carboxamide |

TABLE 3-continued

| | |
|---|---|
| 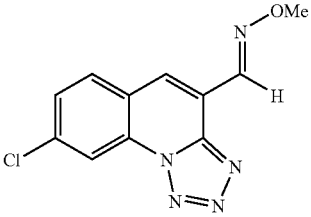 | 8-chlorotetrazolo[1,5-a]quinoline-4-carbaldehyde O-methyloxime |
| 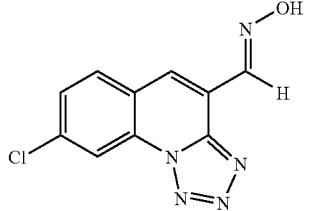 | 8-chlorotetrazolo[1,5-a]quinoline-4-carbaldehyde oxime |
| 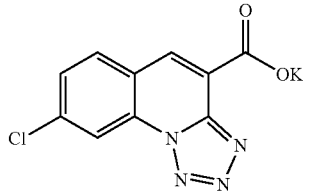 | potassium 8-chlorotetrazolo[1,5-a]quinoline-4-carboxylate |
| 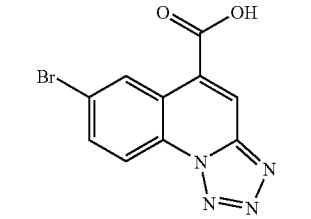 | 7-bromotetrazolo[1,5-a]quinoline-5-carboxylic acid |
| 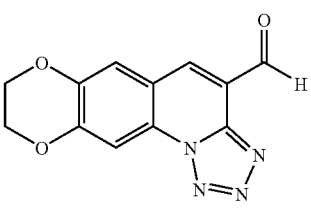 | 8,9-dihydro[1,4]dioxino[2,3-g]tetrazolo[1,5-a]quinoline-4-carbaldehyde |
| 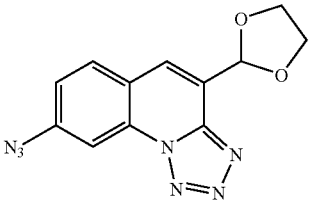 | 8-azido-4-(1,3-dioxolan-2-yl)tetrazolo[1,5-a]quinoline |
| 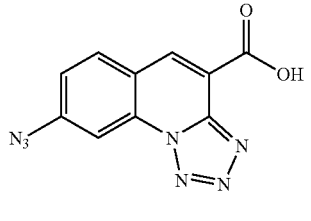 | 8-azidotetrazolo[1,5-a]quinoline-4-carboxylic acid |

TABLE 3-continued

| Structure | Name |
|---|---|
| (structure) | ethyl 8-(trifluoromethyl)tetrazolo[1,5-a]quinoline-4-carboxylate |
| (structure) | 8-(trifluoromethyl)tetrazolo[1,5-a]quinoline-4-carboxylic acid |
| (structure) | 8-chloro-N-methoxytetrazolo[1,5-a]quinoline-4-carboxamide |
| (structure) | methyl 8-azidotetrazolo[1,5-a]quinoline-4-carboxylate |
| (structure) | 8-(trifluoromethoxy)tetrazolo[1,5-a]quinoline-4-carbaldehyde |
| (structure) | ethyl 9-(trifluoromethyl)tetrazolo[1,5-a]quinoline-4-carboxylate |
| (structure) | ethyl 9-chlorotetrazolo[1,5-a]quinoline-4-carboxylate |

TABLE 3-continued

| Structure | Name |
|---|---|
| 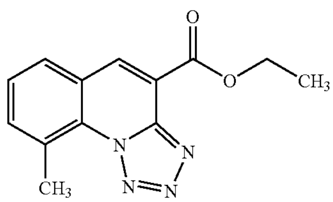 | ethyl 9-methyltetrazolo[1,5-a]quinoline-4-carboxylate |
| 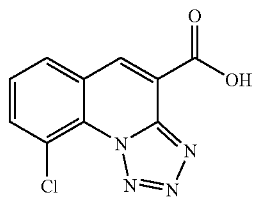 | 9-chlorotetrazolo[1,5-a]quinoline-4-carboxylic acid |
| | N-(benzyloxy)-9-chlorotetrazolo[1,5-a]quinoline-4-carboxamide |
| 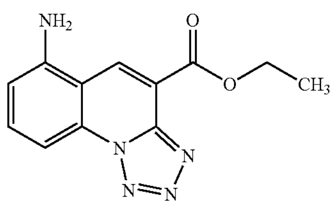 | ethyl 6-aminotetrazolo[1,5-a]quinoline-4-carboxylate |
| 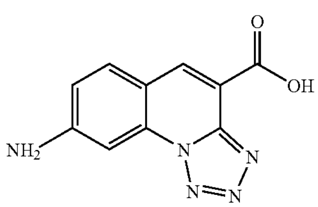 | 8-aminotetrazolo[1,5-a]quinoline-4-carboxylic acid |
| 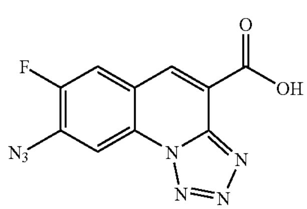 | 8-azido-7-fluorotetrazolo[1,5-a]quinoline-4-carboxylic acid |
| 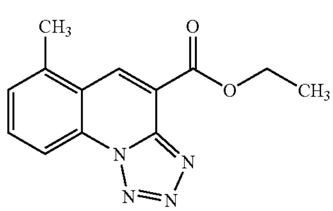 | ethyl 6-methyltetrazolo[1,5-a]quinoline-4-carboxylate |

TABLE 3-continued

| Structure | Name |
|---|---|
| 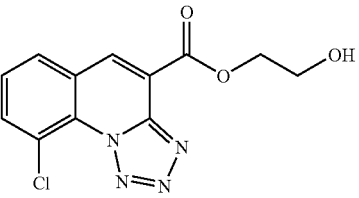 | 2-hydroxyethyl 9-chloro-tetrazolo[1,5-a]quinoline-4-carboxylate |
| 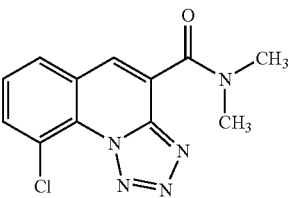 | 9-chloro-N,N-dimethyltetrazolo[1,5-a]quinoline-4-carboxamide |
| 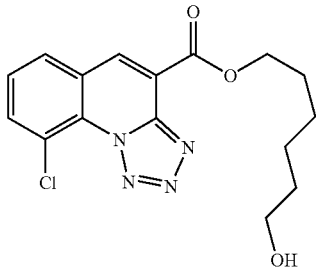 | 6-hydroxyhexyl 9-chloro-tetrazolo[1,5-a]quinoline-4-carboxylate |
| 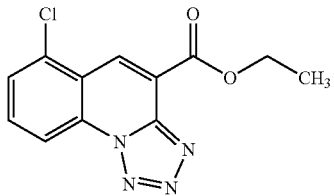 | ethyl 6-chlorotetrazolo[1,5-a]quinoline-4-carboxylate |
| 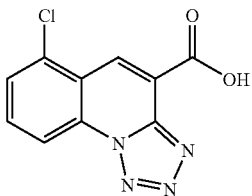 | 6-chlorotetrazolo[1,5-a]quinoline-4-carboxylic acid |
| 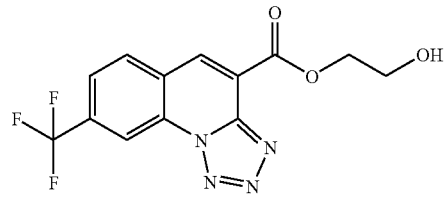 | 2-hydroxyethyl 8-(trifluoromethyl)tetrazolo[1,5-a]quinoline-4-carboxylate |
| 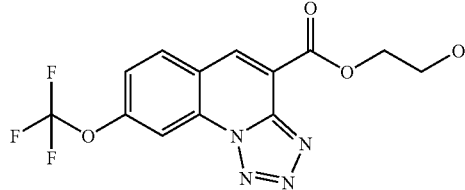 | 2-hydroxyethyl 8-(trifluoromethoxy)tetrazolo[1,5-a]quinoline-4-carboxylate |

TABLE 3-continued

| | |
|---|---|
| 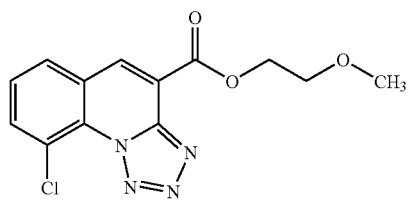 | 2-methoxyethyl 9-chloro-tetrazolo[1,5-a]quinoline-4-carboxylate |
| 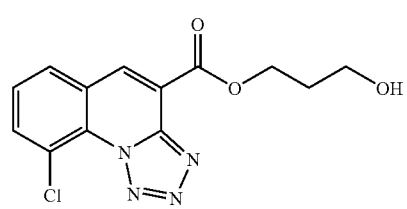 | 3-hydroxypropyl 9-chloro-tetrazolo[1,5-a]quinoline-4-carboxylate |
| 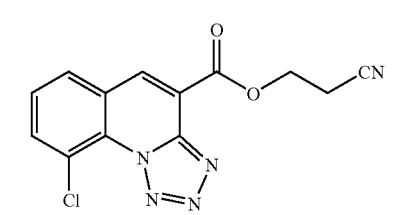 | 2-cyanoethyl 9-chloro-tetrazolo[1,5-a]quinoline-4-carboxylate |
| 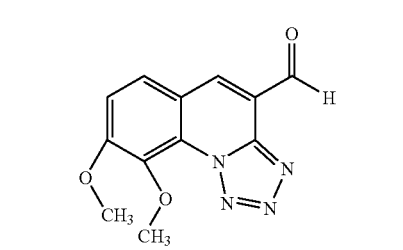 | 8,9-dimethoxytetrazolo[1,5-a]quinoline-4-carbaldehyde |
| 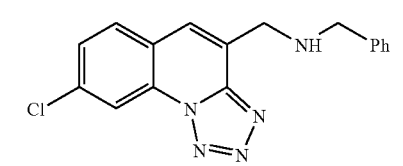 | N-benzyl-1-(8-chlorotetrazolo[1,5-a]quinolin-4-yl)methanamine |
| 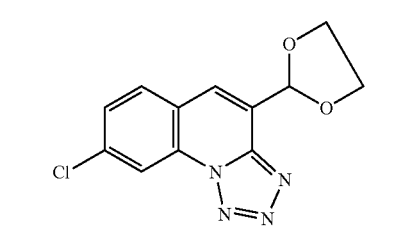 | 8-chloro-4-(1,3-dioxolan-2-yl)tetrazolo[1,5-a]quinoline |
| 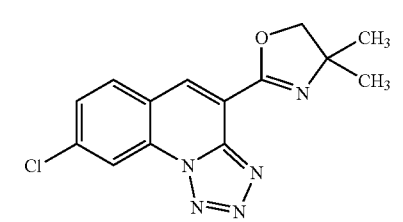 | 8-chloro-4-(4,4-dimethyl-4,5-dihydro-1,3-oxazol-2-yl)tetrazolo[1,5-a]quinoline |

TABLE 3-continued

| Structure | Name |
|---|---|
| 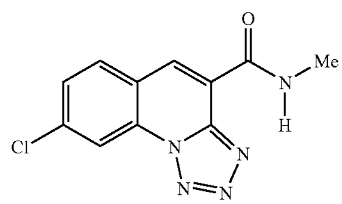 | 8-chloro-N-methyltetrazolo[1,5-a]quinoline-4-carboxamide |
| 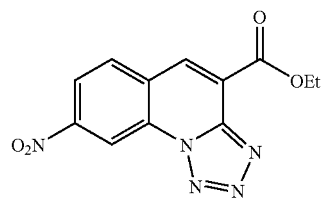 | ethyl 8-nitrotetrazolo[1,5-a]quinoline-4-carboxylate |
| 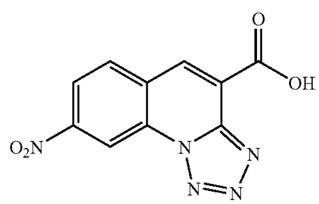 | 8-nitrotetrazolo[1,5-a]quinoline-4-carboxylic acid |
| 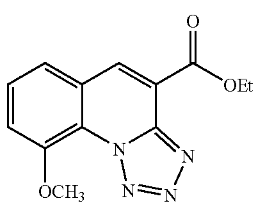 | ethyl 9-methoxytetrazolo[1,5-a]quinoline-4-carboxylate |
| 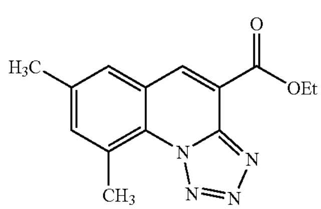 | ethyl 7,9-dimethyltetrazolo[1,5-a]quinoline-4-carboxylate |
| 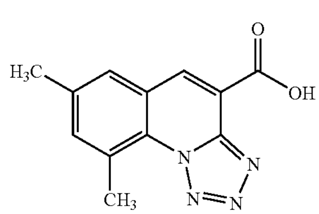 | 7,9-dimethyltetrazolo[1,5-a]quinoline-4-carboxylic acid |
| | isobutyl 8-azido-7-fluoro-tetrazolo[1,5-a]quinoline-4-carboxylate |

TABLE 3-continued

| Structure | Name |
|---|---|
| 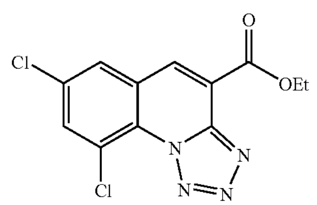 | ethyl 7,9-dichlorotetrazolo[1,5-a]quinoline-4-carboxylate |
| 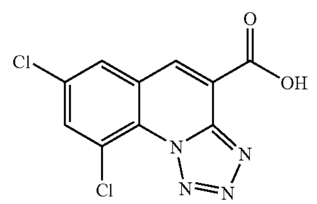 | 7,9-dichlorotetrazolo[1,5-a]quinoline-4-carboxylic acid |
| 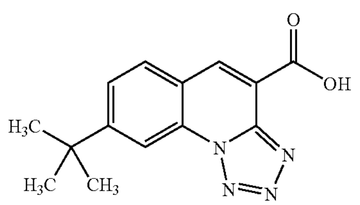 | 8-tert-butyltetrazolo[1,5-a]quinoline-4-carboxylic acid |
| 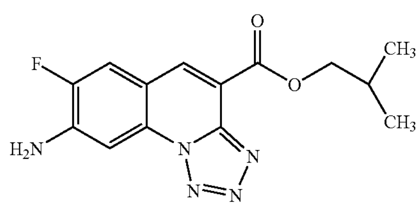 | isobutyl 8-amino-7-fluoro-tetrazolo[1,5-a]quinoline-4-carboxylate |
| 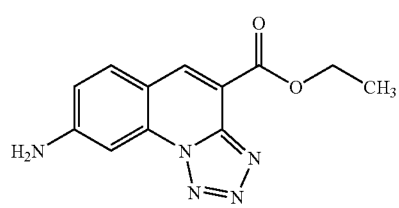 | ethyl 8-aminotetrazolo[1,5-a]quinoline-4-carboxylate |
| 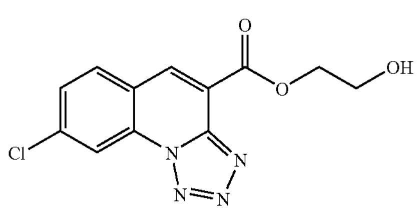 | 2-hydroxyethyl 8-chloro-tetrazolo[1,5a]quinoline-4-carboxylate |
| 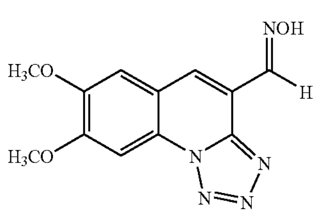 | 4-[(hydroxyamino)methyl]-7,8-dimethoxytetrazolo[1,5-a]quinoline |

TABLE 3-continued

| Structure | Name |
|---|---|
| (structure) | 3-{[(1E)-(7,8-dimethoxytetrazolo[1,5-a]quinolin-4-yl)methylene]amino}phenol |
| (structure) | 3-{[(7,8-dimethoxytetrazolo[1,5-a]quinolin-4-yl)methyl]amino}phenol |

Compounds listed in Table 4 below also exhibit inhibitory activity.

TABLE 4

| Structure | Name | Activity (IC50) | M − H+ |
|---|---|---|---|
| (structure) | N-hydroxy-9-methyltetrazolo[1,5-a]quinoline-4-carboxamide | +++ | 244 |
| (structure) | 9-chloro-N-hydroxytetrazolo[1,5-a]quinoline-4-carboxamide | +++ | 264 |
| (structure) | 8-chloro-N-hydroxytetrazolo[1,5-a]quinoline-4-carboxamide | +++ | 264 |
| (structure) | 7-chloro-N-hydroxytetrazolo[1,5-a]quinoline-4-carboxamide | +++ | 264 |

TABLE 4-continued

| Structure | Name | Activity (IC50) | M − H+ |
|---|---|---|---|
| 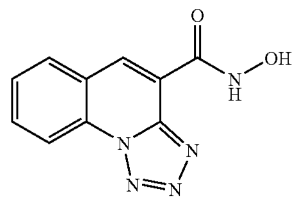 | N-hydroxytetrazolo[1,5-a]quinoline-4-carboxamide | +++ | 230 |
| 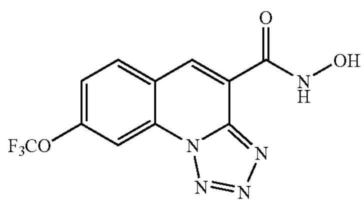 | N-hydroxy-8-(trifluoromethoxy)tetrazolo[1,5-a]quinoline-4-carboxamide | +++ | 312 |
| 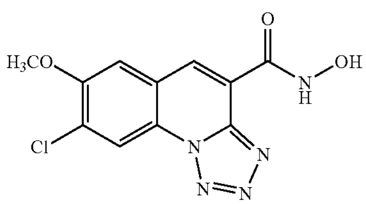 | 8-chloro-N-hydroxy-7-methoxytetrazolo[1,5-a]quinoline-4-carboxamide | +++ | 292 |
| 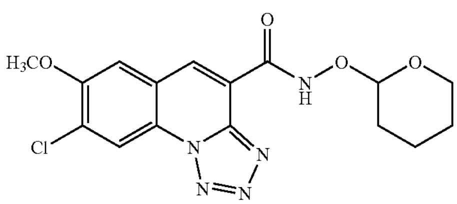 | 8-chloro-7-methoxy-N-(tetrahydro-2H-pyran-2-yloxy)tetrazolo[1,5-a]quinoline-4-carboxamide | + | 294 |
| 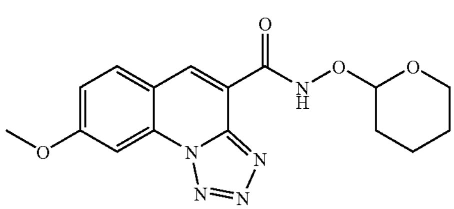 | 8-methoxy-N-(tetrahydro-2H-pyran-2-yloxy)tetrazolo[1,5-a]quinoline-4-carboxamide | + | 342 |
| 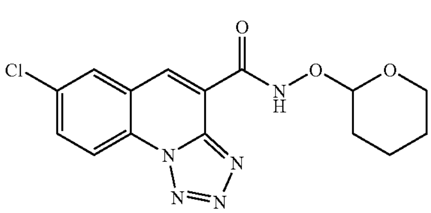 | 7-chloro-N-(tetrahydro-2H-pyran-2-yloxy)tetrazolo[1,5-a]quinoline-4-carboxamide | + | 346 |
| 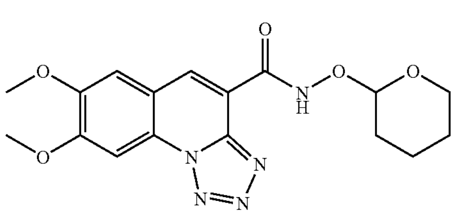 | 7,8-dimethoxy-N-(tetrahydro-2H-pyran-2-yloxy)tetrazolo[1,5-a]quinoline-4-carboxamide | +++ | 372 |

TABLE 4-continued

| Structure | Name | Activity (IC50) | M − H+ |
|---|---|---|---|
|  | 9-methyl-N-(tetrahydro-2H-pyran-2-yl-oxy)tetrazolo[1,5-a]quinoline-4-carboxamide | + | 326 |
|  | methyl tetrazolo[1,5-a]quinoline-5-carboxylate | + | 229 |
|  | N-(tetrahydro-2H-pyran-2-yl-oxy)tetrazolo[1,5-a]quinoline-4-carboxamide | + | 313 |
|  | N-(tetrahydro-2H-pyran-2-yloxy)-8-(trifluoromethoxy)tetrazolo[1,5-a]quinoline-4-carboxamide | + | 396 |
|  | 8-chloro-N-hydroxy-N-methyltetrazolo[1,5-a]quinoline-4-carboxamide | + | 278 |
|  | 9-chloro-N-(tetrahydro-2H-pyran-2-yl-oxy)tetrazolo[1,5-a]quinoline-4-carboxamide | + | 346 |
|  | N-hydroxy-8,9-dihydro[1,4]dioxino[2,3-g]tetrazolo[1,5-a]quinoline-4-carboxamide | +++ | 286 |

TABLE 4-continued

| Structure | Name | Activity (IC50) | M − H⁺ |
|---|---|---|---|
| 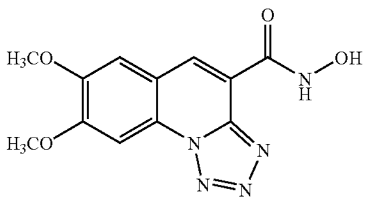 | N-hydroxy-7,8-dimethoxytetrazolo[1,5-a]quinoline-4-carboxamide | +++ | 288 |
| 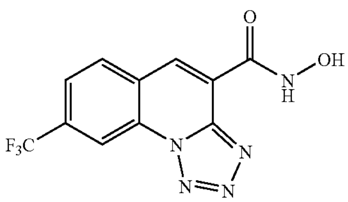 | N-hydroxy-8-(trifluoromethyl)tetrazolo[1,5-a]quinoline-4-carboxamide | +++ | 298 |
| 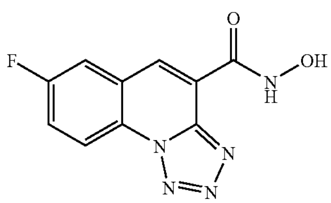 | 7-fluoro-N-hydroxytetrazolo[1,5-a]quinoline-4-carboxamide | +++ | 246 |
| 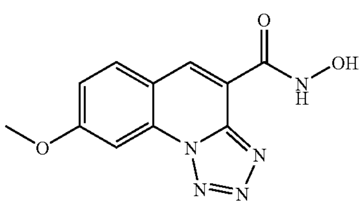 | N-hydroxy-8-methoxytetrazolo[1,5-a]quinoline-4-carboxamide | + | 260 |
| 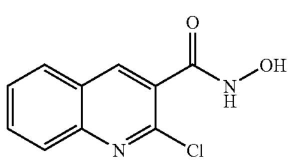 | 2-chloro-N-hydroxyquinoline-3-carboxamide | + | |
| 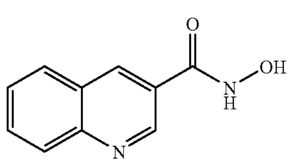 | N-hydroxyquinoline-3-carboxamide | + | |
| 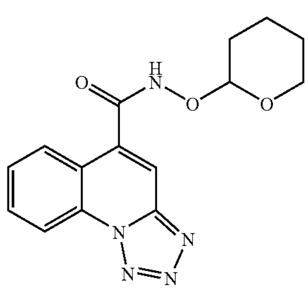 | N-(tetrahydro-2H-pyran-2-yloxy)tetrazolo[1,5-a]quinoline-5-carboxamide | + | 314 |

TABLE 4-continued

| Structure | Name | Activity (IC50) | M − H+ |
|---|---|---|---|
| 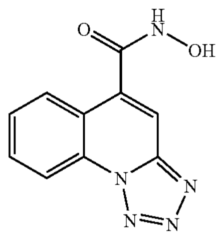 | N-hydroxytetrazolo[1,5-a]quinoline-5-carboxamide | + | 230 |
| 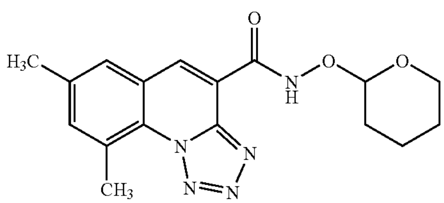 | 7,9-dimethyl-N-(tetrahydro-2H-pyran-2-yloxy)tetrazolo[1,5-a]quinoline-4-carboxamide | + | 340 |
| 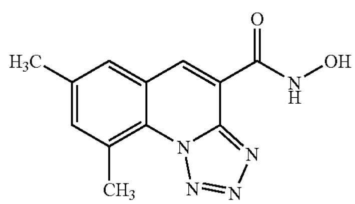 | N-hydroxy-7,9-dimethyltetrazolo[1,5-a]quinoline-4-carboxamide | +++ | 258 |
| 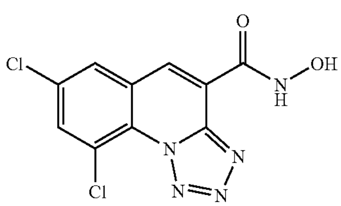 | 7,9-dichloro-N-hydroxytetrazolo[1,5-a]quinoline-4-carboxamide | +++ | 298 |
| 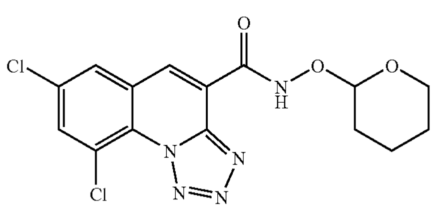 | 7,9-dichloro-N-(tetrahydro-2H-pyran-2-yloxy)tetrazolo[1,5-a]quinoline-4-carboxamide | + | 380 |
| 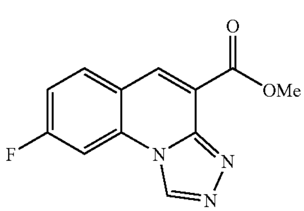 | methyl 8-fluoro-[1,2,4]triazolo[4,3-a]quinoline-4-carboxylate | + | 246 |
| 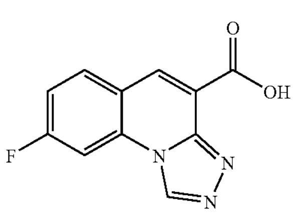 | 8-fluoro-[1,2,4]triazolo[4,3-a]quinoline-4-carboxylic acid | + | 232 |

TABLE 4-continued

| Structure | Name | Activity (IC50) | M − H⁺ |
|---|---|---|---|
| 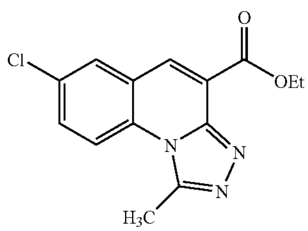 | ethyl 7-chloro-1-methyl-[1,2,4]triazolo[4,3-a]quinoline-4-carboxylate | + | 290 |
| 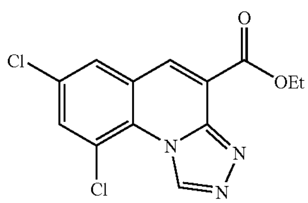 | ethyl 7,9-dichloro-[1,2,4]triazolo[4,3-a]quinoline-4-carboxylate | + | 310 |
| 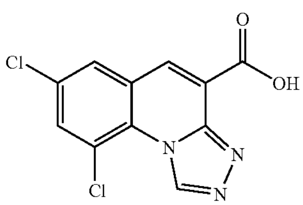 | 7,9-dichloro-[1,2,4]triazolo[4,3-a]quinoline-4-carboxylic acid | + | 282 |
| 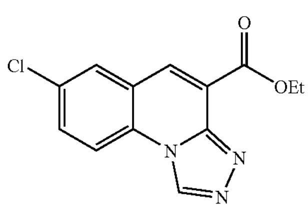 | ethyl 7-chloro-[1,2,4]triazolo[4,3-a]quinoline-4-carboxylate | + | 276 |
| 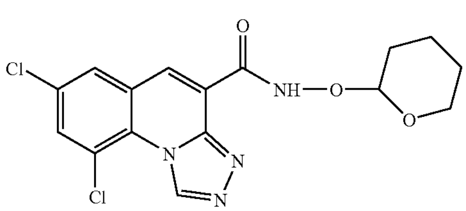 | 7,9-dichloro-N-(tetrahydro-2H-pyran-2-yloxy)-[1,2,4]triazolo[4,3-a]quinoline-4-carboxamide | + | 379 |
| 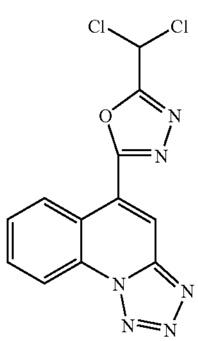 | 5-(5-(dichloromethyl)-1,3,4-oxadiazol-2-yl)tetrazolo[1,5-a]quinoline | + | 321 |

TABLE 4-continued

| Structure | Name | Activity (IC50) | M − H⁺ |
|---|---|---|---|
| 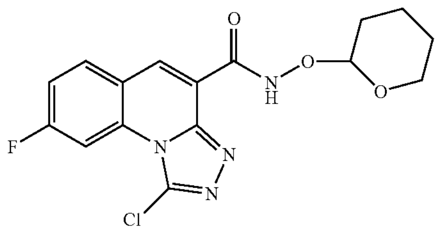 | 1-chloro-8-fluoro-N-(tetrahydro-2H-pyran-2-yloxy)-[1,2,4]triazolo[4,3-a]quinoline-4-carboxamide | + | 365 |
| 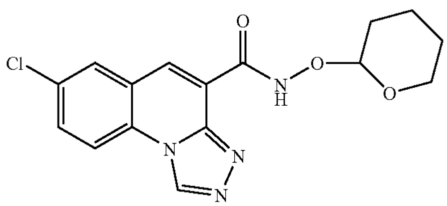 | 7-chloro-N-(tetrahydro-2H-pyran-2-yloxy)-[1,2,4]triazolo[4,3-a]quinoline-4-carboxamide | + | 345 |
| 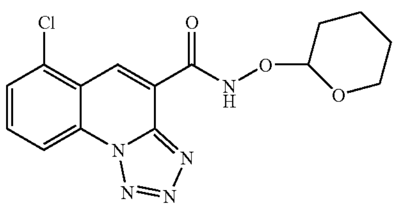 | 6-chloro-N-(tetrahydro-2H-pyran-2-yloxy)tetrazolo[1,5-a]quinoline-4-carboxamide | + | 348 |
| 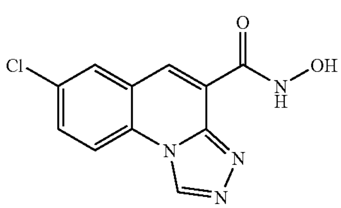 | 7-chloro-N-hydroxy-[1,2,4]triazolo[4,3-a]quinoline-4-carboxamide | +++ | 263 |
| 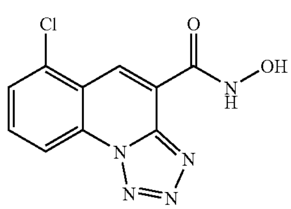 | 6-chloro-N-hydroxytetrazolo[1,5-a]quinoline-4-carboxamide | +++ | 264 |
| 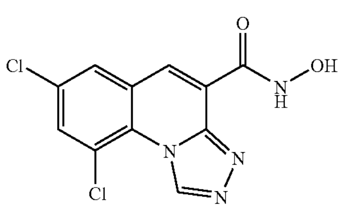 | 7,9-dichloro-N-hydroxy-[1,2,4]triazolo[4,3-a]quinoline-4-carboxamide | +++ | 297 |
| 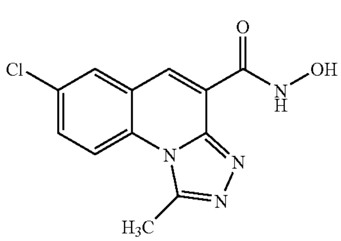 | 7-chloro-N-hydroxy-1-methyl-[1,2,4]triazolo[4,3-a]quinoline-4-carboxamide | +++ | 277 |

TABLE 4-continued

| Structure | Name | Activity (IC50) | M – H⁺ |
|---|---|---|---|
| 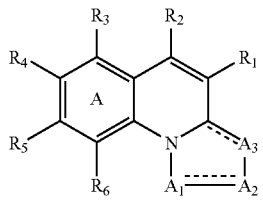 | 1-chloro-8-fluoro-N-hydroxy-[1,2,4]tri-azolo[4,3-a]quinoline-4-car-boxamide | +++ | 281 |

+++ means less than 10 μM
+ means greater than 10 μM

We claim:

1. A compound of the formula

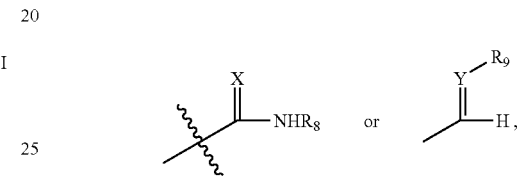

or a pharmaceutically acceptable salt thereof wherein $R_1$ is —CO—H, —CO—$NR_7R_7$, —CO—NH—OH, —CO—NH—$OR_7$, or —CO—N($R_7$)—$OR_7$, $R_2$ is hydrogen, $C_1$-$C_6$-alkyl, aryl, heterocyclic, $C_1$-$C_6$-alkyl-OH, heteroaryl selected from the group consisting of acridinyl, azocinyl, benzimidazolyl, benzofuranyl, benzothiofuranyl, benzothienyl, benzoxazolyl, benzthiazolyl, benztriazolyl, benztetrazolyl, benzisoxazolyl, benzisothiazolyl, benzimidazolinyl, carbazolyl, 4aH-carbazolyl, furanyl, furazanyl, imidazolidinyl, imidazolinyl, imidazolyl, 1H-indazolyl, isobenzofuranyl, isoindazolyl, isoindolinyl, isoindolyl, isoquinolinyl, isothiazolyl, isoxazolyl, naphthyridinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolyl, quinazolinyl, quinolinyl, quinoxalinyl, 1,2,3-thiadiazolyl, 1,2,4-thiadiazolyl, 1,2,5-thiadiazolyl, 1,3,4-thiadiazolyl, thiazolyl, thienyl, thienothiazolyl, thienooxazolyl, thienoimidazolyl, thienyl, triazinyl, 1,2,3-triazolyl, 1,2,4-triazolyl, 1,2,5-triazolyl, and 1,3,4-triazolyl, cyano, —CO—H, —CO—OH, —CO—$OR_7$, —CO—$NH_2$, —CO—$NR_7R_7$, —CO—$NR_7R_7$, —CO—NH—OH, —CO—NH—$OR_7$, —CO—N($R_7$)—$OR_7$, —CO—$R_7$, —$SO_2NH_2$, —$SO_2NHR_7$, —$SO_2NR_7R_7$, —$SO_2$-heteroaryl, —$SO_2$-aryl, —CO-heteroaryl, —NH—CO—NH—$SO_2$-aryl, —NH—CO—$OR_7$, —NH—CO—NH—($C_1$-$C_6$-alkyl) or —NH—CO—($C_1$-$C_6$-alkyl), wherein each of the heteroaryl and aryl groups are optionally substituted with $C_1$-$C_6$-alkyl, nitro, hydroxy, $C_1$-$C_6$-alkoxy, —CO—O—($C_1$-$C_6$-akyl), cyano, —O-halo($C_1$-$C_6$-alkyl), halo($C_1$-$C_6$-alkyl) or halogen, or $R_2$ is a group selected from wherein $R_8$ is hydrogen or hydroxyl; X is =NH or =S—, Y is =N—, and $R_9$ is hydroxyl, $C_1$-$C_6$-alkoxy or aryl optionally substituted with hydroxyl or $C_1$-$C_6$-alkyl; $R_3$ is hydrogen, nitro, aryl, —O-halo($C_1$-$C_6$-alkyl), halo ($C_1$-$C_6$-alkyl), —O—($C_3$-$C_6$-cycloalkyl), —S—($C_1$-$C_6$-alkyl), heterocyclyl, $C_1$-$C_6$-alkoxy, —($C_1$-$C_6$-alkoxy)-aryl, azido, halogen, —$OCF_3$, —$CF_3$, —CO—H, —CO—OH, —CO—$OR_7$, —CO—$NH_2$, —CO—$NHR_7$, —CO—$NR_7R_7$, —CO—N($R_7$)$OR_7$, —CO—$R_7$, —$SO_2$—($C_1$-$C_6$-alkyl), —$SO_2NH_2$, —$SO_2NHR_7$, —$SO_2NR_7R_7$, —CO-heteroaryl, —$NH_2$, —$NHR_7$, —$NR_7R_7$, —OH, —N($R_7$)—CO—$R_7$, —$NHSO_2R_7$, —N($R_7$)—CO—$OR_7$ or —N($R_7$)—CO—$NR_7R_7$;

$R_4$ and $R_5$ are independently hydrogen, nitro, $C_1$-$C_6$-alkyl, aryl, —O-halo($C_1$-$C_6$-alkyl), halo($C_1$-$C_6$-alkyl), —O—($C_3$-$C_6$-cycloalkyl), —S—($C_1$-$C_6$-alkyl), heterocyclyl, $C_1$-$C_6$-alkoxy, —($C_1$-$C_6$-alkoxy)-aryl, azido, halogen, —$OCF_3$, —$CF_3$, —CO—H, —CO—OH, —CO—$OR_7$, —CO—$NH_2$, —CO—$NHR_7$, —CO—$NR_7R_7$, —CO—N($R_7$)$OR_7$, —$SO_2$—($C_1$-$C_6$-alkyl), —$SO_2NH_2$, —$SO_2NHR_7$, —$SO_2NR_7R_7$, —CO-heteroaryl, —$NH_2$, —$NHR_7$, —$NR_7R_7$, —OH, —N($R_7$)—CO—$R_7$, —$NHSO_2R_7$, —N($R_7$)—CO—$OR_7$ or —N($R_7$)—CO—$NR_7R_7$, or $R_4$ and $R_5$ together with the carbon atoms to which they are attached form a heteroaryl;

$R_6$ is hydrogen, nitro, $C_1$-$C_6$-alkyl, aryl, —O-halo($C_1$-$C_6$-alkyl), —O—($C_3$-$C_6$-cycloalkyl), —S—($C_1$-$C_6$-alkyl), heterocyclyl, $C_1$-$C_6$-alkoxy, —($C_1$-$C_6$-alkoxy)-aryl, azido, halogen, —$OCF_3$, —$CF_3$, —CO—H, —CO—OH, —CO—$OR_7$, —CO—$NH_2$, —CO—$NHR_7$, —CO—$NR_7R_7$, —CO—N($R_7$)$OR_7$, —CO—$R_7$, —$SO_2$—($C_1$-$C_6$-alkyl), —$SO_2NH_2$, —$SO_2NHR_7$, —$SO_2NR_7R_7$, —CO-heteroaryl, —$NH_2$, —$NHR_7$, —$NR_7R_7$, —OH, —N($R_7$)—CO—$R_7$, —$NHSO_2R_7$, —N($R_7$)—CO—$OR_7$ or —N($R_7$)—CO—$NR_7R_7$;

$R_7$ is $C_1$-$C_6$alkyl, —($C_1$-$C_6$-alkyl)-OH, —($C_1$-$C_6$-alkyl)-O—($C_1$-$C_6$-alkyl), —($C_1$-$C_6$-alkyl)-CN, $C_2$-$C_6$-alkene, heterocyclyl, aryl, heteroaryl or —($C_1$-$C_6$-alkyl)-aryl, wherein each of the aryl, heterocyclyl and heteroaryl groups are optionally substituted with $C_1$-$C_6$-alkyl, nitro, hydroxyl, $C_1$-$C_6$-alkoxy, —CO—O—($C_1$-$C_6$-alkyl), cyano, —O-halo($C_1$-$C_6$-alkyl), halo($C_1$-$C_6$-alkyl) or halogen;

$A_1$, $A_2$ and $A_3$ are nitrogen;

provided that:

when $R_2$ to $R_6$ are hydrogen, $R_1$ is not —CO—H; and the compound of formula I is not 8-methyltetrazolo[1,5-a]quinoline-4-carbaldehyde.

2. A compound of the formula

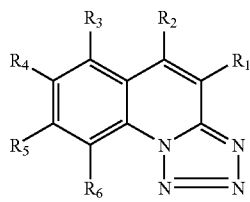

or a pharmaceutically acceptable salt thereof wherein $R_1$ is —C O—H, —CO—$NR_7R_7$, —C O—NH—OH, —CO—NH—$OR_7$, or —CO—N($R_7$)—$OR_7$, $R_2$ is hydrogen, $C_1$-$C_6$-alkyl, heterocyclic, $C_1$-$C_6$-alkyl-OH, aryl, heteroaryl selected from the group consisting of acridinyl, azocinyl, benzimidazolyl, benzofuranyl, benzothiofuranyl, benzothienyl, benzoxazolyl, benzthiazolyl, benztriazolyl, benztetrazolyl, benzisoxazolyl, benzisothiazolyl, benzimidazolinyl, carbazolyl, 4aH-carbazolyl, furanyl, furazanyl, imidazolidinyl, imidazolinyl, imidazolyl, 1H-indazolyl, isobenzofuranyl, isoindazolyl, isoindolinyl, isoindolyl, isoquinolinyl, isothiazolyl, isoxazolyl, naphthyridinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolyl, quinazolinyl, quinolinyl, quinoxalinyl, 1,2,3-thiadiazolyl, 1,2,4-thiadiazolyl, 1,2,5-thiadiazolyl, 1,3,4-thiadiazolyl, thiazolyl, thienyl, thienothiazolyl, thienooxazolyl, thienoimidazolyl, thienyl, triazinyl, 1,2,3-triazolyl, 1,2,4-triazolyl, 1,2,5-triazolyl, and 1,3,4-triazolyl, cyano, —CO—H, —CO—OH, —CO—$OR_7$, —CO—$NH_2$, —CO—$NR_7R_7$, —CO—NH—OH, —CO—NH—$OR_7$, —CO—N($R_7$)—$OR_7$, —CO—$R_7$, —$SO_2NH_2$, —$SO_2NHR_7$, —$SO_2NR_7R_7$, —$SO_2$-heteroaryl, —$SO_2$-aryl, —CO-heteroaryl, —NH—CO—NH—$SO_2$-aryl, —NH—CO—$OR_7$, —NH—CO—NH—($C_1$-$C_6$-alkyl) or —NH—CO—($C_1$-$C_6$-alkyl), wherein each of the heteroaryl and aryl groups are optionally substituted with $C_1$-$C_6$-alkyl, nitro, hydroxy, $C_1$-$C_6$-alkoxy, —CO—O—($C_1$-$C_6$-akyl), cyano, —O-halo($C_1$-$C_6$-alkyl), halo($C_1$-$C_6$-alkyl) or halogen, or $R_2$ a group selected from

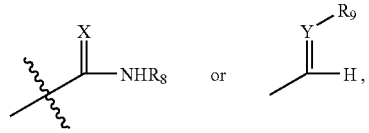

wherein $R_8$ is hydrogen or hydroxy; X is =NH or =S—; Y is =N—, and $R_9$ is hydroxy, $C_1$-$C_6$-alkoxy or aryl optionally substituted with hydroxy or $C_1$-$C_6$-alkyl;

$R_3$ is hydrogen, nitro, aryl, —O-halo($C_1$-$C_6$-alkyl), halo ($C_1$-$C_6$-alkyl), —O—($C_3$-$C_6$-cycloalkyl), —S—($C_1$-$C_6$-alkyl), heterocyclyl, $C_1$-$C_6$-alkoxy, —($C_1$-$C_6$-alkoxy)-aryl, azido, halogen, —$OCF_3$, —$CF_3$, —CO—H, —CO—OH, —CO—$OR_7$, —CO—$NH_2$, —CO—$NHR_7$, —CO—$NR_7R_7$, —CO—N($R_7$)$OR_7$, —CO—$R_7$, —$SO_2$—($C_1$-$C_6$-alkyl), —$SO_2NH_2$, —$SO_2NHR_7$, —$SO_2NR_7R_7$, —CO-heteroaryl, —$NH_2$, —$NHR_7$, —$NR_7R_7$, —OH, —N($R_7$)—CO—$R_7$, —$NHSO_2R_7$, —N($R_7$)—CO—$OR_7$ or —N($R_7$)—CO—$NR_7R_7$;

$R_4$ and $R_5$ are independently hydrogen, nitro, $C_1$-$C_6$-alkyl, aryl, —O-halo($C_1$-$C_6$-alkyl), halo($C_1$-$C_6$-alkyl), —O—($C_3$-$C_6$-cycloalkyl), —S—($C_1$-$C_6$-alkyl), heterocyclyl, $C_1$-$C_6$-alkoxy, —($C_1$-$C_6$-alkoxy)-aryl, azido, halogen, —$OCF_3$, —$CF_3$, —CO—H, —CO—OH, —CO—$OR_7$, —CO—$NH_2$, —CO—$NHR_7$, —CO—$NR_7R_7$, —CO—N($R_7$)$OR_7$, —$SO_2$—($C_1$-$C_6$-alkyl), —$SO_2NH_2$, —$SO_2NHR_7$, —$SO_2NR_7R_7$, —CO-heteroaryl, —$NH_2$, —$NHR_7$, —$NR_7R_7$, —OH, —N($R_7$)—CO—$R_7$, —$NHSO_2R_7$, —N($R_7$)—CO—$OR_7$ or —N($R_7$)—CO—$NR_7R_7$, or $R_4$ and $R_5$ together with the carbon atoms to which they are attached form a heteroaryl;

$R_6$ is hydrogen, nitro, $C_1$-$C_6$-alkyl, aryl, —O-halo($C_1$-$C_6$-alkyl), —O—($C_3$-$C_6$-cycloalkyl), —S—($C_1$-$C_6$-alkyl), heterocyclyl, $C_1$-$C_6$-alkoxy, —($C_1$-$C_6$-alkoxy)-aryl, azido, halogen, —$OCF_3$, —$CF_3$, —CO—H, —CO—OH, —CO—$OR_7$, —CO—$NH_2$, —CO—$NHR_7$, —CO—$NR_7R_7$, —CO—N($R_7$)$OR_7$, —CO—$R_7$, —$SO_2$—($C_1$-$C_6$-alkyl), —$SO_2NH_2$, —$SO_2NHR_7$, —$SO_2NR_7R_7$, —CO-heteroaryl, —$NH_2$, —$NHR_7$, —$NR_7R_7$, —OH, —N($R_7$)—CO—$R_7$, —$NHSO_2R_7$, —N($R_7$)—CO—$OR_7$ or —N($R_7$)—CO—$NR_7R_7$;

$R_7$ is $C_1$-$C_6$-alkyl, —($C_1$-$C_6$-alkyl)-OH, —($C_1$-$C_6$-alkyl)-O—($C_1$-$C_6$-alkyl), —($C_1$-$C_6$-alkyl)—CN, $C_2$-$C_6$-alkene, heterocyclyl, aryl, heteroaryl or —($C_1$-$C_6$-alkyl)-aryl, wherein each of the aryl, heterocyclyl and heteroaryl groups are optionally substituted with $C_1$-$C_6$-alkyl, nitro, hydroxy, $C_1$-$C_6$-alkoxy, —CO—O—($C_1$-$C_6$-alkyl), cyano, —O-halo($C_1$-$C_6$-alkyl), halo ($C_1$-$C_6$-alkyl) or halogen; and provided that:

when $R_2$ to $R_6$ are hydrogen, $R_1$ is not —CO—H; and the compound of formula I is not 8-methyltetrazolo[1,5-a]quinoline-4-carbaldehyde.

3. The compound according to claim 2 wherein $R_1$ is —CO—NH—$OR_7$, $R_5$ is halogen, and $R_2$ to $R_4$ and $R_6$ are hydrogen.

4. A compound of formula

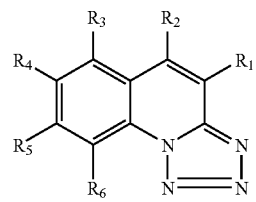

wherein $R_1$ is —CO—NH—$OR_7$, $R_2$ to $R_4$ and $R_6$ are hydrogen, $R_7$ is hydrogen and $R_5$ is chloro.

5. The compound according to claim 2 wherein $R_1$ is —CO—NH—$OR_7$, $R_6$ is halogen and $R_2$ to $R_5$ are hydrogen.

6. The compound according to claim 5 wherein $R_7$ is isobutyl, propyl, isopropyl or ethyl and $R_6$ is chloro.

7. The compound according to claim 2 wherein $R_1$ is —CO—H or —CO—NH—$OR_7$.

8. The compound according to claim 2 wherein $R_1$ is —CO—NH—$OR_7$; $R_6$ is $C_1$-$C_6$-alkyl, halogen, or —O—($C_1$-$C_6$-alkyl); and $R_2$ to $R_5$ are hydrogen.

9. A compound selected form the group consisting of
9-chloro-N-isobutoxytetrazolo[1,5-a]quinoline-4-carboxamide;
9-chloro-N-propoxytetrazolo[1,5-a]quinoline-4-carboxamide;
9-chloro-N-isopropoxytetrazolo[1,5-a]quinoline-4-carboxamide;
9-chloro-N-ethoxytetrazolo[1,5-a]quinoline-4-carboxamide;
8-chloro-N-hydroxytetrazolo[1,5-a]quinoline-4-carboxamide, and
a pharmaceutically acceptable salt thereof.

10. A compound selected form the group consisting of
9-chloro-N-isobutoxytetrazolo[1,5-a]quinoline-4-carboxamide;
9-chloro-N-propoxytetrazolo[1,5-a]quinoline-4-carboxamide;
9-chloro-N-isopropoxytetrazolo[1,5-a]quinoline-4-carboxamide;
9-chloro-N-ethoxytetrazolo[1,5-a]quinoline-4-carboxamide;
8-chloro-N-hydroxytetrazolo[1,5-a]quinoline-4-carboxamide;
8-(cyclopentyloxy)tetrazolo[1,5-a]quinoline-4-carbaldehyde;
8-chloro-7-methoxytetrazolo[1,5-a]quinoline-4-carbaldehyde;
8-(methylthio)tetrazolo[1,5-a]quinoline-4-carbaldehyde;
8-methoxytetrazolo[1,5-a]quinoline-4-carbaldehyde;
8-chloro-N-(tetrahydro-2H-pyran-2-yloxy)tetrazolo[1,5-a]quinoline-4-carboxamide;
N-(allyloxy)-9-chlorotetrazolo[1,5-a]quinoline-4-carboxamide;
N-(tert-butoxy)-9-chlorotetrazolo[1,5-a]quinoline-4-carboxamide;
7,8-dimethoxytetrazolo[1,5-a]quinoline-4-carbaldehyde;
N-hydroxy-9-methyltetrazolo[1,5-a]quinoline-4-carboxamide;
9-chloro-N-hydroxytetrazolo[1,5-a]quinoline-4-carboxamide;
8-chloro-N-hydroxytetrazolo[1,5-a]quinoline-4-carboxamide;
7-chloro-N-hydroxytetrazolo[1,5-a]quinoline-4-carboxamide;
N-hydroxytetrazolo[1,5-a]quinoline-4-carboxamide;
N-hydroxy-8-(trifluoromethoxy)tetrazolo[1,5-a]quinoline-4-carboxamide;
8-chloro-N-hydroxy-7-methoxytetrazolo[1,5-a]quinoline-4-carboxamide;
8-chloro-7-methoxy-N-(tetrahydro-2H-pyran-2-yloxy)tetrazolo[1,5-a]quinoline-4-carboxamide;
8-methoxy-N-(tetrahydro-2H-pyran-2-yloxy)tetrazolo[1,5-a]quinoline-4-carboxamide;
7-chloro-N-(tetrahydro-2H-pyran-2-yloxy)tetrazolo[1,5-a]quinoline-4-carboxamide;
7,8-dimethoxy-N-(tetrahydro-2H-pyran-2-yloxy)tetrazolo[1,5-a]quinoline-4-carboxamide;
9-methyl-N-(tetrahydro-2H-pyran-2-yloxy)tetrazolo[1,5-a]quinoline-4-carboxamide;
N-(tetrahydro-2H-pyran-2-yloxy)tetrazolo[1,5-a]quinoline-4-carboxamide;
N-(tetrahydro-2H-pyran-2-yloxy)-8-(trifluoromethoxy)tetrazolo[1,5-a]quinoline-4-carboxamide;
8-chloro-N-hydroxy-N-methyltetrazolo[1,5-a]quinoline-4-carboxamide;
9-chloro-N-(tetrahydro-2H-pyran-2-yloxy)tetrazolo[1,5-a]quinoline-4-carboxamide;
N-hydroxy-8,9-dihydro[1,4]dioxino[2,3-g]tetrazolo[1,5-a]quinoline-4-carboxamide;
N-hydroxy-7,8-dimethoxytetrazolo[1,5-a]quinoline-4-carboxamide;
N-hydroxy-8-(trifluoromethyl)tetrazolo[1,5-a]quinoline-4-carboxamide;
7-fluoro-N-hydroxytetrazolo[1,5-a]quinoline-4-carboxamide;
N-hydroxy-8-methoxytetrazolo[1,5-a]quinoline-4-carboxamide;
7,9-dimethyl-N-(tetrahydro-2H-pyran-2-yloxy)tetrazolo[1,5-a]quinoline-4-carboxamide;
N-hydroxy-7,9-dimethyltetrazolo[1,5-a]quinoline-4-carboxamide;
7,9-dichloro-N-hydroxytetrazolo[1,5-a]quinoline-4-carboxamide;
7,9-dichloro-N-(tetrahydro-2H-pyran-2-yloxy)tetrazolo[1,5-a]quinoline-4-carboxamide;
6-chloro-N-(tetrahydro-2H-pyran-2-yloxy)tetrazolo[1,5-a]quinoline-4-carboxamide;
6-chloro-N-hydroxytetrazolo[1,5-a]quinoline-4-carboxamide;
and pharmaceutically acceptable salts thereof.

11. A composition comprising a pharmaceutically acceptable carrier and a compound of formula

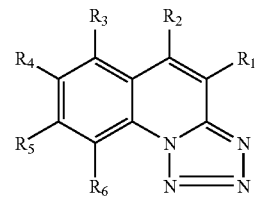

or a pharmaceutically acceptable salt thereof wherein $R_1$ is —CO—H, —CO—$NR_7R_7$, —CO—NH—OH, —CO—NH—$OR_7$, or —CO—N($R_7$)—$OR_7$, $R_2$ is hydrogen, $C_1$-$C_6$-alkyl, heterocyclic, $C_1$-$C_6$-alkyl-OH, aryl heteroaryl, halogen, cyano, —CO—H, —CO—OH, —CO—$OR_7$, —CO—$NH_2$, —CO—$NHR_7$, —CO—$NR_7R_7$, —CO—NH—OH, —CO—NH—$OR_7$, —CO—N($R_7$)—$OR_7$, —CO—$R_7$, —$SO_2NH_2$, —$SO_2NHR_7$, —$SO_2NR_7R_7$, —$SO_2$-heteroaryl, —$SO_2$-aryl, —$NHR_7$, $C_1$-$C_6$-alkyl-NH($R_7$)-aryl, —NH($R_7$)-aryl, —CO-heteroaryl, —NH—CO—O—$R_7$-aryl, —NH—CO—NH—$SO_2$-aryl, —NH—CO—$OR_7$, —NH—CO—NH—($C_1$-$C_6$-alkyl) or —NH—CO—($C_1$-$C_6$-alkyl), wherein each of the heteroaryl and aryl groups are optionally substituted with $C_1$-$C_6$-alkyl, nitro, hydroxy, $C_1$-$C_6$-alkoxy, —CO—O—($C_1$-$C_6$-akyl), cyano, —O-halo($C_1$-$C_6$-alkyl), halo($C_1$-$C_6$-alkyl) or halogen, or $R_2$ is a group selected from

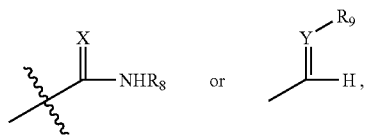

wherein $R_8$ is hydrogen or hydroxy; X is =NH or =S—; Y is =N—, and $R_9$ is hydroxy, $C_1$-$C_6$-alkoxy or aryl optionally substituted with hydroxy or $C_1$-$C_6$-alkyl;

$R_3$ and $R_6$ are independently hydrogen, nitro, $C_1$-$C_6$-alkyl, aryl, —O-halo($C_1$-$C_6$-alkyl), halo($C_1$-$C_6$-alkyl), —O—($C_3$-$C_6$-cycloalkyl), —S—($C_1$-$C_6$-alkyl), heterocyclyl, $C_1$-$C_6$-alkoxy, —($C_1$-$C_6$-alkoxy)-aryl, azido, halogen, —OCF$_3$, —CF$_3$, —CO—H, —CO—OH, —CO—OR$_7$, —CO—NH$_2$, —CO—NHR$_7$, —CO—NR$_7$R$_7$, —CO—N(R$_7$)OR$_7$, —CO—R$_7$, —SO$_2$—($C_1$-$C_6$-alkyl), —SO$_2$NH$_2$, —SO$_2$NHR$_7$, —SO$_2$NR$_7$R$_7$, —CO-heteroaryl, —NH$_2$, —NHR$_7$, —NR$_7$R$_7$, —OH, —N(R$_7$)—CO—R$_7$, —NHSO$_2$R$_7$, —N(R$_7$)—CO—OR$_7$ or —N(R$_7$)—CO—NR$_7$R$_7$;

$R_4$ and $R_5$ are independently hydrogen, nitro, $C_1$-$C_6$-alkyl, aryl, —O-halo($C_1$-$C_6$-alkyl), halo($C_1$-$C_6$-alkyl), —O—($C_3$-$C_6$-cycloalkyl), —S—($C_1$-$C_6$-alkyl), heterocyclyl, $C_1$-$C_6$-alkoxy, —($C_1$-$C_6$-alkoxy)-aryl, azido, halogen, —OCF$_3$, —CF$_3$, —CO—H, —CO—OH, —CO—OR$_7$, —CO—NH$_2$, —CO—NHR$_7$, —CO—NR$_7$R$_7$, —CO—N(R$_7$)OR$_7$, —SO$_2$—($C_1$-$C_6$-alkyl), —SO$_2$NH$_2$, —SO$_2$NHR$_7$, —SO$_2$NR$_7$R$_7$, —CO-heteroaryl, —NH$_2$, —NHR$_7$, —NR$_7$R$_7$, —OH, —N(R$_7$)—CO—R$_7$, —NHSO$_2$R$_7$, —N(R$_7$)—CO—OR$_7$ or —N(R$_7$)—CO—NR$_7$R$_7$, or $R_4$ and $R_5$ together with the carbon atoms to which they are attached form a heteroaryl; and $R_7$ is $C_1$-$C_6$-alkyl, —($C_1$-$C_6$-alkyl)-OH, —($C_1$-$C_6$-alkyl)-O—($C_1$-$C_6$-alkyl), —($C_1$-$C_6$-alkyl)-CN, $C_2$-$C_6$-alkene, heterocyclyl, aryl, heteroaryl or —($C_1$-$C_6$-alkyl)-aryl, wherein each of the aryl, heterocyclyl and heteroaryl groups are optionally substituted with $C_1$-$C_6$-alkyl, nitro, hydroxy, $C_1$-$C_6$-alkoxy, —CO—O—($C_1$-$C_6$-alkyl), cyano, —O-halo($C_1$-$C_6$-alkyl), halo($C_1$-$C_6$-alkyl) or halogen.

12. A composition according to claim 11 wherein $R_1$ is —CO—H, or —CO—NH—OR$_7$, $R_4$ and $R_5$ are independently selected from hydrogen, —S—($C_1$-$C_6$-alkyl), $C_1$-$C_6$-alkyl, —O—($C_3$-$C_6$-cycloalkyl), $C_1$-$C_6$-alkoxy, halogen, —SO$_2$—($C_1$-$C_6$-alkyl), heterocyclyl, —O-halo($C_1$-$C_6$-alkyl), halo($C_1$-$C_6$-alkyl), —NH$_2$ or together with the carbon atom to which they are attached form a heteroaryl group; $R_2$, $R_3$ and $R_6$ are hydrogen; and wherein the each of the aryl, heteroaryl and heterocyclyl groups are optionally substituted with —CO—O—($C_1$-$C_6$-alkyl), $C_1$-$C_6$-alkyl, nitro, hydroxy, $C_1$-$C_6$-alkoxy, cyano, —O-halo($C_1$-$C_6$-alkyl), halo($C_1$-$C_6$-alkyl) or halogen.

13. A composition according to claim 11 wherein $R_1$ is —CO—NH—OR$_7$.

14. A compound of the formula

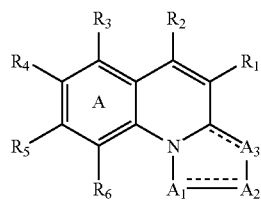

I or a pharmaceutically acceptable salt thereof wherein $R_1$ is hydrogen, $C_1$-$C_6$-alkyl, heterocyclic, $C_1$-$C_6$-alkyl-OH, heteroaryl selected from the group consisting of acridinyl, azocinyl, benzimidazolyl, benzofuranyl, benzothiofuranyl, benzothienyl, benzoxazolyl, benzthiazolyl, benztriazolyl, benztetrazolyl, benzisoxazolyl, benzisothiazolyl, benzimidazolinyl, carbazolyl, 4aH-carcanbazolyl, furanyl, furazanyl, imidazolidinyl, imidazolinyl, imidazolyl, 1H-indazolyl, isobenzofuranyl, isoindazolyl, isoindolinyl, isoindolyl, isoquinolinyl, isothiazolyl, isoxazolyl, naphthyridinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, purinyl, pyranyl, pyrazinyl, pyrazolidinyl, pyrazolinyl, pyrazolyl, pyridazinyl, pyridooxazole, pyridoimidazole, pyridothiazole, pyrimidinyl, pyridyl, pyridinyl, pyrrolyl, quinazolinyl, quinolinyl, quinoxalinyl, 1,2,3-thiadiazolyl, 1,2,4-thiadiazolyl, 1,2,5-thiadiazolyl, 1,3,4-thiadiazolyl, thiazolyl, thienyl, thienothiazolyl, thienooxazolyl, thienoimidazolyl, thienyl, triazinyl, 1,2,3-triazolyl, 1,2,4-triazolyl, 1,2,5-triazolyl, and 1,3,4-triazolyl, halogen, —CO—H, —CO—OH, —CO—NH$_2$, —CO—NR$_7$R$_7$, —CO—NH—OH, —CO—NH—OR$_7$, —CO—N(R$_7$)—OR$_7$, —CO—R$_7$, —SO$_2$NH$_2$, —SO$_2$NHR$_7$, —SO$_2$NR$_7$R$_7$, —SO$_2$-heteroaryl, —NHR$_7$, —CO-heteroaryl, —NH—CO—NH—SO$_2$-aryl, —NH—CO—OR$_7$, —NH—CO—NH—($C_1$-$C_6$-alkyl) or —NH—CO—($C_1$-$C_6$-alkyl), wherein each of the heteroaryl and aryl groups are optionally substituted with $C_1$-$C_6$-alkyl, nitro, hydroxy, $C_1$-$C_6$-alkoxy, —CO—O—($C_1$-$C_6$-akyl), cyano, —O-halo($C_1$-$C_6$-alkyl), halo($C_1$-$C_6$-alkyl) or halogen, or $R_1$ a group selected from

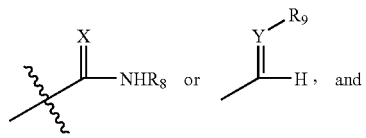

$R_2$ is —CO—H, —CO—NR$_7$R$_7$, —CO—NH—OH, —CO—NH—OR$_7$, or —CO—N(R$_7$)—OR$_7$;

$R_8$ is hydrogen or hydroxyl; X is =NH or S—, Y is =N—, $R_9$ is hydroxyl, $C_1$-$C_6$-alkoxy or aryl optionally substituted with hydroxyl or $C_1$-$C_6$-alkyl; $R_3$ is hydrogen, nitro, aryl, —O-halo($C_1$-$C_6$-alkyl), halo($C_1$-$C_6$-alkyl), —O—($C_3$-$C_6$-cycloalkyl), —S—($C_1$-$C_6$-alkyl), heterocyclyl, $C_1$-$C_6$-alkoxy, —($C_1$-$C_6$-alkoxy)-aryl, azido, halogen, —OCF$_3$, —CF$_3$, —CO—H, —CO—OH, —CO—OR$_7$, —CO—NH$_2$, —CO—NHR$_7$, —CO—NR$_7$R$_7$, —CO—N(R$_7$)OR$_7$, —CO—R$_7$, —SO$_2$—($C_1$-$C_6$-alkyl), —SO$_2$NH$_2$, —SO$_2$NHR$_7$, —SO$_2$NR$_7$R$_7$, —CO-heteroaryl, —NH$_2$, —NHR$_7$, —NR$_7$R$_7$, —OH, —N(R$_7$)—CO—R$_7$, —NHSO$_2$R$_7$, —N(R$_7$)—CO—OR$_7$ or —N(R$_7$)—CO—NR$_7$R$_7$;

$R_4$ and $R_5$ are independently hydrogen, nitro, $C_1$-$C_6$-alkyl, aryl, —O-halo($C_1$-$C_6$-alkyl), halo($C_1$-$C_6$-alkyl), —O—($C_3$-$C_6$-cycloalkyl), —S—($C_1$-$C_6$-alkyl), heterocyclyl, $C_1$-$C_6$-alkoxy, —($C_1$-$C_6$-alkoxy)-aryl, azido, halogen, —OCF$_3$, —CF$_3$, —CO—H, —CO—OH, —CO—OR$_7$, —CO—NH$_2$, —CO—NHR$_7$, —CO—NR$_7$R$_7$, —CO—N(R$_7$)OR$_7$, —SO$_2$—($C_1$-$C_6$-alkyl), —SO$_2$NH$_2$, —SO$_2$NHR$_7$, —SO$_2$NR$_7$R$_7$, —CO-heteroaryl, —NH$_2$, —NHR$_7$, —NR$_7$R$_7$, —OH, —N(R$_7$)—CO—R$_7$, —NHSO$_2$R$_7$, —N(R$_7$)—CO—OR$_7$ or —N(R$_7$)—CO—NR$_7$R$_7$, or R$_4$ and R$_5$ together with the carbon atoms to which they are attached form a heteroaryl;

R$_6$ is hydrogen, nitro, C$_1$-C$_6$-alkyl, aryl, —O-halo(C$_1$-C$_6$-alkyl), —O—(C$_3$-C$_6$-cycloalkyl), —S—(C$_1$-C$_6$-alkyl), heterocyclyl, C$_1$-C$_6$-alkoxy, —(C$_1$-C$_6$-alkoxy)-aryl, azido, halogen, —OCF$_3$, —CF$_3$, —CO—H, —CO—OH, —CO—OR$_7$, —CO—NH$_2$, —CO—NHR$_7$, —CO—NR$_7$R$_7$, —CO—N(R$_7$)OR$_7$, —CO—R$_7$, —SO$_2$—(C$_1$-C$_6$-alkyl), —SO$_2$NH$_2$, —SO$_2$NHR$_7$, —SO$_2$NR$_7$R$_7$, —CO-heteroaryl, —NH$_2$, —NHR$_7$, —NR$_7$R$_7$, —OH, —N(R$_7$)—CO—R$_7$, —NHSO$_2$R$_7$, —N(R$_7$)—CO—OR$_7$ or —N(R$_7$)—CO—NR$_7$R$_7$;

R$_7$ is —C$_1$-C$_6$alkyl, —(C$_1$-C$_6$-alkyl)-OH, —(C$_1$-C$_6$-alkyl)-O—(C$_1$-C$_6$-alkyl), —(C$_1$-C$_6$-alkyl)-CN, C$_2$-C$_6$-alkene, heterocyclyl, aryl, heteroaryl or —(C$_1$-C$_6$-alkyl)-aryl, wherein each of the aryl, heterocyclyl and heteroaryl groups are optionally substituted with C$_1$-C$_6$-alkyl, nitro, hydroxyl, C$_1$-C$_6$-alkoxy, —CO—O—(C$_1$-C$_6$-alkyl), cyano, —O-halo(C$_1$-C$_6$-alkyl), halo (C$_1$-C$_6$-alkyl) or halogen; and A$_1$, A$_2$ and A$_3$ are nitrogen.

15. A compound of the formula

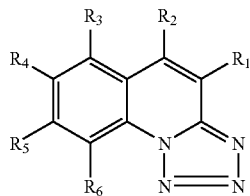

or a pharmaceutically acceptable salt thereof wherein

R$_1$ is C$_1$-C$_6$-alkyl-OH, aryl, heteroaryl selected from the group consisting of acridinyl, azocinyl, benzimidazolyl, benzofuranyl, benzothiofuranyl, benzothienyl, benzoxazolyl, benzthiazolyl, benztriazolyl, benztetrazolyl, benzisoxazolyl, benzisothiazolyl, benzimidazolinyl, carbazolyl, 4aH-carbazolyl, furanyl, furazanyl, imidazolidinyl, imidazolinyl, imidazolyl, 1H-indazolyl, isobenzofuranyl, isoindazolyl, isoindolinyl, isoindolyl, isoquinolinyl, isothiazolyl, isoxazolyl, naphthyridinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, purinyl, pyranyl, pyrazinyl, pyrazolidinyl, pyrazolinyl, pyrazolyl, pyridazinyl, pyridooxazole, pyridoimidazole, pyridothiazole, pyrimidinyl, pyrrolyl, pyridyl, pyridinyl, quinazolinyl, quinolinyl, quinoxalinyl, 1,2,3-thiadiazolyl, 1,2,4-thiadiazolyl, 1,2,5-thiadiazolyl, 1,3,4-thiadiazolyl, thiazolyl, thienyl, thienothiazolyl, thienooxazolyl, thienoimidazolyl, thienyl, triazinyl, 1,2,3-triazolyl, 1,2,4-triazolyl, 1,2,5-triazolyl, and 1,3,4-triazolyl, —CO—H, —CO—OH, —CO—OR$_7$, —CO—NH$_2$, —CO—NR$_7$R$_7$, —CO—NH—OH, —CO—NH—OR$_7$, —CO—N(R$_7$)—OR$_7$, —CO—R$_7$, —SO$_2$NH$_2$, —SO$_2$NHR$_7$, —SO$_2$NR$_7$R$_7$, —SO$_2$-heteroaryl, —NHR$_7$, —CO-heteroaryl, —NH—CO—NH—SO$_2$-aryl, —NH—CO—OR$_7$, —NH—CO—NH—(C$_1$-C$_6$-alkyl) or —NH—CO—(C$_1$-C$_6$-alkyl), wherein each of the heteroaryl and aryl groups are optionally substituted with C$_1$-C$_6$-alkyl, nitro, hydroxy, C$_1$-C$_6$-alkoxy, —CO—O—(C$_1$-C$_6$-akyl), cyano, —O-halo(C$_1$-C$_6$-alkyl), halo(C$_1$-C$_6$-alkyl) or halogen, or R$_1$ is a group selected from

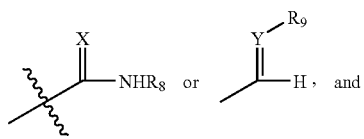

R$_2$ is —CO—H, —CO—NR$_7$R$_7$, —CO—NH—OH, —CO—NH—OR$_7$, or —CO—N(R$_7$)—OR$_7$,

R$_8$ is hydrogen or hydroxy; X is =NH or S—; Y is =N—,

R$_9$ is hydroxy, C$_1$-C$_6$-alkoxy or aryl optionally substituted with hydroxy or C$_1$-C$_6$-alkyl;

R$_3$ is hydrogen, nitro, aryl, —O-halo(C$_1$-C$_6$-alkyl), halo (C$_1$-C$_6$-alkyl), —O—(C$_3$-C$_6$-cycloalkyl), —S—(C$_1$-C$_6$-alkyl), heterocyclyl, C$_1$-C$_6$-alkoxy, —(C$_1$-C$_6$-alkoxy)-aryl, azido, halogen, —OCF$_3$, —CF$_3$, —CO—H, —CO—OH, —CO—OR$_7$, —CO—NH$_2$, —CO—NHR$_7$, —CO—NR$_7$R$_7$, —CO—N(R$_7$)OR$_7$, —CO—R$_7$, —SO$_2$—(C$_1$-C$_6$-alkyl), —SO$_2$NH$_2$, —SO$_2$NHR$_7$, —SO$_2$NR$_7$R$_7$, —CO-heteroaryl, —NH$_2$, —NHR$_7$, —NR$_7$R$_7$, —OH, —N(R$_7$)—CO—R$_7$, —NHSO$_2$R$_7$, —N(R$_7$)—CO—OR$_7$ or —N(R$_7$)—CO—NR$_7$R$_7$;

R$_4$ and R$_5$ are independently hydrogen, nitro, C$_1$-C$_6$-alkyl, aryl, —O-halo(C$_1$-C$_6$-alkyl), halo(C$_1$-C$_6$-alkyl), —O—(C$_3$-C$_6$-cycloalkyl), —S—(C$_1$-C$_6$-alkyl), heterocyclyl, C$_1$-C$_6$-alkoxy, —(C$_1$-C$_6$-alkoxy)-aryl, azido, halogen, —OCF$_3$, —CF$_3$, —CO—H, —CO—OH, —CO—OR$_7$, —CO—NH$_2$, —CO—NHR$_7$, —CO—NR$_7$R$_7$, —CO—N(R$_7$)OR$_7$, —SO$_2$—(C$_1$-C$_6$-alkyl), —SO$_2$NH$_2$, —SO$_2$NHR$_7$, —SO$_2$NR$_7$R$_7$, —CO-heteroaryl, —NH$_2$, —NHR$_7$, —NR$_7$R$_7$, —OH, —N(R$_7$)—CO—R$_7$, —NHSO$_2$R$_7$, —N(R$_7$)—CO—OR$_7$ or —N(R$_7$)—CO—NR$_7$R$_7$, or R$_4$ and R$_5$ together with the carbon atoms to which they are attached form a heteroaryl;

R$_6$ is hydrogen, nitro, C$_1$-C$_6$-alkyl, aryl, —O-halo(C$_1$-C$_6$-alkyl), —O—(C$_3$-C$_6$-cycloalkyl), —S—(C$_1$-C$_6$-alkyl), heterocyclyl, C$_1$-C$_6$-alkoxy, —(C$_1$-C$_6$-alkoxy)-aryl, azido, halogen, —OCF$_3$, —CF$_3$, —CO—H, —CO—OH, —CO—OR$_7$, —CO—NH$_2$, —CO—NHR$_7$, —CO—NR$_7$R$_7$, —CO—N(R$_7$)OR$_7$, —CO—R$_7$, —SO$_2$—(C$_1$-C$_6$-alkyl), —SO$_2$NH$_2$, —SO$_2$NHR$_7$, —SO$_2$NR$_7$R$_7$, —CO-heteroaryl, —NH$_2$, —NHR$_7$, —NR$_7$R$_7$, —OH, —N(R$_7$)—CO—R$_7$, —NHSO$_2$R$_7$, —N(R$_7$)—CO—OR$_7$ or —N(R$_7$)—CO—NR$_7$R$_7$;

R$_7$ is C$_1$-C$_6$-alkyl, —(C$_1$-C$_6$-alkyl)-OH, —(C$_1$-C$_6$-alkyl)-O—(C$_1$-C$_6$-alkyl), —(C$_1$-C$_6$-alkyl)-CN, C$_2$-C$_6$-alkene, heterocyclyl, aryl, heteroaryl or —(C$_1$-C$_6$-alkyl)-aryl, wherein each of the aryl, heterocyclyl and heteroaryl groups are optionally substituted with C$_1$-C$_6$-alkyl, nitro, hydroxy, C$_1$-C$_6$-alkoxy, —CO—O—(C$_1$-C$_6$-alkyl), cyano, —O-halo(C$_1$-C$_6$-alkyl), halo(C$_1$-C$_6$-alkyl) or halogen.

16. The compound selected from the group consisting of N-(tetrahydro-2H-pyran-2-yloxy)tetrazolo[1,5-a]quinoline-5-carboxamide;

N-hydroxytetrazolo[1,5-a]quinoline-5-carboxamide;

and pharmaceutically acceptable salts thereof.

17. A composition comprising a pharmaceutically acceptable carrier and a compound of formula

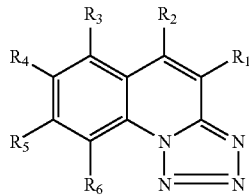

or a pharmaceutically acceptable salt thereof wherein $R_1$ is heterocyclic, $C_1$-$C_6$-alkyl-OH, aryl, heteroaryl, halogen, cyano, —CO—H, —CO—OH, —CO—$OR_7$, —CO—$NH_2$, —CO—$NR_7R_7$, —CO—NH—OH, —CO—NH—$OR_7$, —CO—N($R_7$)—$OR_7$, —CO—$R_7$, —$SO_2NH_2$, —$SO_2NHR_7$, —$SO_2NR_7R_7$, —$SO_2$-heteroaryl, —$SO_2$-aryl, —$NHR_7$, $C_1$-$C_6$-alkyl-NH($R_7$)-aryl, —NH($R_7$)-aryl, —CO-heteroaryl, —NH—CO—O—$R_7$-aryl, —NH—CO—NH—$SO_2$-aryl, —NH—CO—$OR_7$, —NH—CO—NH—($C_1$-$C_6$-alkyl) or NH—CO—($C_1$-$C_6$-alkyl), wherein each of the heteroaryl and aryl groups are optionally substituted with $C_1$-$C_6$-alkyl, nitro, hydroxy, $C_1$-$C_6$-alkoxy, —CO—O—($C_1$-$C_6$-akyl), cyano, —O-halo($C_1$-$C_6$-alkyl), halo($C_1$-$C_6$-alkyl) or halogen, or $R_1$ is a group selected from

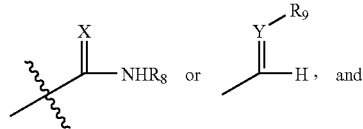

$R_2$ is —CO—H, —CO—$NR_7R_7$, —CO—NH—OH, —CO—NH—$OR_7$, or —CO—N($R_7$)—$OR_7$;

$R_8$ is hydrogen or hydroxy; X is =NH or =S—; Y is =N—, $R_9$ is hydroxy, $C_1$-$C_6$-alkoxy or aryl optionally substituted with hydroxy or $C_1$-$C_6$-alkyl;

$R_3$ and $R_6$ are independently hydrogen, nitro, $C_1$-$C_6$-alkyl, aryl, —O-halo($C_1$-$C_6$-alkyl), halo($C_1$-$C_6$-alkyl), —O—($C_3$-$C_6$-cycloalkyl), —S—($C_1$-$C_6$-alkyl), heterocyclyl, $C_1$-$C_6$-alkoxy, —($C_1$-$C_6$-alkoxy)-aryl, azido, halogen, —$OCF_3$, —$CF_3$, —CO—H, —CO—OH, —CO—$OR_7$, —CO—$NH_2$, —CO—$NHR_7$, —CO—$NR_7R_7$, —CO—N($R_7$)$OR_7$, —CO—$R_7$, —$SO_2$-($C_1$-$C_6$-alkyl), —$SO_2NH_2$, —$SO_2NHR_7$, —$SO_2NR_7R_7$, —CO-heteroaryl, —$NH_2$, —$NHR_7$, —$NR_7R_7$, —OH, —N($R_7$)—CO—$R_7$, —$NHSO_2R_7$, —N($R_7$)—CO—$OR_7$ or —N($R_7$)—CO—$NR_7R_7$;

$R_4$ and $R_5$ are independently hydrogen, nitro, $C_1$-$C_6$-alkyl, aryl, —O-halo($C_1$-$C_6$-alkyl), halo($C_1$-$C_6$-alkyl), —O—($C_3$-$C_6$-cycloalkyl), —S—($C_1$-$C_6$-alkyl), heterocyclyl, $C_1$-$C_6$-alkoxy, —($C_1$-$C_6$-alkoxy)-aryl, azido, halogen, —$OCF_3$, —$CF_3$, —CO—H, —CO—OH, —CO—$OR_7$, —CO—$NH_2$, —CO—$NHR_7$, —CO—$NR_7R_7$, —CO—N($R_7$)$OR_7$, —$SO_2$—($C_1$-$C_6$-alkyl), —$SO_2NH_2$, —$SO_2NHR_7$, —$SO_2NR_7R_7$, —CO-heteroaryl, —$NH_2$, —$NHR_7$, —$NR_7R_7$, —OH, —N($R_7$)—CO—$R_7$, —$NHSO_2R_7$, —N($R_7$)—CO—$OR_7$ or —N($R_7$)—CO—$NR_7R_7$, or $R_4$ and $R_5$ together with the carbon atoms to which they are attached form a heteroaryl; and $R_7$ is $C_1$-$C_6$-alkyl, —($C_1$-$C_6$-alkyl)-OH, —($C_1$-$C_6$-alkyl)-O—($C_1$-$C_6$-alkyl), —($C_1$-$C_6$-alkyl)-CN, $C_2$-$C_6$-alkene, heterocyclyl, aryl, heteroaryl or —($C_1$-$C_6$-alkyl)-aryl, wherein each of the aryl, heterocyclyl and heteroaryl groups are optionally substituted with $C_1$-$C_6$-alkyl, nitro, hydroxy, $C_1$-$C_6$-alkoxy, —CO—O—($C_1$-$C_6$-alkyl), cyano, —O-halo($C_1$-$C_6$-alkyl), halo($C_1$-$C_6$-alkyl) or halogen.

18. The composition according to claim 17 wherein $R_1$ is —CO—NH—$OR_7$.

* * * * *